US011419839B2

(12) United States Patent
Williams et al.

(10) Patent No.: US 11,419,839 B2
(45) Date of Patent: Aug. 23, 2022

(54) THERAPEUTIC USE OF COMPOUNDS

(71) Applicant: UCL BUSINESS LTD, London (GB)

(72) Inventors: Robin Simon Brooke Williams, Egham (GB); Matthew Walker, London (GB)

(73) Assignee: UCL BUSINESS LTD, London (GB)

( * ) Notice: Subject to any disclaimer, the term of this patent is extended or adjusted under 35 U.S.C. 154(b) by 130 days.

(21) Appl. No.: 16/723,241

(22) Filed: Dec. 20, 2019

(65) Prior Publication Data
US 2020/0268699 A1 Aug. 27, 2020

Related U.S. Application Data

(62) Division of application No. 13/989,360, filed as application No. PCT/GB2011/001646 on Nov. 24, 2011, now Pat. No. 10,548,866.

(30) Foreign Application Priority Data

Nov. 26, 2010 (GB) ...................................... 1020133

(51) Int. Cl.
*A61K 31/20* (2006.01)
(52) U.S. Cl.
CPC .................................... *A61K 31/20* (2013.01)
(58) Field of Classification Search
CPC .................................................... A61K 31/20
See application file for complete search history.

(56) References Cited

U.S. PATENT DOCUMENTS

| 5,017,613 | A | 5/1991 | Aubert et al. |
| 6,384,077 | B1 | 5/2002 | Peet et al. |
| 2003/0181523 | A1 | 9/2003 | Belliotti et al. |

FOREIGN PATENT DOCUMENTS

| JP | 2002097158 | | 4/2002 |
| JP | 2002180082 | | 6/2002 |
| JP | 2006143708 | A * | 6/2006 |
| WO | 9902485 | | 1/1999 |
| WO | WO199902485 | * | 1/1999 |
| WO | 2006094704 | | 9/2006 |

OTHER PUBLICATIONS

JP2006143708A description translation [Espacenet], Retrieved from internet (Year: 2006).*
JP2006143708A claims translation [Espacenet], Retrieved from internet (Year: 2006).*
Bonser et al. "The Anticonvulsant Actions of Octanoic and Decanoic Acids" Department of Pharmacology, University of Leeds, Leeds LS2 9JT, p. 362P.
Sills et al. "Role of octanoic and decanoic acids in the control of seizures" Archives of Disease in Childhood, 1986, vol. 61, pp. 1173-1177.
Dean et al. "HPLC Analysis of Brain and Plasma for Octanoic and Decanoic Acids" Clinical Chemistry, 1989, vol. 35, No. 9, pp. 1945-1948.
Sills et al. Archives of Disease in Childhood (1986), vol. 61, pp. 1173-1177 (Year: 1986).
Liquigen (Nutricia) [online] Retrieved from the internet [Retrieved on Jan. 7, 2018] <url:http://www.nutricia.ie/products/view/ liquigen> (Year: 2011).
Huttenlocher et al. Neurology ( 1971 ), vol. 21, pp. 1097-1103 (Year: 1971).
Mat Alon et al.,"Histone Deacetylase Inhibitors for Purging HIV-1 from the Latent Reservoir", Molecular Medicine, vol. 17, No. 5-6, May-Jun. 2011, pp. 466-472, XP002714668.
Chang et al., "Seizure control by ketogenic diet-associated medium chain fatty acids", Neuropharmacology, vol. 69, ?013, pp. 105-114, XP055075887.
European Office Action for corresponding European Application No. 14153334.9 dated Jul. 31, 2018; (13 pages).
Lambert et al. (European Journal of Pharmaceutical Sciences (2000), vol. 11, S 15-S27) (Year: 2000).
JP2002180082 translation from Espacenet (Year: 2002).
PubChem CID 2969 [online] Retrieved from internet Retrieved on Jan. 11, 2018 <url:https://pubchem.ncbi.nlm.nih.gov/ compound/ 2969#section=Top> (Year: 2018).
Nakamura et al. J. Pharmacobio-Dyn., (1990), vol. 13, pp. 76-81.
Anticonvulsant [online].2004-2005 [Retrieved on Nov. 17, 2016], Retrieved from the internet: <Url:Medical-Dictionary.thefreedictionary. com/anticonvulsant (p. 1-3)>.
Epilepsy [online]. (2007) [Retrieved on Nov. 17, 2016]. Retrieved from the internet: Medical-Dictionary. thefreedictionary.com/ epilepsy> (p. 1-11 ).
PubChem [online]. (2004) [Retrieved on Nov. 17, 2016]. Retrieved from the internet:<https://pubchem.ncbi.nlm.nih.gov/compound/ 2969>.
Japanese Office Action for Application No. P2013-540429, Dispatch No. 343568, dated Aug. 4, 2015, 11 pages.
Haldukewych et al. Monitoring Octanoic and Decanoic acids in plasma from Children with Intractable Epilepsy treated with Medium-Chain Triglyceride Diet. Clin. Chem. (1982), vol. 28, pp. 642-645.
Vogelstein et al. Cancer Genes and the pathways they control. Nature Medicine (2004), vol. 10, pp. 789-799).
Soto. Unfolding the role of protein misfolding in neurodegenerative diseases, (2003) Nature Neuroscience, vol. 4, pp. 49-60).

(Continued)

*Primary Examiner* — Umamaheswari Ramachandran
(74) *Attorney, Agent, or Firm* — K&L Gates LLP

(57) ABSTRACT

A compound having the formula (I) R1-COOH. R1 is an alkyl or alkenyl group having a $C_{7-11}$ backbone, optionally branched with a $C_{1-6}$ alkyl group at any C position in the backbone, or a pharmaceutically acceptable salt, amide or ester thereof. The backbone of the alkyl or alkenyl group, and/or the branched alkyl groups, are optionally interrupted by one or more heteroatoms, provided that when R1 is an alkyl group having a $C_7$ backbone, the branching does not consist only of a hexyl group at the a carbon of R1, or only of a methyl group at the γ carbon of R1, or of only single methyl groups at both the β and ω-1 carbons of R1, and provided that when R1 is an alkyl group having a $C_8$ or $C_{11}$ backbone, the branching does not consist only of a propyl group at the a carbon of R1.

5 Claims, 7 Drawing Sheets

Specification includes a Sequence Listing.

(56) References Cited

OTHER PUBLICATIONS

Ye et al. Amyloid-b Proteins Activate Ca2+-Permeable Channels Through Calcium-Sensing Receptors. J. Neurosci. Res. vol. 47, pp. 547-554.
National Institute of Neurological Disorders and Stroke, Seizures and Epilepsy: Hope through Research [online] [Retrieved on Dec. 15, 2014] Retrieved from internet: <http://www.ninds.nih.gov/disorders/epilepsy/detail_epilepsy.htm> pp. 1-25.
Ackermann EJ, Conde-Frieboes K, Dennis EA, Journal of Biological Chemistry 270, 445-450 (1995).
Alam et al. Surgery 146, 325-333 (2009).
Armand,V., Louvel,J., Pumain,R., & Heinemann,U. Epilepsy Res. 32, 345-355 (1998).
Backman,S.A et al. Nat. Genet. 29, 396-403 (2001).
Bakthavatsalam.D., Meijer,H.J., Noe gel.A.A., & Govers,F. Trends Microbiol. 14, 78-382 {2006).
Blaheta, Michaelis, Driever & Cinatl Med Res. Rev. 25, 383-397 (2005).
Balsinde J, Dennis EA, Journal of Biological Chemistry 271, 6758-6765 (1996).
Basselin M, Chang L, Bell JM, Rapoport SI, Neuropsychopharmacology 31, 1659-1674 {2005).
Basselin M, Chang L, Seemann R, Bell JM, Rapoport SI, J Neurochem. 85, 1553-1562 {2003).
Bazan NG, Tu B, Rodriguez de Turco EB, Prog. Brain. Res. 135, 175-185 (2002).
Bazinet RP, Rao JS, Chang L, Rapoport SI, Lee HJ, Biol. Psychiatry 59, 401-407 {2006a).
Berridge,M,J., Downes,C.P., & Hanley,M.R. Cell 59, 411-419 (1989).
Bialer,M. & White,H.S. Nat Rev Drug Discov. 9, 68-82 (2010).
Bialer,M. & Yagen,B. Neurotherapeutics. 4, 130-137 (2007).
Boeckeler K, Adley K, Xu X, Jenkins A, Jin T, Williams RS, Eur. J. Cell Biol. 85, 1047-1057 {2006).
Chang,P., Chandler,K.E., Williams,R.S., & Walker,M.C. Epilepsia (2009).
Chang MC, Contreras MA, Rosenberger TA, Rintala JJ, Bell JM, Rapoport SI, J. Neurochem. 77, 796-803 (2001).
Chapman,A.G., Meldrum,B.S., & Mendes,E. Life Sci. 32, 2023-2031 (1983). Chen CT, Green JT, On SK, Bazinet RP Prostaglandins Leukot Essent. Fatty Acids 79, 85-91 (2008).
Chen L, Iijima M, Tang M, Landree MA, Huang YE, Xiong Y, Iglesias PA, Devreotes PN, Dev. Cell 12, 603-614 (2007).
Chiu CC, Huang SY, Su KP, Lu ML, Huang MC, Chen CC, Shen WW, Eur. Neuropsychopharmacol 13, 99-103 (2003).
Costa et al. Stroke 37, 1319-1326 (2006).
De Oliveira CA, Mantovani B, Lift Science 43, 1825-1830 {1988).
Deutsch,J., Rapoport,S.L, & Rosenberger,T.A. Neurochem. Res. 28, 861-866 {2003).
Drayer,A.L., Van Der,K.J., Mayr,G.W., & Van Haastert,P.J. EMBO J. 13, 1601-1609 (1994).
Eickholt BJ, Towers GJ, Ryves WJ, Eikel D, Adley K, Ylinen LM, Chadborn NH, Harwood AJ, Nau H, Williams RS, Mu Pharmacol. 67, 1426-1433 (2005).
Eikel D, Lampen A, Nau H, Chem. Res. Toxicol. 19, 272-278 (2006).
Einat,H,, Tian,F., Belmaker,R.H., & Frost,J.W. J. Neural Transm. 115, 55-58 (2008).
Eyal S, Yagen B, Shimshoni J, Bialer M, Biochem. Pharmacol. 69, 1501-1508 (2005).
Walker,M.C et al. Epilepsia 40, 359-364 (1999).
Weeks G, Biochim. Biophys. Acta. 450, 21-32 (1976).
Williams,R.S.B. Clinical Neuroscience Research 4, 233-242 (2005).
Williams RS, Cheng L, Mudge AW, Harwood AJ, Nature 417, 292-295 (2002).
Williams RS, Eames M, Ryves WJ, Viggars J, Harwood AJ, EMBO J. 18, 2734-2745 (1999).
Wilson DB, Prescott SM, Majerus PW (1982) Discovery of an arachidonoyl coenzyme A synthetase in human platelets. J Biol Chem 257: 3510-3515.
Wirrell EC, Pediatr, Neurol. 28, 126-129 (2003).
Worsfold 0, Toma C, Nishiya T, Biosens. Bioelectron. 19, 1505-1511 (2004).
Xu X, Muller-Taubenberger A, Adley KE, Pawolleck N, Lee VW, Wiedemann C, Sihra TS, Maniak M, Jin T, Williams RS, Eukaryot. Cell 6, 899-906 (2007).
Yedgar S, Cohen Y, Shoseyov D, Biochim. Biophys. Acta. 1761, 1373-1382 (2006).
Yegin A, Akbas SH, Ozben T, Korgun DK, Acta. Neurol. Scand 106, 258-262 (2002).
Chang Pi-Shan, Thesis submitted to the University College London, Department of Clinical and Experimental Epilepsy, Institute of Neurology, Sep. 2009, 1-251.
Chang P et al., Disease Models & Mechanisms 5(1), 115-124 (Aug. 29, 2011).
Ding D et al., World Journal of Biological Psychiatry, 10(4), 893-899 (2009).
Bojic U et al., Chimical Research in Toxicology 9(5), 866-870, (1996).
Liu Jet al., Chemistry and Biodiversity 6, 503-412 (2009).
Yang Let al., Medical Hypotheses 71 (3), 465-466 (Sep. 1, 2008).
Tallandier Get al., European Journal of Medicinal Chemistry 10(5), 453-462, (1975).
Shaltiel,G et al. Valproate decreases inositol biosynthesis. Biol. Psychiatry 56, 868-874 (2004).
United States Patent Office Communication for U.S. Appl. No. 16/722,340, dated Nov. 4, 2021, 50 pages.
Löscher et al., "Pharmacological Evaluation of Various Metabolites and Analogues of Valproic Acid: Anticonvulsant and Toxic Potencies in Mice", Neuropharmacology, vol. 24, Issue No. 5, 1985, pp. 427-435.
Brazil Patent Office Communication for Application No. BR112013013039-3, dated Jan. 14, 2022, 3 pages.

\* cited by examiner

THERAPEUTIC USE OF COMPOUNDS

PRIORITY CLAIMS

This application is a divisional of U.S. application Ser. No. 13/989,360 filed Jul. 24, 2013, which is a National Stage of International Application No. PCT/GB2011/001646 filed Nov. 24, 2011, which claims priority to United Kingdom Patent Application No. 1020133.3 filed Nov. 26, 2010, the entire contents of which are incorporated herein by reference.

SEQUENCE LISTINGS

The instant application contains Sequence Listings which have been filed electronically in ASCII format and are hereby incorporated by reference in its entirety. Said ASCII copy, created on Apr. 16, 2020, is named 3712036-03508 Sequence Listing.txt and is 60,662 bytes in size.

TECHNICAL FIELD

This invention relates to uses of compounds. In particular, it relates to the use of compounds in the treatment or prevention of diseases and biomedical conditions such as, seizure-related disorders, bipolar disorders, mania, depression, migraine, attention deficit hyperactivity disorders, latent HIV infection, Alzheimer's disease, chorea and schizophrenia, ischemia, cancer and fatal blood loss.

Epilepsy is a widespread, serious neurological condition presenting considerable personal, social and economic difficulty. It affects 0.5-1% of the population, of which 30% have epilepsy that is not adequately treated with present antiepileptic drugs (Bialer and White 2010). These patients have a high mortality and morbidity rate. The understanding of cellular and molecular aspects of seizures giving rise to epilepsy is unclear, although current research has centered on defining the molecular pathways necessary for seizure progression and the development of new treatments for seizure control.

Valproic acid (VPA; 2-propylpentanoic acid; Epilim®), a short chained branched fatty acid, is the most widely used anti-epileptic world-wide, but its mechanism of action in seizure control has remained relatively unclear for over 40 years (Lagace et al., 2005; Perucca, 2002). Having been accidentally found to be effective in seizure control (Carraz G., 1967), VPA is now also used for bipolar disorders and migraine treatment, in addition to a variety of potential new therapies including cancer and HIV treatment. VPA has previously been shown to have a chronic effect in controlling inositol depletion (Williams et al., 2006; Williams, 2005), and this long-term effect is likely to be related to its efficacy in bipolar disorders.

With regard to epilepsy treatment, the therapeutic effects of VPA have been proposed to occur via directly elevating gamma-amino butyric acid (GABA) signalling (Lagace et al., 2005) and inhibiting sodium channel activity (Costa et al., 2006). Of prime importance in VPA's mechanism of action in epilepsy treatment is that it blocks seizure activity acutely—within 30 minutes of administration—corresponding to the peak concentration of VPA in the brain following intravenous injection (Aly and bdel-Latif, 1980). Despite such rapid action suggesting a direct action on channels or a biochemically-based (rather than transcriptionally-based) epilepsy target, few acute effects of VPA have been identified (Lagace et al., 2005), making rapid VPA-catalysed effects of great potential therapeutic importance. The acute effect of VPA was recently analysed using the simple model Dictyostelium (Xu et al., 2007). It demonstrated that VPA induced an inhibition of phosphatidylinositol-(3,4,5)-trisphosphate ($PIP_3$) production and a reduction in phosphatidylinositol monophosphate (PIP) and diphosphate ($PIP_2$) phosphorylation.

Bipolar disorder post mortem brain samples also show altered levels of enzymes associated with fatty acid turnover (Kim et al., 2009) as well as altered fatty acids within cell membranes (Chiu et al., 2003). Numerous studies have also shown an increase in arachidonic acid (AA) release after seizure catalysed by increased $PLA_2$ activity (Siesjo et al., 1982, Rintala et al., 1999, Bazan et al., 2002, Basselin et al., 2003), and attenuation of this process may thus provide some benefit in seizure control and epileptogenesis (Rapoport and Bosetti, 2002).

VPA has been shown to reduce AA turnover in the brain through an unknown mechanism (Chang et al., 2001). AA is an essential fatty acid and is the major polyunsaturated fatty acid in most membrane phospholipids (Svennerholm, 1968), and plays a central role in inflammatory signalling (Yedgar et al., 2006). It remains unclear if the effect of VPA on AA turnover is related to specific VPA-treatable conditions. For example, this effect may be related to bipolar disorder prophylaxis (Rapoport, 2008b) since a similar reduction in AA signalling has also been observed with other structurally independent bipolar disorder treatments such as lithium (Basselin et al., 2005) and carbamazepine (Bazinet et al., 2006a).

Although widely prescribed for multiple diseases, VPA has a number of unwanted side effects including teratogenicity and hepatotoxicity. Therefore, more potent antiepileptic drugs with reduced side effects are urgently needed.

International patent application WO 99/02485 discloses a family of VPA analogs for treating epilepsy, migraine, bipolar disorders and pain. The compounds specifically disclosed in WO 99/02485 are 2-propylheptylacetic acid, 2-propyldecanyl acetic acid and 1-O-stearoyl-2-propylheptylacetoyl-sn-glycero-3-phosphotidylcholine.

SUMMARY

Using the biomedical model Dictyostelium, the inventors found that the effect of VPA is to cause a rapid attenuation of phosphoinositide turnover, and this effect is not based upon the direct inhibition of phosphatidylinositol-3-kinase (PI3K) activity, nor is it caused through regulation of inositol recycling. They also found that VPA induced both a reduced release and an increased uptake of radiolabelled AA and palmitic acid (a saturated long chain fatty acid). This VPA-catalysed effect is not caused by reducing fatty acid activation.

In addition, structure-activity relationship (SAR) studies showed a high degree of structural specificity for these mechanisms of action. This enabled the identification of a group of compounds showing therapeutic potential similar to VPA but with the potential for reduced side effects and/or increased therapeutic efficacy.

Alignment was carried out using BLAST software. (B) Radiolabel release from wild type and PIaA cells show a similar reduction of radiolabel release in the presence of VPA. (C) Development images of Dictyostelium wild type (Ax2) cells or PlaA-ve cells at 30 hours in the absence or presence of 1 mM VPA (as indicated). Scale bars represent 500 µm.

Figure 8:
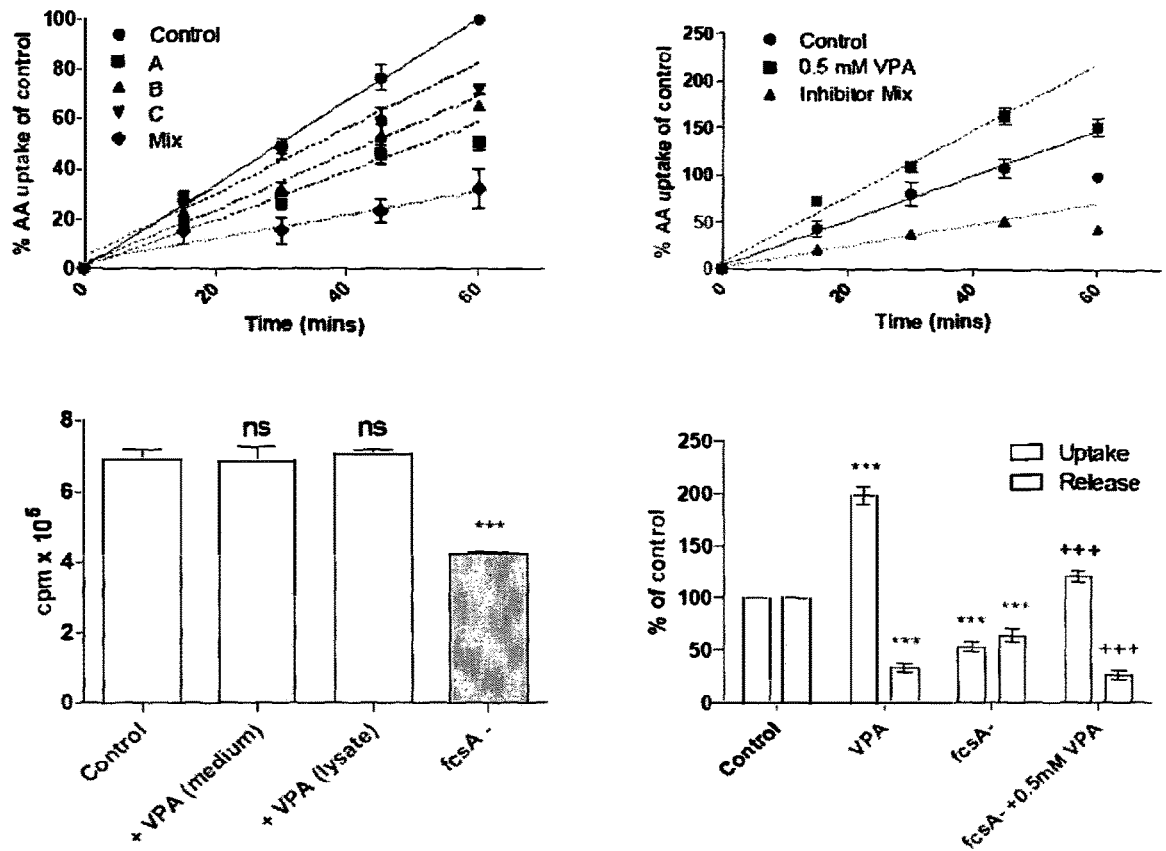

FIG. 8 demonstrates that $PLA_2$ inhibitors phenocopy VPA-induced $^3H$ release from fatty acid labelled cells. (A) Aggregation competent Dictyostelium wild type (Ax2) cells were pre-incubated with $^3H$ AA and the release of $^3H$ into external buffer is shown in the presence/absence of $PLA_2$ inhibitors. Inhibitor x=80 µM BEL, a $Ca^{2+}$ $PLA_2$ inhibitor, y=20 µM BPB, a general $PLA_2$ inhibitor and z=50 µM MAFP, a $Ca^{2+}$ dependent and $Ca^{2+}$ independent cytosolic PLA$_2$ inhibitor. Mix=combination of all inhibitors. (B) PLA$_2$ inhibitors do not mimic VPA-dependent fatty acid uptake. Cells were incubated in the presence of VPA and PLA$_2$ inhibitor mix (see methods). Uptake of $^3$H into *Dictyostelium* cell pellet is shown. (C) VPA induced $^3$H arachidonic acid uptake is independent of CoA activation. Quantification of CoA activated palmitic acid in wild type, wild type+0.5 mM VPA or fcsA−/− *Dictyostelium* (one way ANOVA, Dunnet's post hoc *p<0.001). (D) Uptake of $^3$H arachidonic acid in wild type fcsA−/− or fcsB−/− cells in the absence or presence of 0.5 mM VPA (one way ANOVA, Bonferroni post hoc, * p<0.001).

Figure 9:
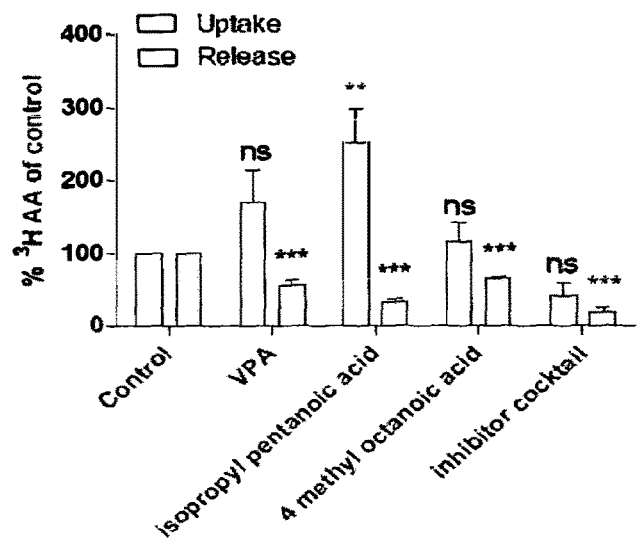

FIG. 9 shows the effect of VPA analogues on $^3$H arachidonic acid uptake and release. VPA induced parallel enhanced uptake and reduced release of radiolabel, effects which were enhanced by 2-isopropyl pentanoic acid (PIA) and reduced by 4-methyloctanoic acid. PLA$_2$ inhibitor cocktail inhibited both the uptake and the release of radiolabel (one way ANOVA, Bonferroni post hoc, ns not significant, ***p<0.001).

DETAILED DESCRIPTION

In accordance with a first aspect of the present invention, there is provided a compound having the Formula

R1-COOH          (I)

wherein R1 is an alkyl or alkenyl group having a C$_{7-11}$ backbone, optionally branched with a C$_{1-6}$ alkyl group at any C position in the backbone, or a pharmaceutically acceptable salt, amide or ester thereof, wherein the backbone of the alkyl or alkenyl group, and/or the branched alkyl groups, are optionally interrupted by one or more heteroatoms, provided that when R1 is an alkyl group having a C$_7$ backbone, the branching does not consist only of a hexyl group at the α carbon of R1, or only of a methyl group at the γ carbon of R1, or of only single methyl groups at both the β and ω-1 carbons of R1, and provided that when R1 is an alkyl group having a C$_8$ or C$_{11}$ backbone, the branching does not consist only of a propyl group at the α carbon of R1, for use in the treatment or prevention of a disease or a biomedical condition selected from a seizure-related disorders, bipolar disorders, mania, depression, migraine, attention deficit hyperactivity disorders, latent HIV infection, Alzheimer's disease, chorea, schizophrenia, ischemia, cancer and fatal blood loss, provided that, when the compound is 2-methyl-2-pentenoic acid, the disease or condition is not bipolar disorder or epilepsy.

The compounds described herein have been found to cause rapid attenuation of phosphoinositol turnover and/or attenuation of fatty acid turnover. Since attenuation of phosphoinositol and fatty acid turnover have been identified as mechanisms of action of VPA, these compounds may have the potential to be useful in the treatment or prevention of VPA-treatable conditions, such as seizure-related disorders, bipolar disorders, mania, depression, migraine, attention deficit hyperactivity disorders, latent HIV infection, Alzheimer's disease, chorea and schizophrenia, in particular, epilepsy, bipolar disorders and migraine.

In an embodiment, when R1 is an alkyl group having a C$_7$ backbone, the branching does not consist only of a methyl group at the ω-1 carbon of R1, and preferably does not comprise a methyl group at the ω-1 carbon of R1.

Compounds that can be used for the purpose of the invention include, but are not limited to, nonanoic acid, decanoic acid, 4-ethyloctanoic acid, 2-propyloctanoic acid, 2-butyloctanoic acid, 4-methylnonanoic acid, 8-methylnonanoic acid, 3-methylnonanoic acid, and 3-Methylundecanoic acid.

The term 'an alkyl group having a C$_{x-y}$ backbone' as used herein refers to a linear saturated hydrocarbon group containing from x to γ carbon atoms. For example, an alkyl group having a C$_{1-4}$ backbone refers to an unbranched saturated hydrocarbon group containing from 1 to 4 carbon atoms. Examples of an alkyl group having a C$_{1-4}$ backbone include methyl, ethyl, propyl, and butyl.

The term 'an alkenyl group having a C$_{x-y}$ backbone' as used herein refers to a linear unsaturated hydrocarbon group containing from x to γ carbon atoms and at least one (e.g. 1, 2, 3 or 4) double bonds. For example, an alkenyl group having a C$_{3-5}$ backbone refers to an unbranched unsaturated hydrocarbon group containing from 3 to 5 carbon atoms. Examples of an alkenyl group having a C$_{3-5}$ backbone include propylene, butylene and pentylene.

The terms "a carbon of R1," "β carbon of R1" and "γ carbon of R1" refer to the first, second and third carbon atoms, respectively, in a chain of carbon atoms forming R1, counting from, but not including, the COOH group of Formula (I). The term "ω-1 carbon of R1" refers to the penultimate carbon atom of a chain of carbon atoms forming R1, again counting from the COOH group of Formula (I). In other words, "ω-1 carbon of R1" is the carbon next to the terminal methyl or methylene group in R1.

The term 'C$_{x-y}$ alkyl' as used herein refers to a branched or unbranched saturated hydrocarbon group containing from x to γ carbon atoms. For example, C$_{1-4}$ alkyl refers to a branched or unbranched saturated hydrocarbon group containing from 1 to 4 carbon atoms. Examples of C$_{1-4}$ alkyl groups include methyl, ethyl, n-propyl, isopropyl, n-butyl, isobutyl, sec-butyl and tert butyl.

'Pharmaceutically acceptable salts' of compounds of the present invention include salts with inorganic bases, salts with organic bases, salts with inorganic acids, salts with organic acids and salts with basic or acidic amino acids. Salts with bases may, in particular, be employed in some instances. The compound of the present invention may be in either hydrate or non-hydrate form.

'Pharmaceutically acceptable amides' of compounds of the present invention are derivatives in which the carboxyl (i.e. —C(O)OH) groups of the said compounds are modified by reaction with an amine—NHR1'R2' so as to yield —C(O)NR1'R2' groups, wherein R1' and R2' are optionally independently selected from H, C$_{1-8}$ alkyl (e.g. C$_{1-6}$ alkyl), aryl, heteroaryl and C$_{3-8}$ cycloalkyl group.

'Pharmaceutically acceptable esters' of compounds of the present invention are derivatives in which the carboxyl (i.e. —C(O)OH) groups of the said compounds are modified by reaction with an alcoholic moiety W—OH so as to yield —C(O)OW groups, wherein W may be C$_{1-18}$ alkyl (e.g. C$_{1-6}$ alkyl), aryl, heteroaryl, or C$_{3-8}$ cycloalkyl.

General methods for the preparation of salts, amides and esters are well known to the person skilled in the art. Pharmaceutical acceptability of salts, amides and esters will depend on a variety of factors, including formulation processing characteristics and in vivo behaviour, and the skilled person would readily be able to assess such factors having regard to the present disclosure.

Where compounds of the invention exist in different enantiomeric and/or diastereoisomeric forms (including geometric isomerism about a double bond), these compounds may be prepared as isomeric mixtures or racemates, although the invention relates to all such enantiomers or isomers, whether present in an optically pure form or as mixtures with other isomers. Individual enantiomers or isomers may be obtained by methods known in the art, such as optical resolution of products or intermediates (for example chiral chromatographic separation (e.g. chiral HPLC)), or an enantiomeric synthesis approach. Similarly, where compounds of the invention may exist as alternative tautomeric forms, the invention relates to the individual tautomers in isolation, and to mixtures of the tautomers in all proportions.

In certain embodiments of the invention, R1 is an alkyl group.

In certain embodiments of the invention, R1 is an alkyl group having a $C_{7-10}$ backbone. In certain embodiments of the invention, R1 is an alkyl group having at least one point of branching, for example one, two or three points of branching.

In some embodiments, R1 is a $C_{7-10}$ backbone alkylene group comprising branching at any position in the backbone, preferably at the $\alpha$, $\beta$, $\gamma$ or $\omega$-1 carbon of R1.

In certain embodiments of the invention, the branching consists of a $C_{1-4}$ alkyl group, such as a methyl, ethyl, propyl or butyl group, preferably a methyl, ethyl or propyl group.

In particular embodiments, R1 is a $C_7$ backbone alkyl group having a branched ethyl, propyl or butyl group.

In particular embodiments, R1 is a $C_8$ backbone alkyl group having a branched methyl group.

In certain embodiments of the invention, R1 is an unbranched alkyl group.

In particular embodiments, R1 is a $C_{8-9}$ unbranched alkyl group.

In some embodiments, the one or more heteroatoms in the alkyl or alkenyl groups is selected from the group consisting of oxygen, sulphur and nitrogen. Preferably, the one or more heteroatoms is oxygen.

In certain embodiments, the compound used for the present invention is given separately, simultaneously or sequentially in combination with another pharmaceutically active agent which is known to be useful for the treatment or prevention of a disease or a biomedical condition selected from seizure-related disorders, bipolar disorders, mania, depression, migraine, attention deficit hyperactivity disorders, latent HIV infection, Alzheimer's disease, chorea, schizophrenia, ischemia, cancer and fatal blood loss, or co-morbidities thereof.

In certain embodiments, two or more of the compounds used in accordance with the first aspect of the invention can be used separately, simultaneously or sequentially in combination.

In a second aspect, the invention also provides a method of treatment or prevention of a disease or a biomedical condition selected from seizure-related disorders, bipolar disorders, mania, depression, migraine, attention deficit hyperactivity disorders, latent HIV infection, Alzheimer's disease, chorea, schizophrenia, ischemia, cancer and fatal blood loss, in particular, epilepsy, bipolar disorders and migraine, the method comprising the administration, to a subject in need of such treatment or prevention, of a therapeutically effective amount of a compound used according to the first aspect of the invention.

The compound may be administered with one or more conventional non-toxic pharmaceutically acceptable carrier, adjuvant or vehicle. Pharmaceutically acceptable carriers, adjuvants and vehicles that may be used in accordance with this invention are those conventionally employed in the field of pharmaceutical formulation, and include, but are not limited to, sugars, sugar alcohols, starches, ion exchangers, alumina, aluminium stearate, lecithin, serum proteins, such as human serum albumin, buffer substances such as phosphates, glycerine, sorbic acid, potassium sorbate, partial glyceride mixtures of saturated vegetable fatty acids, water, salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. The compound can be administered orally, parenterally, by inhalation spray, rectally, nasally, buccally, vaginally or via an implanted reservoir. The term parenteral as used herein includes subcutaneous, intracutaneous, intravenous, intramuscular, intra-articular, intrasynovial, intrasternal, intrathecal, intralesional and intracranial injection or infusion techniques.

The compound used in the present invention may be in administered in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as that described in Ph. Helv, or a similar alcohol.

The compound used for this invention may be orally administered in any orally acceptable dosage form including, but not limited to, capsules, tablets, powders, granules, and aqueous suspensions and solutions. These dosage forms are prepared according to techniques well-known in the art of pharmaceutical formulation. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The compound used for this invention may also be administered in the form of suppositories for rectal administration. For this purpose, the compound may be mixed with a suitable non-irritating excipient which is solid at room temperature but liquid at the rectal temperature and therefore will melt in the rectum to release the active components. Such materials include, but are not limited to, cocoa butter, beeswax and polyethylene glycols.

The compound used for this invention may be administered by nasal aerosol or inhalation. For this purpose, the compound is prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

The compounds used for the present invention may be administered in a dose of around 1 to around 20,000 µg/kg per dose, depending on the condition to be treated or prevented, and the characteristics of the subject being administered with the compound. In many instances, the dose may be around 1 to around 1500 µg/kg per dose. The dosing regimen for a given compound could readily be determined by the skilled person having access to this disclosure.

In accordance with a third aspect, the present invention provides the use of a compound as defined according to the first aspect of the invention in the preparation of a medicament for the treatment or prevention of a disease or a biomedical condition selected from seizure-related disorders, bipolar disorders, mania, depression, migraine, attention deficit hyperactivity disorders, latent HIV infection, Alzheimer's disease, chorea, schizophrenia, ischemia, cancer and fatal blood loss.

The invention will now be described in more detail by way of example only with reference to the figures listed below.

Materials & Methods
Chemicals and Mutants

All chemicals were provided by Sigma UK Ltd. Valproic acid congeners were provided by Sigma Aldrich UK, Alfa Aesar/Avocado, ChemSampCo, ChemCo, The NC1/DTP Open Chemical Repository or TCI europe. Radiolabelled ATP was provided by Perkin Elmer Ltd. *Dictyostelium* mutants were provided apart from the quintuple PI3K (and PTEN) knockout strain and the rPKA knockout kindly provided by R. Kay (Cambridge, UK) and A. Noegel (Koeln, Germany). *Dictyostelium* media (Axenic) was supplied by Formedium (Norfolk, UK). $^3$H arachidonic acid purchased from Hartmann analytic (Germany) and $^3$H palmitic acid from Perkin Elmer (Cambridge, UK).

Cells and Development

*Dictyostelium* cells were grown in Axenic medium or on Sussmans media plates in association with *Raoultella planticola* (Drancourt et al., 2001). All cell labelling used cells shaking (120 rpm) at 22° C., and cells were artificially developed by pulsing with cAMP (25 nM final concentration) every 6 min for 4 hours at $2.5 \times 10^6$ cells/ml in phosphate buffer (16.5 mM $KH_2PO_4$, 3.8 mM $K_2HPO_4$ pH 6.2) as described previously (Boeckeler et al., 2006).

*Dictyostelium* Phospholipid Labelling and Inositol Analysis

A saponin-based cell permeabilization protocol for *Dictyostelium* was adapted for these experiments (Pawolleck & Williams, 2009). *Dictyostelium* AX2 cells were developed for 5 hours as previously described (Boeckeler et al., 2006) (pulsed with cAMP to achieve final concentration of 25 nM), transferred to still dishes (2.5 cm), allowed to settle to give a confluent monolayer in KK2 (20 mM potassium phosphate buffer, pH 6.1) and pre-treated with compound (0.5 mM VPA or related compound or 50 µM LY294002) for 3 min. At regular time intervals, buffer was replaced with labelling solution (139 mM sodium glutamate, 5 mM glucose, 5 mM EDTA, 20 mM PIPES pH 6.6, 1 mM MgSO4.2H2O, 0.25% (w/v) saponin, 1x phosphatase inhibitor cocktails 1 and 2 (Roche Ltd), and 1 µCi/ml γ[32P]ATP) supplemented with compounds at defined concentrations.

Following a 6 min incubation, labelling solution was removed and cells were lysed in acidified methanol and phospholipids were separated as previously detailed (Williams et al., 1999). Phospholipid labelling was quantified using a Typhoon phosphor-imager. Even loading was determined using total lipid stain with copper sulphate. Inositol levels were measured from five hour developed cells (similar to phospholipid labelling), following lyophilisation, as previously described (Maslanski & Busa, 1990).

In Vitro Epilepsy Model

The rats (p21) were decapitated after killing by intraperitoneal injection with an overdose of pentobarbitone (500 mg/kg). The brain was removed and placed in ice-cold sucrose solution in mM: NaCl 87, KCl 2.5, $MgCl_2$ 7, $CaCl_2$ 0.5, $NaH_2PO_4$ 1.25, sucrose 75, glucose 25, equilibrated with 95% $O_2$/5% $CO_2$ (pH 7.4). Horizontal combined entorhinal cortex-hippocampus slices (350 µm) were prepared with a Leica vibratome (Leica VT1200S) and were then stored in an interface chamber that contained artificial cerebrospinal fluid solution (aCSF) containing in mM: NaCl 119, KCl 2.5, $MgSO_4$ 4, CaCl2 4, $NaHCO_3$ 26.2, $NaH_2PO_4$ 1, glucose 11, and gassed with 95% $O_2$/5% $CO_2$. They were stored for over one hour before being transferred to a submersion recording chamber continually perfused with carbogenated aCSF for recording. Field potential recordings were made by placing glass microelectrodes (~1-2 MΩ) filled with aCSF solution in stratum radiatum of CA1. Bipolar stimulating electrodes were positioned in the Schaffer collateral/commissural fibre pathway in stratum radiatum to confirm slice viability. In the PTZ acute seizure model, PTZ (2 mM) was added to the perfusate and [K+] was increased to 6 mM in order to induce epileptiform activity (Armand et al., 1998). In the low $Mg^{2+}$ acute seizure model, $Mg^{2+}$ free aCSF was applied to generate rhythmic short recurrent discharges. Novel anticonvulsants were applied once the frequency and amplitude of the epileptiform discharges were stable over a period of 10 min. Anticonvulsant effects were evaluated by measuring the variation of frequency of the discharges every minute. The data acquired from the 30 to 40 minutes after application novel anticonvulsants were compared by ANOVA followed by post-hoc testing using Tukey test, using SPSS statistical analysis.

In Vivo Status Epilepticus

This method has been described in detail previously (Walker et al., 1999). In brief, male Sprague Dawley rats (300-400 mg) were anesthetized with 1-2% isoflurane in $O_2$. An earth electrode was positioned subcutaneously, and a monopolar recording electrode was implanted stereotactically into the right hippocampus (coordinates, 2.5 mm lateral and 4 mm caudal from bregma). A bipolar stimulating electrode was implanted in the right hemisphere and advanced into the angular bundle (coordinates, 4.4 mm lateral and 8.1 mm caudal from bregma) to stimulate the perforant path. The depths of the electrodes were adjusted to maximize the slope of the dentate granule cell field potential (Guo et al., 1999). The electrodes were held in place with dental acrylic and skull screws. The animals were allowed to recover from anaesthesia. Seven days later, the perforant path was electrically stimulated with 4-5 mA 50 pec monopolar pulses at 20 Hz for 2 hr; this induced self-sustaining status epilepticus. After 10 min of self-sustaining status epilepticus, compounds or vehicle were administered and the behavioural seizures and EEG were monitored for 3 hours. At this point diazepam (10 mg/kg) was administered to all animals to stop the status epilepticus. Groups were compared by ANOVA followed by post-hoc testing using Tukey test, using SPSS.

Fatty Acid Uptake and Release

*Dictyostelium* cells were labelled with tritiated fatty acid in shaking liquid culture at $1.5 \times 10^6$ cells/ml with 0.5 µCi of $^3$H labelled fatty acid added in 0.5% BSA (fatty acid free BSA) per 2 treatments. Samples were taken at indicated times by removing $4.5 \times 10^6$ cells, washing once in phosphate buffer and re-suspending in phosphate buffer prior to scintillation counting. For fatty acid release experiments, cells were pulsed (as above) for 4 hours, and cells were resuspended in phosphate buffer with fatty acid free BSA (0.5%) at $1.5 \times 10^6$ cells/ml and time points were taken over one hour. Cells ($4.5 \times 10^6$ per time point) were washed to remove unincorporated radioactivity and at indicated times and the supernatant was analysed via scintillation counting. Modelling results employed using Graphpad Prism software. Bodipy labelling employed 4 hour pulsed cells, incubated with fluorescent fatty acid (Invitrogen) for 30 mM in the presence or absence of VPA (0.5 mM) and images were recorded on an Olympus IX 71 inverted fluorescence microscope with Retiga FastA 1394 camera and analysed by ImagePro™ software.

Mutant Isolation and Recapitulation and Development

Screening of a REMI library was carried out as previously described (Kuspa & Loomis, 2006) using Ax2 background, with VPA resistant mutants selected for the ability to develop in the presence of 1 mM VPA on R. planticola. Identification of the ablated gene, enabled the identified PLAa (DDB G0278525; SEQ ID NO: 16) to be recapitulated using by homologous recombination of a knockout cassette. Primers used for amplifying region within the open reading frame of the gene were (5' ATGGGAGA-TAATAAAAAAGAAAATATCAG (SEQ ID NO: 17) and 3' TAAGAATTCATGGAGATAATAAAAAAGAAAATAT-CAG (SEQ ID NO: 18), cloned by pCR2.1 TOPO (Invitrogen Ltd)), cloned into pUC19 using EcoRI digestion, and Sinai digested fragment from pBLPblp (Falx et al, 2004) was inserted into the EcoRV site of the insert. Genetic ablation was confirmed by PCR analysis. Developmental resistance to VPA was assessed by plating cells ($1 \times 10^6$) on 47 mm nitrocellulose filters (Millipore) soaked in phosphate buffer containing either 1 mM VPA or control, and development was recorded after 30 h unless otherwise stated. Development images were observed using a Leica CLS 150X microscope and images recorded using QICAM FAST 1394 camera. Fatty acid activation was determined by the method established by Wilson et al. (Wilson et al, 1982) with slight modifications. Briefly, extracts were prepared by sedimentation of $1 \times 10^7$ axenically grown cells, washing them once in 10 ml precooled 1 M TrisHCl (pH 7.5) and lysing them for 30 mM in 100 µl 1 M Tris-HCl (pH 7.5) containing 1% Triton and Protease Inhibitor Cocktail (P8340, Sigma-Aldrich, Germany) at 4° C. Twenty µg of protein extract in a volume of 140 µl were diluted into 400 µl of a buffer containing 250 mM Tris-HC 1 (pH 7.5), 10 mM MgCl2, 3 mM ATP, 0.6 mM EDTA, 0.25% Triton, and 2.5 mM DTT. 40 µl of unlabelled palmitic acid (P9767, Sigma-Aldrich, Germany) from a 100 µM methanol stock and 5 µl 3H-palmitic acid (20 µM, 1 mCi/ml) served as substrates. The reaction was started by addition of 20 41 10 mM coenzymeA-solution and incubated at 35° C. To stop the reaction 500 pi Dole's medium (0.4 ml isopropanol, 0.1 ml n-heptane, 10 µH$_2$SO$_4$) was added after 10 min. Separation of the phases was achieved by centrifugation for 30 sec at 14,000 rpm in a tabletop centrifuge. The organic phase was discarded and the aqueous phase was washed six times with 300 µl of n-heptane to remove non-activated fatty acids before the radioactivity of the acyl-CoA thioester remaining in the aqueous phase was determined in 2 ml of Lumasafe™ Plus fluid (Lumac LSC, Groningen, The Netherlands) in a scintillation counter.

Results

VPA Attenuates Phosphoinositide Signalling

Figure 1:
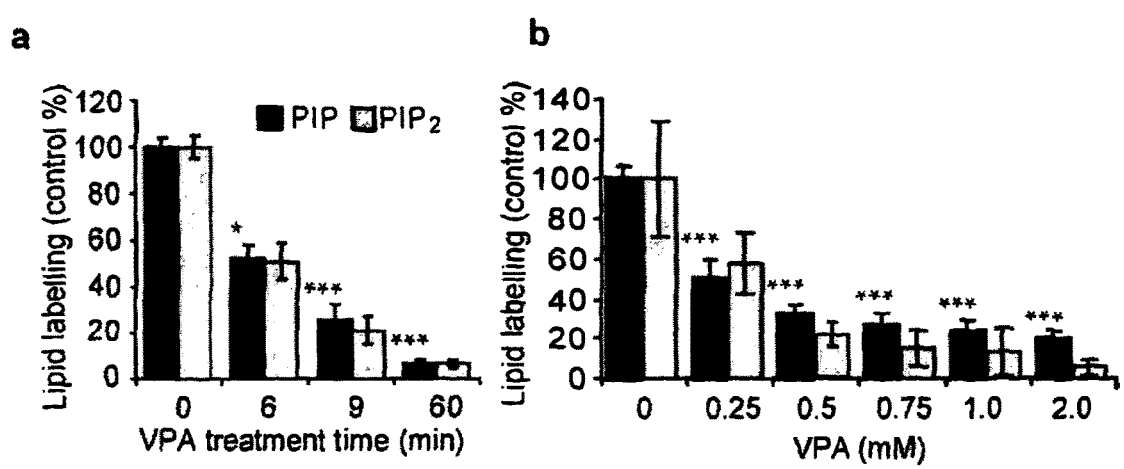
FIG. 1 shows time- and dose-dependent effect of VPA in attenuation of phosphoinositide signalling in Dictyostelium. Phosphoinositide labeling was monitored by incorporation of a radio-labelled phosphate into newly-formed lipids, followed by 10 extraction, TLC separation and quantification using a Typhoon phosphorimager (Pawolleck & Williams 2009). (a) Analysis of PIP and $PIP_2$ turnover in cells treated with VPA (0.5 mM) for indicated times. (b) Analysis of PIP and $PIP_2$ turnover in cells treated for 9 min with varying concentrations of VPA. Results are provided for triplicate experiments with duplicate samples±SD where *P<0.05; P<0.01; *P<0.001 for PIP levels.

Since the acute effect of VPA on phosphoinositide signalling has not been characterised, the inventors firstly examined the time- and concentration-dependence of drug action in Dictyostelium (FIG. 1). A rapid reduction in phosphoinositide phosphorylation was seen following 0.5 mM VPA treatment, with a 49% reduction in both radiolabelled PIP and PIP$_2$ turnover during 6 mM VPA treatment, increasing to 94% reduction in the turnover of each phosphoinositide compound following 60 min treatment (FIG. 1a). These values indicate a combination of phosphoinositide synthesis and degradation within the cell, thus reflect phosphoinositide turnover, although phosphatase activity is blocked using an inhibitor cocktail. The acute nature of this effect occurs with a similar speed to that of seizure control following intravenous VPA injection in a mouse seizure model (Honack & Loscher, 1992). The attenuation of phosphoinositide signalling was also concentration dependent, with a 25% and 42% inhibition of PIP and PIP$_2$ turnover respectively at 0.25 mM VPA following 9 min treatment increasing to a 68% and 79% reduction at 0.5 mM VPA respectively (FIG. 1b)—these concentrations are found in the therapeutic use of VPA (0.4-0.7 mM in plasma) (DSM IV, 2000). Under these conditions, this inhibitory effect of VPA provides an EC50 of 154 µM, and is independent of uptake (since cells are permeabilized with saponin). The acute, strong inhibition of phosphoinositide signalling caused by VPA made this effect of potential therapeutic interest.

A rapid reduction in phosphoinositide phosphorylation was initially thought to occur through inhibition of an unidentified lipid kinase activity. Analysis of lipid kinases traditionally employs pharmacological inhibition with enzyme class-specific compounds, but these studies are complex due to the large number of phosphatidylinositol kinase enzymes and overlapping effects between inhibitors. Since previous studies have suggested a role for VPA in attenuating the phosphatidylinositol 3-kinase (PI3K) signalling pathway (Xu et al., 2007), the inventors analysed the effect of ablating five different type 1 PI3K genes (SEQ ID NOS: 1-5) in a single cell line (Hoeller & Kay, 2007) on phosphoinositide signalling (FIG. 2a). These cells showed a 28% and 44% reduction in the formation of PIP and PIP$_2$ production respectively compared to wild type cells, suggesting a major role of these enzymes in phosphoinositide signalling. To test for a PI3K-dependence of the VPA-catalysed phosphoinositide reduction, VPA (0.5 mM) was added to these cells. It was found that VPA reduced PIP and PIP$_2$ production by 48% and 70%, respectively compared to untreated cells following 9 min treatment (FIG. 2b), indicating that these five ablated enzymes are not the target of VPA in attenuating phosphoinositide turnover.

To investigate a role of other lipid kinases in VPA-catalysed phosphoinositide attenuation, the inventors analysed two other non-related phosphatidylinositol kinases: the rPKA knockout mutant lacking an endosomal G-protein-coupled receptor protein containing a phosphatidylinositol 5 kinase (PIP5K) domain (Bakthavatsalam et al., 2006); and the PIPKinA mutant that lacks a nuclear phosphatidylinositol 4/5 kinase activity (Guo et al., 2001). Ablation of rPKA (SEQ ID NO: 6; FIG. 2a) showed a 30% and 54% reduction in PIP and PIP$_2$ production, respectively compared to wild type cells, with VPA treatment causing an additional 72% and 33% reduction compared to untreated cells (FIG. 2c). Ablation of PIPKinA (SEQ ID NO: 7) showed no significant change in PIP and PIP$_2$ production (FIG. 2a), with VPA treatment causing a 54% and 68% reduction in PIP and PIP$_2$ synthesis respectively compared to untreated cells (FIG. 2d). All three cell lines were still sensitive to pharmacological inhibition of PBK activity (using 50 μM L Y294006 an inhibitor of PI3K activity), confirming these variations were related to attenuated phosphoinositide turnover (FIGS. 2b-d). The reduced sensitivity of all three lipid kinase mutants suggests a common mechanism of VPA action independent of specific phosphatidylinositol kinase action.

Since another mechanism for regulating phosphoinositide signalling is the recycling of phosphatidylinositol, via inositol phosphates (FIG. 2e), the inventors analysed phosphoinositide turnover in isogenic mutants with this recycling pathway blocked or activated. Cells lacking the single phospholipase C gene (SEQ ID NO: 8; Drayer et al., 1994) showed no significant reduction in PIP and $PIP_2$ turnover compared to wild type cells (FIG. 20, and showed a VPA-catalysed reduction in PIP and $PIP_2$ signalling close to that for wild-type cells (73 and 75% for PIP and $PIP_2$ respectively). Cells with approximately three-fold higher inositol trisphosphate (InsP3) caused by prolyl oligopeptidase ablation (PO; SEQ ID NO: 9; Williams et al., 1999, Williams et al., 2002) showed a slight decrease in PIP levels in untreated cells (and no significant change in $PIP_2$ levels) and a VPA-catalysed reduction in PIP and $PIP_2$ signalling by 66% and 68% respectively. Furthermore, the inventors have previously shown that inhibition of inositol monophosphatase (IMPase) activity by 10 mM lithium does not attenuate phosphoinositide signalling following acute (9 min) treatment (King et al., 2009), however extended lithium treatment (60 min) reduces PIP and $PIP_2$ levels, and this effect is overcome by over-expression of IMPase (King et al., 2009). In comparison, overexpressing IMPase did not overcome extended VPA treatment (60 min; 0.5 mM) (FIG. 2g). These results suggest that elevating or reducing recycling of inositol through inositol phosphate signalling does not play a major regulatory role in acute phosphoinositide production and does not overcome VPA-catalysed acute reduction in phosphoinositide signalling in this model. These results thus provide the first strong evidence for a mechanism of action of VPA—independent of inositol depletion—in targeting phosphoinositide signalling.

Identifying Novel Compounds Showing Increased Phosphoinositide Attenuation

The identification of an acute effect of VPA in attenuating phosphoinositide signalling enabled the investigation of the structural requirements for this effect. The effect of compounds tested for the present invention on phosphoinositde attenuation are summarised in Table 1 below.

TABLE 1

| Chemical category | Chemical (common name) | Chemical (IUPAC nomenclature) | PIP Level (% control) | SD |
|---|---|---|---|---|
| | valproic acid (VPA) | 2-propylpentanoic acid | 32.0 | 8.7 |
| Shorter than 5 carbons backbone (the longest aliphatic side chain) acids | | | | |
| | Isovaleric Acid | 3-methylbutanoic acid | 37 | 9 |
| | | 3-methylbutanoic | 99.1 | 11.4 |
| | GABA | 4-aminobutanoic acid | 60.8 | 3.8 |
| | TBA | tert-butylacetic acid | 21.4 | 4.1 |
| | PIA | propylisopropylacetic acid | 15.4 | 2.2 |
| | DIA | diisopropylacetic acid | 18.6 | 4.5 |
| 5 carbon backbone acids | | | | |
| | | 4-methylpentanoic acid | 60 | 11.8 |
| | | 2-methyl-2-pentenoic acid | 14.8 | 3.8 |
| | | 4-methyl-2-pentenoic acid | 54.8 | 14.1 |
| | | 2,4-dimethyl-2-pentenoic acid | 38.4 | 6.8 |
| | | trans-pent-2-enoic acid | 50.4 | 9.1 |
| | | 2-methylpentanoic acid | 59 | 7.3 |
| | | 3-methylpentanoic acid | 64 | 13.6 |
| | | 4-methyl-2-pentenoic acid | 121 | 25 |
| | | 2,4-dimethyl-2-pentenoic acid | 94 | 14 |
| | 3-methylvaleric acid | 3-methylpentanoic acid | 66 | 12 |
| | 4-methylvaleric acid | 4-methylpentanioc acid | 102 | 18 |
| | | 3-methylpentanoic acid | 67 | 16 |
| | | 2,2-dimethyl-4-pentenoic acid | 60 | 7 |
| | | 3-methyl-4-pentenoic acid | 84 | 6 |
| 6 Carbon backbone acids | | | | |
| | | 4-methylhexanoic acid | 68 | 3 |
| | | 2-methylhexanoic acid | 68.1 | 14.8 |
| | | 5-methylhexanoic acid | 7.2 | 0.7 |
| | | 2-ethylhexanoic acid | 22.2 | 5.3 |
| | | 2,2-dimethylhexanoic | 29.7 | 9.7 |
| | | 3,5,5-trimethylhexanoic acid | 32 | 13 |
| | | 4-hexenoic acid, (cis + trans) | 58 | 15 |
| 7-9 carbon backbone acids | | | | |
| | | 2-methylheptanoic | 16.1 | 6.4 |
| | | 4-methyloctanoic acid | 12 | 1.3 |
| | | 4-ethyloctanoic acid | 13.2 | 1.8 |
| | | 4-methylnonanoic acid | 45 | 16 |
| 11 carbon backbone acids | | | | |
| | | 3-methylundecanoic acid. | 50 | 0 |
| Straight-chain acids | | | | |
| | valeric acid | pentanoic acid | 66.9 | 7.8 |
| | n-caproic acid | hexanoic acid | 49.2 | 10.1 |

TABLE 1-continued

| Chemical category | Chemical (common name) | Chemical (IUPAC nomenclature) | PIP Level (% control) | SD |
|---|---|---|---|---|
| | enanthoic acid | heptanoic acid | 31.2 | 5 |
| | caprylic acid | octanoic acid | 16.7 | 3.4 |
| | pelagonic acid | nonanoic acid | 8 | 1.7 |
| | capric acid | decanoic acid | 12.9 | 1.4 |
| | Lauric acid | dodecanoic acid | 42 | 3 |
| | Margaric acid | heptadecanoic acid, | 92.3 | 2.8 |
| | | Other acids | | |
| | Diphenylacetic acid | 2,2-diphenylacetic acid | 39 | 11 |
| | TMCA | tetramethylcyclopropane carboxylic acid | 33.9 | 7.7 |
| | | Derivatized carboxylic acids (amides) | | |
| | valpromide (VPD) | 2-propylpentamide | 69.3 | 13.3 |
| | valnocatmide (VCD) | 2-ethyl-3-methyl valeramide | 64 | 2.9 |
| | TMCD | tetramethylcyclopropane-carboxamide | 72.5 | 7.2 |
| | MTMCD | N-methyl-tetramethyl--cyclopropane carboxamide | 50.8 | 6.9 |
| | PID | propylisopropylacetamide | 59 | 12.2 |
| | | Tert-butyl amide | 47.6 | 12 |
| | | n-propyl 2-methylvalerate | 121 | 13.6 |
| Aldehydes | | methylvalerate | 46 | 5.5 |
| | valeraldehyde | pentanal | 52 | 10.8 |
| | | octanal | 260 | 199 |
| | | nonanal | 99 | 13 |
| Alcohols | | 2-propyl-1-pentanol | 101 | 13 |
| | | 2-butyl-1-octanol | 93, | 53 |
| | | 2-hexyl-1-decanol | 191 | 38 |

Although the majority of compounds analysed showed some inhibitory effect on phosphoinositide turnover (Table 1), a number of structures showed greater phosphoinositide signalling inhibition than VPA. These highly active compounds fit into two structural groups: the first comprising branched fatty acids with a roughly similar structure to VPA; and a second novel group of compounds with or without short side chains in various positions on the backbone. Within this latter group, fatty acids show a strong dependence on length, whereby 8-10 carbon backbone acids are highly active (e.g. 4-methyloctanoic acid reduces PIP and $PIP_2$ signalling by 88% and 93% respectively, and nonanoic acid by 92% and 93% respectively; Table 1) and increased or decreased backbone length reduces activity. All highly active compounds in this group are fatty acids, without predicted teratogenicity (Eickholt et al., 2005) and show a positive association with lipophilicity. This effect is also independent of acidic function, since variable activity is shown with straight carbon acids of equivalent acidity (pKa, Table 2 which shows a comparison of phosphoinositide attenuation and pKA values for VPA and straight chain acids in *Dictyostelium*). These structural distinctions provide the first characterization of VPA congeners for this effect of phosphoinositide attenuation. Interestingly, high structural specificity has previously been show for fatty acids in both anticonvulsant as well as antiallodynic (anti-neuropathic pain) activities (Kaufmann et al., 2009). Preliminary observation of behaviour in animal models for one related compound does not suggest a strong sedative effect.

TABLE 2

| Acid | Total number of Carbon atoms | pKa | PIP level % control | SD |
|---|---|---|---|---|
| VPA | 8 | 4.6 | 32.0 | 8.7 |
| Pentanoic acid | 5 | 4.84 | 66.9 | 7.8 |

TABLE 2-continued

| Acid | Total number of Carbon atoms | pKa | PIP level % control | SD |
|---|---|---|---|---|
| Hexanoic acid | 6 | 4.85 | 49.2 | 10.1 |
| Heptanoic acid | 7 | 4.89 | 31.2 | 5 |
| Octanoic acid | 8 | 4.89 | 16.7 | 3.4 |
| Nonanoic acid | 9 | 4.95 | 8 | 1.7 |
| Decanoic acid | 10 | 4.90 | 12.9 | 1.4 |
| dodecanoic acid: | 11 | 4.85 | 42 | 3 |
| heptadecanoic acid | 17 | 4.78 | 92.3 | 2.8 |

VPA has been identified as an inhibitor of de novo inositol biosynthesis, indirectly blocking the production of inositol-1-phosphate from glucose-6-phosphate (Shaltiel et al., 2004, Shaltiel et al., 2007a, Vaden et al., 2001). A role for VPA-attenuation of inositol signalling has been widely shown in models ranging from yeast (Vaden et al., 2001) and *Diciyosteliuum* (Williams et al., 1999, Williams 2002) to *Caenorhabditis elegans* (Tokuoka et at, 2008), rats and humans (Shaltiel et al., 2007a, Shaltiel et al., 2007b). Measurement of inositol and inositol trisphosphate (InsP3) levels and the inositol-dependent spreading of mammalian growth cones have all been used to show inositol depletion. Since it is not clear if a VPA-induced reduction in inositol levels may cause the a cute reduction in phosphoinositide signalling shown here, the inventors analysed phosphoinositide turnover using VPA-related compounds shown to be active in inositol depletion. Compounds showing strong InsP3 depletion in *Dictyostelium* with concomitant inositol-depletion dependent enlargement in mammalian growth cones include 2-methyl-2-pentenoic acid (Eickholt et al., 2005) and this compound showed stronger phosphoinositide attenuation than VPA. Interestingly, substituting the carboxylic acid moiety of compounds showing high phosphoinositide attenuation (VPA) with a carboxamide group (yielding the corresponding amide (VPD) reduces the inhibitory effect on phosphoinositide turnover and reduces growth cone spreading, and VPD shows weak inhibition of human myo-inositol synthase proposed as the VPA-target in inositol depletion (MIP synthase (Shaltiel et al., 2004, Shaltiel et al., 2007a)). These inositol-depleting and phosphoinositide-attenuating compounds are found mainly within the first structural group of compounds (described above), and also contain a number of potent anticonvulsants second generation to VPA currently under investigation (Bialer & Yagen, 2007). None of the novel family of longer backbone compounds identified in this study have been analysed in inositol depletion studies.

Since reduction in the inositol levels may provide the mechanism of these compounds in phosphoinositide attenuation, the inventors analysed inositol levels in treated *Dictyostelium* cells using a range of compounds from both structural groups showing variable phosphoinositide attenuation). In these experiments, VPA gave no significant reduction in inositol levels in the time period shown to cause phosphoinositide attenuation (9 min), nor did any other compound tested, and thus no correlation was found between phosphoinositide attenuation and inositol depletion. This conclusion is in agreement with previous data, based in *Dictyostelium*, showing the acute inhibition of inositol monophosphatase (by lithium) does not give rise to phosphoinositide attenuation (King et al., 2009), and depletion of inositol trisphosphate in this model by VPA requires 6 hour treatment (Williams et al., 1999)—considerably longer than the time periods used here. These experiments therefore suggest phosphoinositide attenuation provides a novel effect of VPA in *Dictyostelium* and identifies a range of compounds showing increased efficacy for this effect. Since increased PIP and $PIP_2$ levels have been observed during seizures in animal models (Van Rooij en et al., 1986), and the inventors have discovered a novel family of compounds causing this effect.

Novel Compounds Show Enhanced Efficacy in In Vitro Epileptiform Models

Figure 3:
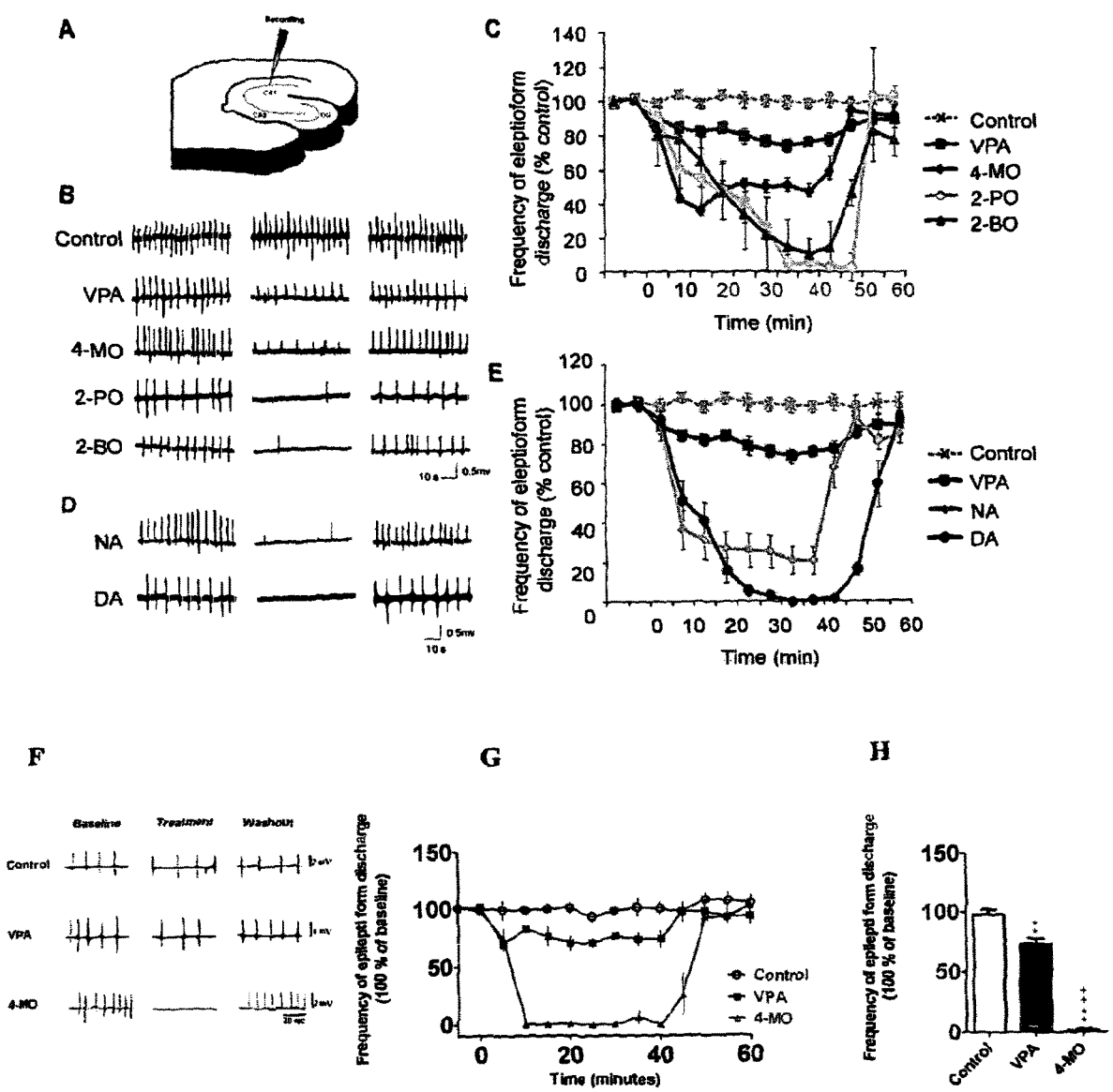
FIG. 3 shows seizure control with VPA and phosphoinositide-attenuating compounds using in vitro acute seizure mode-pentylentetrazol (PTZ) model and low magnesium model. (a) A combined entorhinal cortex-hippocampal slice preparation was placed in a submerged recording chamber and perfused with artificial cerebrospinal fluid containing high [K+] and PTZ to induce epileptiform activity prior to addition of VPA or novel compounds at 1 mM. (b) Illustration of trace samples of burst discharges following application of VPA, 4-methyloctanoic acid (4-MO), 2-propyloctanoic (2-PO), and 2-butyloctanoic acid (2-BO)). (c) Summary of the frequency of burst discharges following application of drugs plotted against time. The drugs were applied from time 0 to 40 minutes. (d) Trace samples and (e) frequency of burst discharges for longer straight chain nonanoic acid (NA) and decanoic acid (DA). (f) Illustration of trace samples of low magnesium-induced burst discharges by application of VPA (1 mM), 4-methyloctanoic acid (4-MO, 1 mM). (g) Summary of the frequency of low magnesium-induced burst discharges following application of drugs (VPA 1 mM, n=5; 4-MO 1 mM, n=5). The frequency of epileptiform activity induced by low magnesium plotted against time. The drugs were applied from time 0 to 40 minutes. Application of VPA resulted in a significant decrease in discharge frequency (72.7±3.6% of baseline, 30-40 minutes after application and the effect of suppression is reversible after wash out), whereas application of 4-MO abolished the epileptiform discharge (1.6±3.1% of baseline, n=5, p<0.01 compared to control; P<0.01 compared to VPA). The epileptiform activities in both treatment recovered during drug washout (n=5 for each drug). (h) Comparison of the mean frequency of low Mg2+-induced burst discharges for the last 10 min during drug application with different treatments, demonstrating a significant effect of all compounds in attenuating seizure activity. * P<0.05, ** P<0.01 compared to control; +P<0.05, ++P<0.01, compared to VPA treated group. Data are presented as means±SEM.

Since it is not possible to repeat these radio-labelling experiments in in vivo animal systems to replicate the inventors' mechanism-dependent findings in higher models, the inventors instead analysed the efficacy of the novel family of compounds in seizure control. For these experiments, they employed a VPA-sensitive pentelenetetrazol (PTZ) in vitro model of epileptiform activity (Armand et al., 1998) to analyse three compounds from the novel family (FIG. 3a,b) with an eight carbon backbone with variable side chain position and length. VPA significantly decreased the frequency of epileptiform discharges (Armand et al., 1998; FIG. 3b; VPA: 75.1±1.7☐). the application of equimolar concentrations of each eight carbon backbone compound also strongly reduced discharges with a significantly greater efficacy than VPA (FIGS. 3b,c). Application of all three novel compounds greatly reduced seizure discharge frequency (4-methyloctanoic acid, 49.1±4.4%, 2-propyloctanoic acid is 5.3±3.3 and 2-butyloctanoic acid 5.2±5.0% all P=0.005 compared to VPA). The inventors also extended these compounds to show a similar efficacy for straight chain nine- and ten-carbon backbones (nonanoic acid, 20.9±7.5☐, P=2×10-6 compared to VPA; decanoic acid 0.23±0.23%, P=2×10-6 compared to VPA FIG. 3d, e). This activity was not seen with shorter backbones (e.g. 5 carbon pentanoic acid—data not shown). These highly potent compounds have not previously been associated with seizure control, and would not be predicted to show teratogenic effects (Guo et al., 1999).

To show that the effect of these compounds was not seizure-model specific, the inventors further investigated the effect of one of these compounds in the in vitro low Mg' seizure model (FIGS. 3f, g, h). The inventors chose 4-methyloctanoic acid (hircinoic acid), since this is endogenous to animal systems (Johnson et al., 1977). VPA (1 mM) weakly reduced the frequency of recurrent short discharges in this model. Application of 4-methyloctanoic acid almost abolished the frequency of recurrent short discharges 30-40 minutes after application. These data therefore suggest that 4-methyloctanoic acid shows enhanced activity over VPA in multiple in vitro models of epileptiform activity.

Novel Compounds Show Enhanced Status Epilepticus Control

Figure 4:
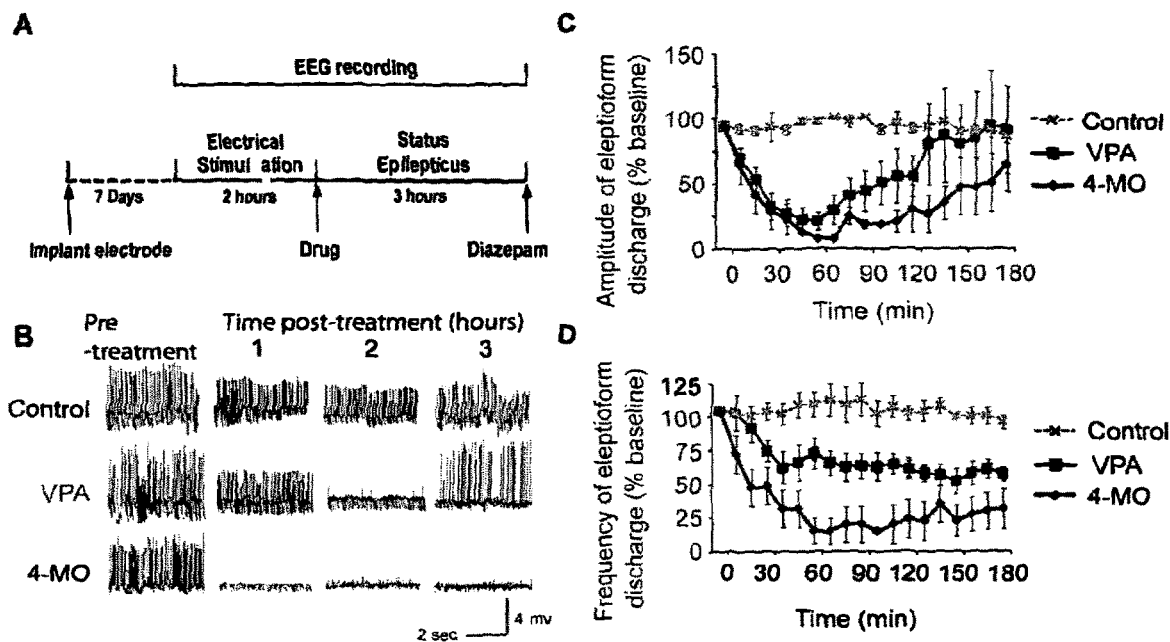
FIG. 4 shows seizure control with phosphoinositide-attenuating compounds in an in vivo seizure model. (a) Summary of the procedure—electrical induction of self-sustained status epilepticus (SSSE). Rats were electrically stimulated via the perforant pathway with 4-5 mA, 50 monopolar pulses at 20 Hz for 2 hours to induce SSSE seven days after electrode implantation. Three hours after the induction of the SSSE, the rats were given diazepam (10 mg/kg) by intraperitoneal injection (i.p.) to terminate the seizure activity. (b) Illustrative trace samples of EEG from status epilepticus animal. Administration of VPA (400 mg/kg) or 4-methyloctanoic acid (400 mg/kg) resulted in attenuation of seizure activity, whereas DMSO had no effect. (c) Time course of the effects on spike amplitude following administration of DMSO VPA (n=7) and 4-MO (n=7). (d) Time course of the effects on spontaneous spike frequency following administration of DMSO (n=5), VPA (n=7) or 4-MO (n=7).

To demonstrate further efficacy in animal seizure models with these compounds, the inventors tested 4-methyloctanoic acid in an in vivo model of status epilepticus (FIG. 4). For this test, status epilepticus was induced by stimulation of the perforant path in awake, freely moving rats as has been previously described (Holtkamp et al., 2001, Walker et al., 1999; FIG. 4a). The inventors have previously found that VPA is effective in this model at high dose (600 mg/kg) but has only partial effectiveness at a lower dose (400 mg/kg). The inventors therefore compared the efficacy of 4-methyloctanoic acid (400 mg/kg) against VPA (400 mg/kg). 4-methyloctanoic acid has a marginally higher molecular weight (MW=158) than that of VPA (MW=144) and so this dose represents a slightly lower molar dose of 4-methyloctanoic acid. VPA strongly attenuated seizures in this model 2 hours after treatment, with reduced efficacy three hours post treatment (FIG. 4b), whereas 4-methyloctanoic acid protected against seizures over the test period. Both compounds reduce spike amplitude and frequency (FIG. 4): VPA reduced spike amplitude (75.2±9.2% in the first hour; 61.1±8.3% in the second hour; 55.1±6.6% in the third hour) (FIGS. 4e,f). In comparison, 4-methyloctanoic showed significantly better control, reducing the mean spike frequency to 39.3±11.3% in the first hour (significantly better than VPA p<0.05); 18.1±10.3% in the second hour (p<0.05 compared to VPA) and 26.9±12.3% in the third hour (FIGS. 4e,f). 4-methyloctanoic terminated status epilepticus (defined as a spike frequency of less than 1 Hz) in all status epilepticus animals. Furthermore, 4-methyloctanoic acid completely stopped the seizures in all 7 animals after 2 hours, whilst VPA decreased seizure severity but did not terminate the seizures in any (P=0.0003, Fisher's exact test), and this effect was maintained in five out of seven animals given 4-methyloctanoic acid by three hours (P=0.01, Fisher's exact test).

VPA Regulates Fatty Acid Uptake and Release

Figure 5:
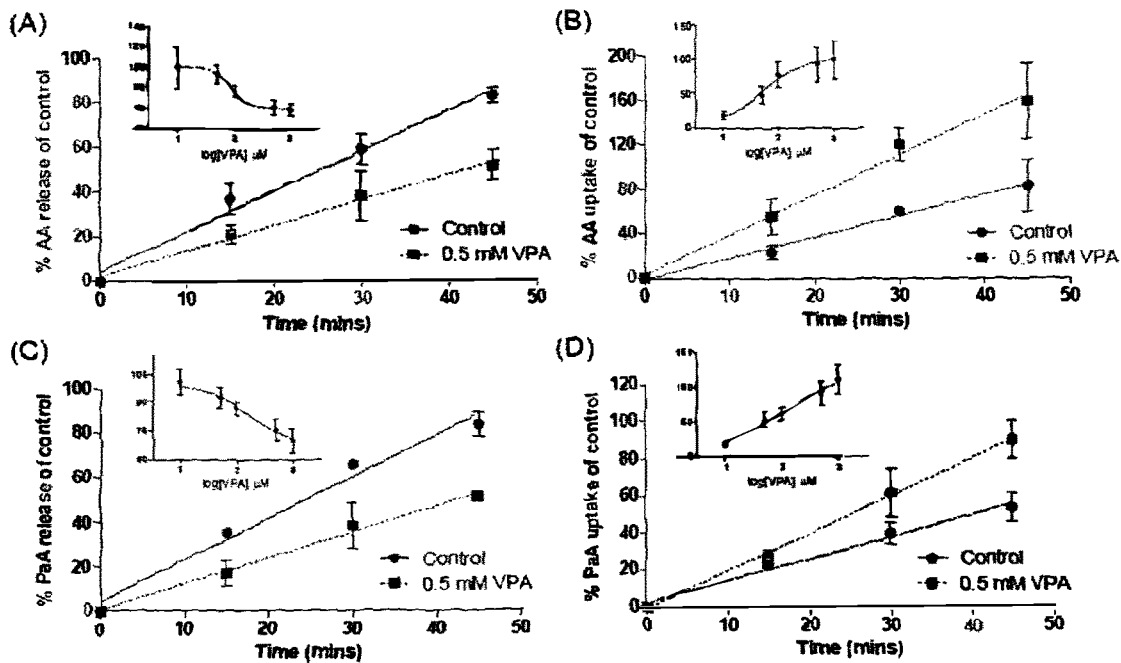
FIG. 5 demonstrates that VPA induces changes in fatty acid uptake and release in a time and concentration dependent manner. Dictyostelium wild type (Ax2) cells were pre-incubated with $^3H$ arachidonic acid (A) or palmitic acid (C) and the release of $^3H$ into external buffer is shown in the presence/absence of VPA. Fatty acid uptake was measured by incubation of cells with or without VPA and $^3H$ AA (B) or palmitic acid (D) simultaneously. Uptake of $^3H$ into Dictyostelium cell pellet is shown. All results are expressed as control at 60 minutes. Insets show dose response curves. Statistics and dose response curves were calculated using Graphpad Prizm™ software. All data are replicates of at least 3 independent experiments and show mean±SEM.

To analyse a role for VPA-mediated regulation of arachidonic acid release in *Dictyostelium*, the inventors developed an assay based upon the release of radiolabel from cells containing tritiated fatty acid over time. Using this assay, the inventors showed that following $^3$H-AA labelling of cells, the release of radiolabel into media was linear over a 45 min period (FIG. 5A). The effect of VPA on radiolabel release from AA-labelled cells was acute and dose dependent, whereby VPA induced a decrease in the release with an IC50 of 89 µM. This effect was not specific to AA, since release of tritiated palmitic acid was also inhibited in the presence of VPA with an IC50 of 163 µM (FIG. 5C). The acute nature of this effect is seen with a significant inhibition following 30 min exposure (p<0.05).

Since reduced release of labelled fatty acid may be due to its reincorporation into lipids, the inventors also measured fatty acid uptake by measuring radiolabel incorporation of fatty acids into cells. Like fatty acid release, incorporation of tritiated AA was linear over a 30 min period (FIG. 5B), however, VPA caused a dose-dependent increase in the uptake of AA, with an EC50 of 47 µM. This effect was also seen using palmitic acid, with an EC50 value of 160 µM (FIG. 5D) and was significant following 30 min drug treatment (p<0.05).

Figure 6:
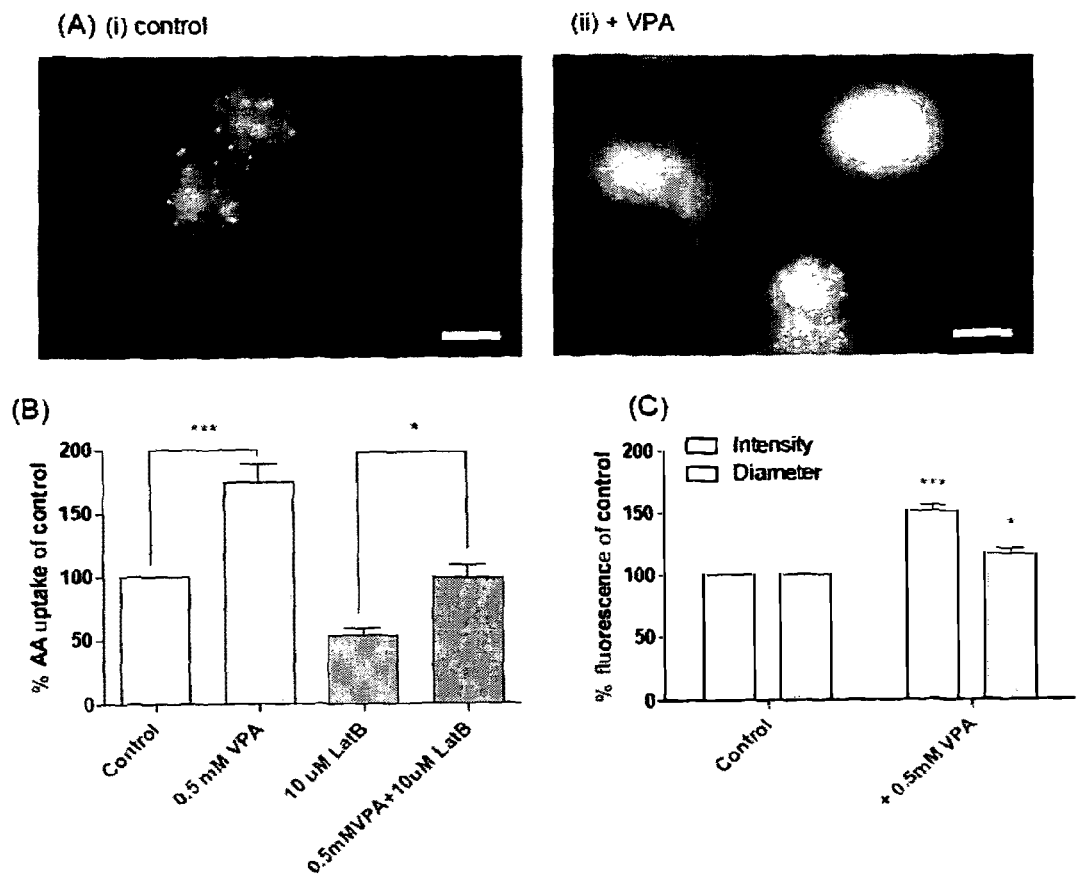
FIG. 6 demonstrates that VPA induces endocytosis independent lipid droplet accumulation of bodipy in Dictyostelium. (a) Images of bodipy fatty acid accumulation in Dictyostelium in the absence (i) or presence (ii) of 0.5 mM VPA. VPA significantly increased the droplet intensity and average diameter of lipid droplets compared to control (b) (t test, *** p<0.001, *p<0.05). The actin polymerising inhibitor latrunculin (10 µM) did not completely inhibit VPA induced increase in $^3H$ arachidonic acid uptake. All data are replicates of at least 3 independent experiments and show mean±SEM.

In order to test if the above effects occur through simple fatty acid membrane insertion, the inventors visualised fatty acid uptake using a compound containing a 12 carbon fatty acid chain linked to fluorescent head group (bodipy; FIG. 6A) (Worsfold et al., 2004). Upon incubation of cells and bodipy-labelled lipid, 0.5 mM VPA caused an increase in the intensity and diameter of fluorescent lipid droplets within cells compared to untreated cells (FIG. 6B). This results show that VPA also increased the uptake of this fatty acid, and that the drug increased fatty acid storage within lipid droplets.

VPA-Induced Fatty Acid Uptake Occurs Independently of Actin Dynamics

Uptake (and release) of compounds in *Dictyostelium* is likely to be regulated by cellular mechanisms controlling macropinocytosis, thus changes in fatty acid incorporation may be due to simple regulation of this process. To examine this, and since macropinocytosis is dependent upon actin polymerisation, the inventors used latrunculin (10 an inhibitor of actin polymerisation (de Oliveira and Mantovani, 1988), to observe the effects on fatty acid uptake. Inhibition of actin polymerisation decreased uptake in control cells. However, latrunculin failed to attenuate VPA-induced AA uptake suggesting VPA-induced fatty acid regulation was independent of vesicle dynamics (FIG. 6C).

Genetic Ablation of PLA₂ Activity does not Reverse Fatty Acid Perturbation

Figure 7:
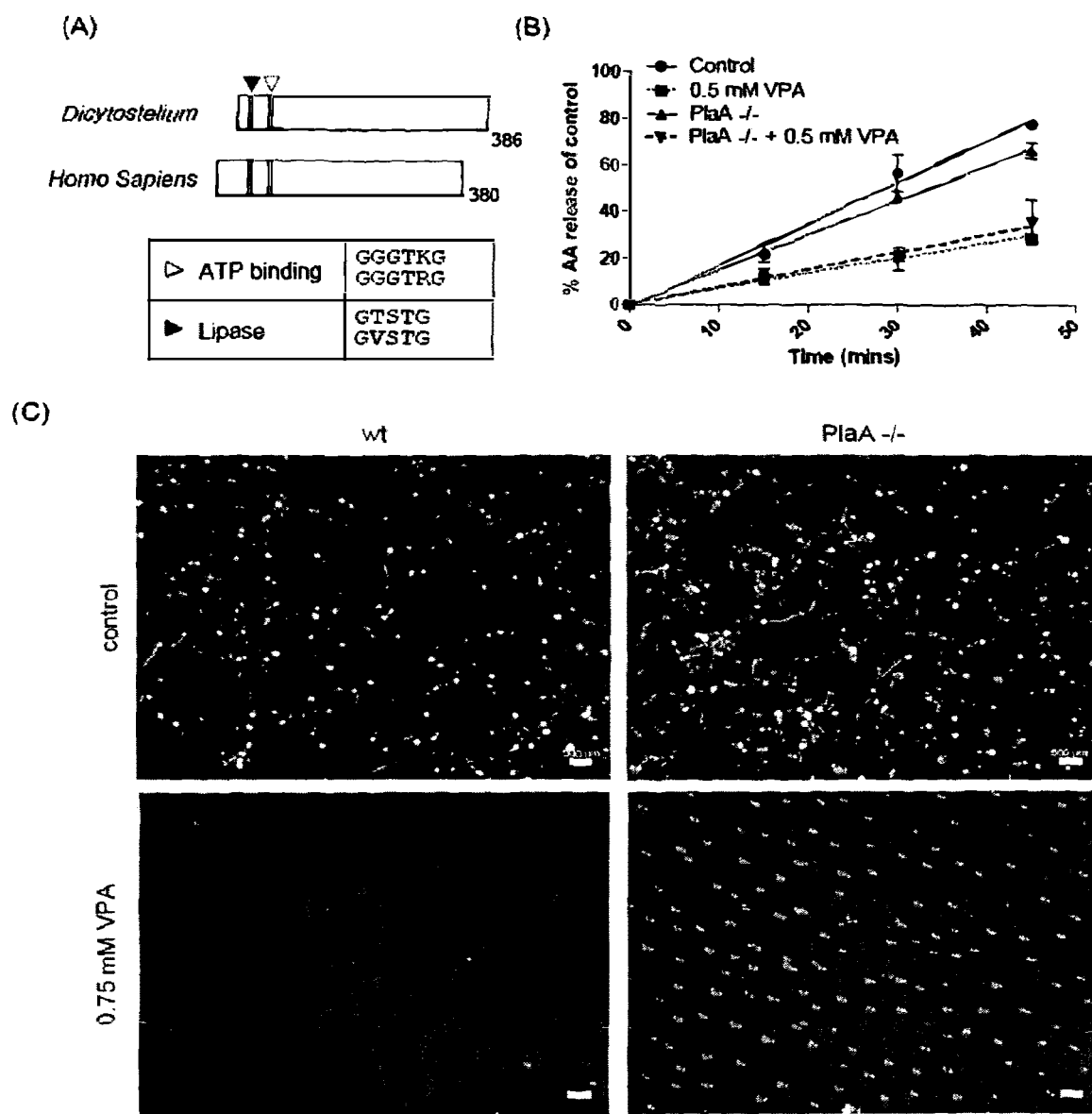
FIG. 7 demonstrates that knockout PIaA cells are protected from VPA-induced inhibition of development. (A) Alignment of PIaA protein sequence from Dictyostelium discoideum (XP_642421.1; SEQ ID NO: 10) and an $iPLA_2$ protein sequence from Homo sapiens (AAD08847; SEQ ID NO: 11). Sequences show conserved homology at ATP binding (SEQ ID NOS: 12-13) and lipase sites (SEQ ID NOS: 14-15).

To identify specific genes controlling the effect of VPA in this model, the inventors carried out a restriction enzyme mediated integration (REMI) mutant screen to identify loci controlling the effect of VPA during development (Kuspa and Loomis, 2006). VPA inhibits the development of Dictyostelium at concentrations found in plasma of patients receiving VPA treatment (0.28-0.7 mM; (Silva et al., 2008)) (FIG. 7B). One mutant isolated in this screen contained an ablated $PLA_2$ gene (SEQ ID NO: 16; van Haastert et al., 2007), with the encoded protein showing similarity to $Ca^{2+}$-independent enzymes, and containing conserved ATPase (SEQ ID NOS: 12-13) and lipase motifs (SEQ ID NOS: 14-15; FIG. 7A), and the mutant showed partial resistance to VPA during development (FIG. 7B). However, the knockout cell line did not attenuate radio-label release from cells (FIG. 7C) suggesting that although disruption of the $PLA_2$ gene (SEQ ID NO: 16) offered partial protection to VPA during development, it was not enough to prevent gross VPA-induced fatty acid release.

VPA Regulation of Fatty Acid Signalling is not Phenocopied by $PLA_2$ Inhibition Since VPA has been suggested to regulate phospholipase A2 ($PLA_2$) related signalling (Rao et al., 2008), and since ablation of a single $PLA_2$ gene (SEQ ID NO: 16) provided only partial resistance to VPA during development and no effect on gross radiolabel release or fatty acid uptake (FIG. 7), the inventors assessed the role of pharmacological inhibition of $PLA_2$ on AA regulation. Chemical inhibitors of different $PLA_2$ class specificity (BEL [80 µM], a $Ca^{2+}$-independent $PLA_2$ inhibitor (Ackermann et al., 1995); MAFP [50 µM], a $Ca^{2+}$-dependent and $Ca^{2+}$-independent cytosolic $PLA_2$ inhibitor (Balsinde and Dennis, 1996, Lio et al., 1996); and BPB [20 µM], a phospholipase A2 inhibitor (Mitchell et al., 1976) all reduced radiolabel release from ³H-AA cells in a similar manner to VPA treatment (FIG. 8). Differing specificity for these inhibitors was shown since a cocktail of all three inhibitors provided a cumulative inhibition of release. In contrast to the effect of VPA on release (causing an increase in fatty acid over time), chemical inhibition of $PLA_2$ activity caused a reduced uptake of fatty acid (FIG. 8). This data suggests that $PLA_2$ inhibition partially phenocopies the effect of VPA in modifying AA signalling, but that VPA has a more generalised effect on fatty acid signalling.

VPA-Induced Fatty Acid Uptake is not Dependent on Fatty Acid Activation

To test whether the incorporation of fatty acids was dependent on activation, the inventors firstly tested the ability of cell extracts to activate palmitic acid to form PaA-CoA. In these experiments, incubation of cell extracts with ³H-PaA and coenzyme A enabled the activation of the fatty acid that was subsequently separated by differential solvent solubility and quantified (von Lohneysen et al., 2003). Inclusion of VPA (1.0 mM) either with cell extracts during the activation assay, or by pre-treatment of cells prior to preparation of extracts (10 min, 1 mM) had no effect on fatty acid activation, whereas ablation of the peroxisomal fatty acid CoA synthase A enzyme (FcsA)—the enzyme responsible for fatty acid CoA activation in endosome-showed a significant reduction in PaA-CoA synthesis (FIG. 8) compared to wild-type cells. Furthermore, cell lines lacking fcsA (DDB G0269242; SEQ ID NO: 19 (von Lohneysen et al., 2003)) showed a VPA-induced increase in fatty acid uptake in a similar manner to wild type cells (FIG. 8). These results suggest that the effect of VPA in regulating fatty acid signalling is independent of fatty acid CoA activation as was previously suggested (Bazinet et al., 2006b).

Structural Specificity of Induced Fatty Acid Release

SAR studies identify the physical requirements for compounds to cause an effect, and these studies can help to distinguish between discrete effects of a compound. To examine the structural dependency of VPA on radiolabel release following ³H-AA incorporation, the inventors employed a range of compounds related to VPA with varying carbon backbone and side chain lengths, head group, enantiomeric specificity and saturation and measured release following 30 min 0.5 mM treatment. The results obtained are summarised in Table 3 below.

TABLE 3

| Compound | structure | AA release [% of control] |
| --- | --- | --- |
| Control | | 100 |
| VPA (2-propylpentanoic acid) | 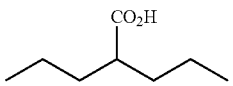 | 50 |

TABLE 3-continued

| Compound | structure | AA release [% of control] |
|---|---|---|
| 2-propyloctanoic acid | 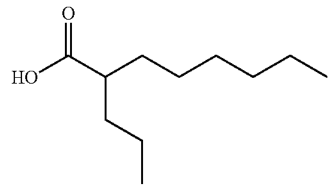 | 45 |
| 2-propyldecanoic acid | 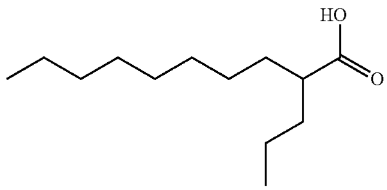 | 56 |
| decanoic acid | 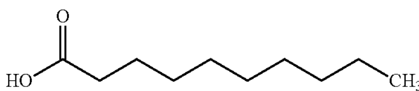 | 62 |
| 4-methylnonanoic acid | 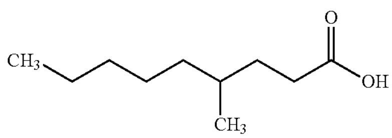 | 63 |
| nonanoic Acid | 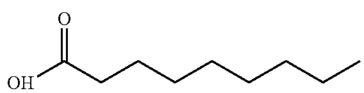 | 66 |
| 4-methyloctanoic acid | | 66 |
| octanoic acid | 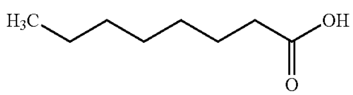 | 72 |
| 2-ethyldecanoic | 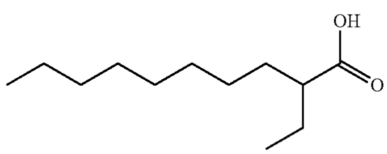 | 73 |
| 4-ethyloctanoic acid | 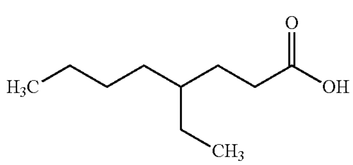 | 87 |
| dodecanoic acid | 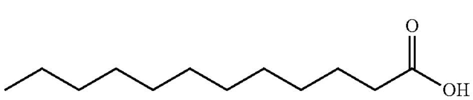 | 89 |

The compounds tested showed a range of inhibitory activity, with high structural specificity, and the strength of activity was independent of acidity and lipophilicity (pKA and logP values respectively).

Since VPA gave a reduction in activity to 50% of control, the inventors defined compounds, such as 2-propyloctanoic acid, as highly active since they reduce activity to 45% or below. These highly active compounds were carboxylic acids (since valpromide gave virtually no inhibition, data not shown) branched at the second carbon, with the most active compounds containing an isopropyl group. Unlike teratogenicity (Eickholt et al 2006), a tertiary-substituted C2 still showed activity, and long- and medium-length straight chain fatty acids were still active. Branched compounds were stronger than corresponding straight chains, with a preference for longer side chains (propyl-giving stronger inhibition that methyl-side chains). Finally, unsaturated compounds showed a reduction in inhibitory activity. This SAR study represents a novel description of a VPA-catalysed effect.

To confirm that the dual effects of attenuated fatty acid release and increased fatty acid uptake occur at a single site, the inventors analysed two compounds showing either strong or weak inhibitory effects on radiolabel release (isopropyl-pentanoic acid and 4-methyl octanoic acid, respectively) for effects on $^3$H-AA uptake (FIG. 9). From these experiments, enhanced inhibition of radiolabel release corresponded with an elevated uptake of fatty acid into cells as compared with VPA, and a reduced effect on release corresponded with a reduced effect on uptake. This data suggest a single, highly structurally-specific site of action for VPA and related compounds in the regulation of fatty acid signalling.

DISCUSSION

VPA is used to treat a number of current medical conditions including epilepsy, Bipolar disorders, and migraine and its role is likely to expand widely to include cancer (Blaheta et al., 2006), HIV and Alzheimer's (Qing et al. 2008) treatment (reviewed in Lagace et al., 2005, Terbach & Williams, 2009, Bialer & Yagen, 2007), ischemia (Costa et al. 2006), and fatal blood loss (Alam et al. 2009). Understanding how these conditions are controlled by VPA has proved highly complex since it triggers a variety of cellular changes with unknown primary targets and these changes have not been related to specific clinical conditions, and few structure-function studies have been carried out (reviewed in Lagace et al., 2005, Terbach & Williams, 2009, Bialer & Yagen, 2007, Nalivaeva et al., 2009).

Effect on Phosphoinositol Signalling

The inventors have shown that VPA causes a dose-dependent reduction in PIP and PIP$_2$ (FIGS. 1 a&b) in the biomedical model, *Dictyostelium*, and this provides one of the few effects of VPA found to occur in the acute time period shown to protect against induced seizures (FIG. 1b; Honack & Loscher, 1992). The vast majority of research into VPA mechanisms has been complicated by long term treatment leading to changes in gene expression (likely to be mediated by teratogenic effects (Gurvich et al., 2004, Phiel et al., 2001)) or in time periods enabling regulation of multiple indirect targets. Therefore a rapid attenuation of phosphoinositide signalling provides a significant insight into the acute function of VPA. In light of increased phosphoinositide levels during seizures (Van Rooijen et al., 1986), the results shown here provide an exciting breakthrough in our understanding of seizure control.

Figure 2:
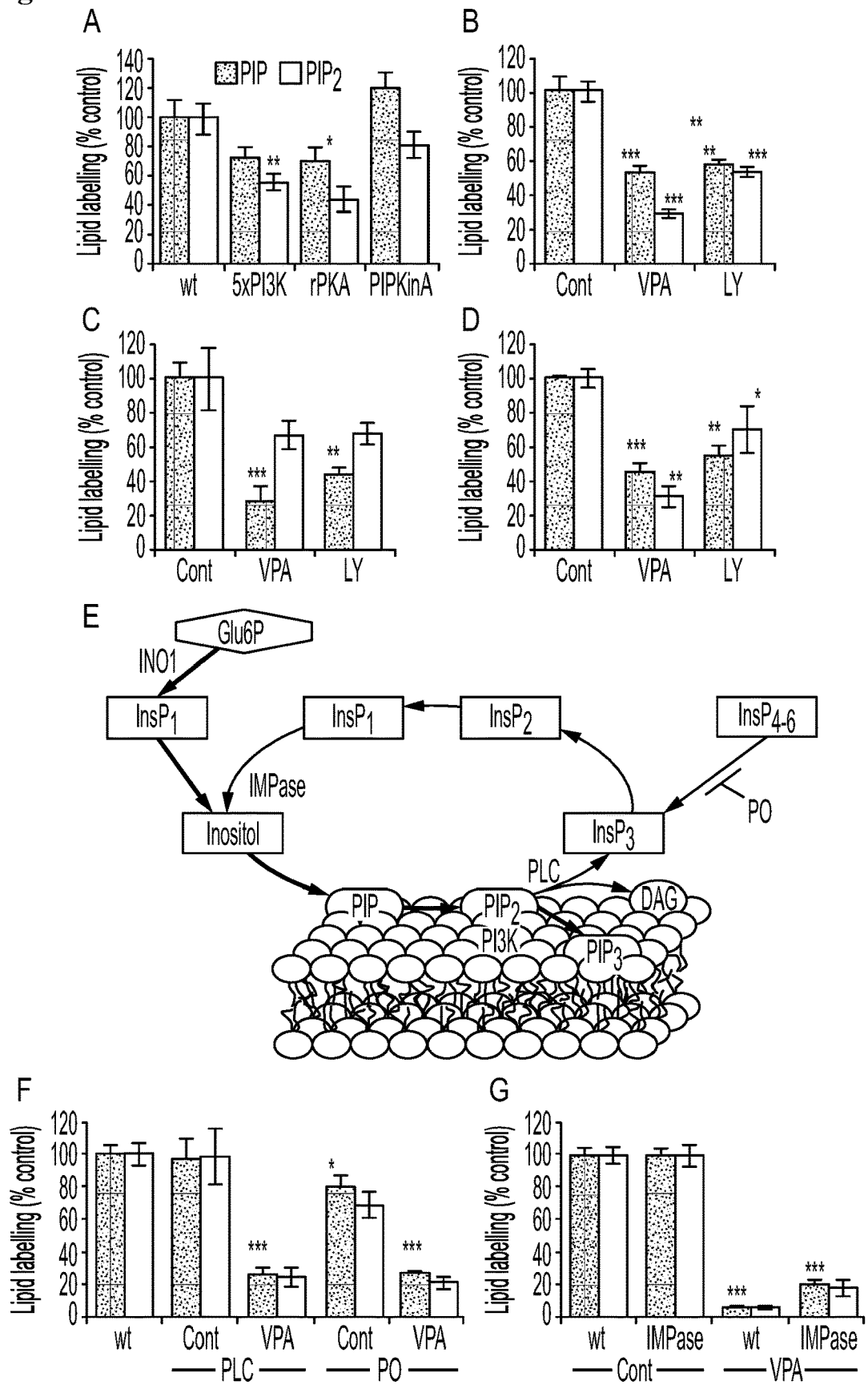
FIG. 2 shows phosphoinositide signalling and VPA sensitivity in wild type (wt) and knockout mutants lacking phospholipid kinase and inositol recycling enzymes with or without 9 min VPA treatment (0.5 mM). (a) Comparison of phosphoinositide levels in untreated isogenic mutant lines lacking indicated lipid kinase activities: five type 1 phosphatidylinositol 3-kinase (5xPI3K; DBS0252654) genes (SEQ ID NOS: 1-5); the phosphatidylinositol-4-phosphate 5-kinase (rPKA; DDB0191443) gene (SEQ ID NO: 6); and the phosphatidylinositol-4-phosphate 5-kinase gene (PIPKinA; DDB0185056) gene (SEQ ID NO: 7). VPA and PI3K inhibitor sensitivity was monitored using 0.5 mM VPA or 50 µM LY2946004 respectively for: (b) the 5xPI3K mutant; (c) the rPKA mutant and (d) the PIPKinA mutant. (e) Schematic of phosphoinositide signalling showing the role of phospholipase C (PLC), prolyl oligopeptidase (PO), inositol monophosphatase (IMPase) and myo-inositol synthase (INO1) in the generation and recycling of phosphoinositides. (f) Ablation of PLC (SEQ ID NO: 8) and PO (SEQ ID NO: 9) genes did not alter VPA-attenuated PIP and $PIP_2$ signalling (g) Extended VPA treatment (60 min, 0.5 mM) further reduced phosphoinositide signalling, and this effect was not reversed following overexpression of IMPase. Results are provided for triplicate experiments with duplicate samples±SD where *P<0.05; P<0.01; *P<0.001 for PIP levels.

It is very difficult to identify the target(s) of a drug which modulates phosphoinositide metabolism in vivo in mammalian systems, due to the large number of kinases' and phosphatases, and the promiscuous nature of lipid kinases substrate selection. An advantageous approach, facilitated in Dictyostelium, is to employ isogenic cell lines containing ablated kinase genes. Since it has previously been shown that VPA attenuates PIP3 production (Xu et al., 2007), the inventors analysed phosphoinositide turnover in cell lines lacking all type 1 PI3K activity (SEQ ID NOS: 1-5; Hoeller & Kay, 2007), and in two unrelated lipid kinases null mutants (a receptor-linked phosphatidylinositol 5 kinase (rPKA) (SEQ ID NO: 6; Bakthavatsalam et al., 2006); and a nuclear phosphatidylinositol 4/5 kinase activity (PIPKinA) (SEQ ID NO: 7; Guo et al., 2001; FIG. 2). All three mutant cell lines showed large and significant reductions in PIP turnover following VPA treatment, albeit at reduced levels compared to wild type cells, indicating that these enzymes cannot be the direct target of VPA in phosphoinositide attenuation and that testing of further kinases would be of little benefit.

The inositol depletion theory (Berridge et al., 1989) provides a well-supported theory for action of VPA in bipolar disorder phrophylaxis (Williams et al., 2002, Williams, 2005), potentially through the indirect inhibition of the enzyme responsible for de novo inositol biosynthesis, myo-inositol-1-phosphate synthase (MIP). A strong inhibitory effect on MIP activity has also been shown for a limited number of VPA congeners (Shaltiel et al., 2004; Shaltiel et al., 2007), suggesting inositol regulation may be related to seizure control. However, the newly discovered compounds showing strongly improved seizure control (e.g. 4-MO and nonanoic acid) do not acutely deplete inositol in the time frame for seizure control, arguing against a role for inositol signalling in this clinical treatment. Einat et al., 2008 also showed that pharmacological inhibition of MIP (through compounds structurally unrelated to VPA) does not control inositol sensitive pilocarpine-induced seizures model. Instead, the data shown here adds weight to the identification of phosphoinositide signalling as playing a key role of seizure occurrence (Backman et al., 2001) and suggests that VPA's effect on phosphoinositide turnover and seizure control is unrelated to that of inositol depletion.

The majority of research concerning VPA targets and clinical efficacy has centred around compounds with either a five carbon backbone (with a branch point on the second carbon) or cyclic derivatives (Bialer & Yagen, 2007). Thus the discovery of a novel family of compounds with longer carbon backbones showing inhibition of phosphoinositide turnover and seizure control provides a major advance in the development of new therapeutics. This novel chemical family includes compounds branched at the second and fourth carbon, suggesting efficacy in compounds with variable branching, and thus provide a new large family of compounds of potential clinical interest.

Here, the inventors tested the efficacy of five compounds within this novel family of fatty acid in an in vitro model of epileptiform activity that is a key model for screening potential antiepileptic drugs (Piredda et al., 1985). All compounds give rise to a greatly increased but reversible reduction in epileptiform activity in a PTZ model (see FIG. 3). This effect is not model specific, since one compound (4-methyloctanoic acid) shows efficacy in a low $Mg^{2+}$ model. However, efficacy in in vitro models does not necessarily imply efficacy in vivo, because other factors such as drug metabolism, brain penetration and access to the drug target play an important role. The inventors therefore tested 4-methyloctanoic acid further in an in vivo model of status epilepticus (FIG. 4), where it proved more potent than VPA. This model has been previously shown to be resistant to phenytoin and to respond only to high doses of other anticonvulsants (Chang et al., 2009). These results therefore suggest that this family of compounds may provide a novel seizure control agent with increased efficacy, and since they are predicted to not show teratogenicity, they may also provide reduced side effects compared to VPA treatment.

These findings identify a mechanism of action of VPA in attenuating phosphoinositide turnover in the simple biomedical model, *Dictyostelium*, and have shown that this effect occurs independently of a range of phosphoinositide kinase enzymes, inositol recycling and depletion. The inventors used this system to identify a novel family of compounds showing increased phosphoinositide attenuation. They then translated this simple model-based research to several clinical models of seizure control and show a large increase in efficacy for five of these compounds over VPA in a hippocampal slice model of epileptiform activity and for one of these compounds in a whole-animal model of status epilepticus. These studies thus suggest seizure control efficacy for a novel family of compounds with longer backbone length and variable side chain length and position compared to VPA. Continued analysis of the biosynthetic pathways controlling phosphoinositide signalling may give rise to significant advances in understanding epilepsy and other VPA-treatable disorders such as bipolar disorder and migraine.

Effect on Fatty Acid Turnover

Previous studies have suggested a possible mechanism of action of VPA is the attenuation of arachidonic acid turnover (Chang et al., 2001). Here the inventors have demonstrated in the model Dictyostelium discoideum that VPA significantly reduces the release of radiolabel following $^3$H-AA incorporation. Surprisingly, the inventors also observed that the uptake of $^3$H-AA was enhanced in the presence of VPA. Since arachidonic acid is not an endogenous fatty acid in Dictyostelium the inventors also verified these results with palmitic acid, a fatty acid found in Dictyostelium (Weeks, 1976). The similar results observed for both poly-unsaturated and saturated fatty acids suggest a common mechanism for the modulation of fatty acid metabolism by VPA. The similarity of these results shown here and those seen in in vivo animal studies, such as decreased AA turnover (Chang et al., 2001) and increased lipid accumulation (Kesterson et al., 1984) suggest that Dictyostelium may be a useful model in the study of VPA induced fatty acid dynamics.

Few studies of fatly acid regulation by VPA in animal models have examined a role for VPA in simply elevating fatty acid transport into cells. Thus, to examine this, and since uptake of extra-cellular nutrients in Dictyostelium is regulated by vesicle dynamics (macropinocytosis), the inventors showed that blocking vesicle function by inhibition action polymerisation did not inhibit the VPA-catalysed increase in fatty acid uptake. These results are supported by their previous results, since they have shown that VPA treatment also inhibits vesicle dynamics in Dictyostelium (Xu et al., 2007), and these results therefore point towards an effect of VPA in regulating fatty acid signalling which is independent of uptake.

Polyunsaturated fatty acid turnover is primarily regulated by $PLA_2$-catalysed cleavage from lipids to release free fatty acids, and VPA has previously been suggested to regulate $PLA_2$—dependent signalling (Rapoport and Bosetti, 2002). A role for $PLA_2$ in VPA-dependent signalling in our model was suggested when a screen for mutants resistant to the effect of VPA during development revealed that ablation of a single $PLA_2$ gene gave partial resistance to VPA. This provided an exciting link to a potential clinical function of VPA, since elevated levels of $PLA_2$ have been shown in bipolar disorder patients (Ross et al., 2006) and during seizures (Siesjo et al., 1982; Rintala et al., 1999a; Bazan et al., 2002; Basselin et al., 2003a). However, ablation of the single isoform of $PLA_2$ (SEQ ID NO: 16) identified in the genetic screen did not affect net change in VPA-induced radiolabel release (FIG. 8B). This may be due to the presence of 18 other $PLA_2$-like genes present in the genome (Fey et al., 2009), since the activities of these gene products are likely to hide small changes caused by single gene ablation in whole-cell assays. However, the identified gene may play a critical, targeted role in Dictyostelium chemotaxis and development—as has been shown (Chen et al., 2007, Kortholt and van Haastert, 2008), and thus partially overcome the VPA-related development effects. This VPA-dependent inhibition of development may not be visible in the assays employed here, since the assay does not differentiate between cell-type specific function nor do it explore multiple time points over development.

To further examine $PLA_2$ signalling in the observed effect of VPA, the inventors used pharmacological inhibitors of $PLA_2$ activity, and showed these reduced radiolabel release from $^3$H-AA labelled cells—thus confirming that VPA mimics the effect of $PLA_2$ inhibition in this model. However, this effect of VPA is not through direct $PLA_2$ inhibition, since the VPA-induced increase in fatty acid uptake was not reproduced by $PLA_2$ inhibitors (FIG. 9). This data, suggests that a $PLA_2$ inhibition-like effect of VPA may provide only one aspect of the drugs effect in regulating fatty acid turnover, and confirms that $PLA_2$ is not the primary target of VPA in this effect.

If $PLA_2$ is not the pharmacological target of VPA, the observed partial phenocopying of $PLA_2$ inhibitors may point to an upstream disruption in lipid metabolism. For example, a reduced activity of fatty acid acyl CoA synthases may cause a reduced incorporation of radio-labelled fatty acid into phospholipids, resulting in a reduced release of the radio-labelled fatty acid (thus resembling a $PLA_2$-inhibitory like effect). The inventors show that VPA does not inhibit CoA activation of fatty acids either directly or indirectly. Furthermore, genetic ablation of both of fatty acid CoA synthases (FcsA and FcsB) still showed VPA-dependent regulation of AA uptake, thus confirming that fatty acid activation is not the target of VPA in this effect, in contrast to that reported earlier at high VPA concentrations (Bazinet et al., 2006b).

Finally, the inventors have employed a SARs study to investigate VPA induced fatty acid regulation. This approach provides a highly important insight into VPA action, since VPA is used in the therapeutic treatment of a large range of conditions (Terbach and Williams, 2009), with numerous cellular effects remaining un-associated with each therapeutic role, and very few of these effects have an identified primary target (Lagace and Eisch, 2005, Terbach and Williams, 2009). SARs studies can be used to help differential these therapeutic treatments, mechanisms and targets. For example, range of VPA-related compound showing histone deacetylase inhibition as a cellular function have been shown to cause teratogenicity as a biomedical action, and the structural definition can now predict teratogenicity in novel compounds (Phiel et al., 2001). From the SARs study for fatty acid turnover, this effect is not related to teratogenicity since some compounds show strong fatty acid regulation but no predicted teratogenicity (Radatz et al., 1998). Another cellular effect of VPA in Dictyostelium and mammalian neurons is the inhibition of inositol based signalling (Williams et al., 2002, Eickholt et al., 2005, Shimshoni et al., 2007). Although some compounds (e.g. isopropyl-pentanoic acid) are strongly active in both inositol signalling attenuation and fatty acid regulation, these effects are not shared by all compounds, thus indicating these fatty acid- and inositol-based signalling effects are independent. Thus fatty acid regulation, HDAC inhibition and, inositol depletion provide three independent mechanisms of action for VPA. Employing VPA structures showing increased or decreased activity in fatty acid regulation may therefore give rise to increased therapeutic activity or a reduction in unwanted side effects in VPA-treatable conditions.

One clinical corollary of this work is shown in VPA-dependent lipid droplet formation. This effect has been shown in systems ranging from S. cerevisiae (Sun et al., 2007) to hippocampus and neocortex of the rat brain (Sobaniec-Lotowska, 2005), clearly indicating that the observed effects reported here are unlikely to be model specific. Furthermore, lipid droplet formation has also been associated with hepatotoxicity, although the mechanism remains unclear (Fujimura et al., 2009). The identification of a structural specificity for this effect in lipid regulation provides a potential mechanism for selection of novel therapeutics lacking this effect. The structural isolation of VPA-dependent increased lipid accumulation may also go some way to explaining the weight gain associated with patients undergoing VPA treatments (Wirrell, 2003, Masuccio et al., 2010, Verrotti et al., 2010).

In conclusion the inventors have described here a model for the study of VPA-induced fatty acid regulation. $PLA_2$ inhibition phenocopies some but not all of these VPA-dependent effects, but $PLA_2$ is unlikely to be the primary target of VPA. The role of this effect is likely to function in both bipolar disorder treatment and seizure control, since increased $PLA_2$ activity is implicated in both conditions (Yegin et al., 2002, Rao et al., 2007). Identifying novel structures for this effect, comprising carboxylic acids, branched on the $C_2$ position, with short (five carbon) to medium length (nine carbon) backbone and side chain (ethyl or propyl) provides potential new therapies for both conditions. The future definition of the primary site of action for this effect will significantly aid our understanding of VPA and related therapeutics.

All documents cited herein are hereby incorporated by reference in their entirety within this disclosure.

REFERENCES

Ackermann E J, Conde-Frieboes K, Dennis E A, *Journal of Biological Chemistry* 270, 445-450 (1995).
Alam et al. *Surgery* 146, 325-333 (2009)
Armand, V., Louvel, J., Pumain, R., & Heinemann, U. *Epilepsy Res.* 32, 345-355 (1998).
Backman, S. A. et al. *Nat. Genet.* 29, 396-403 (2001).
Bakthavatsalam, D., Meijer, H. J., Noegel, A. A., & Govers, F. *Trends Microbiol.* 14, 78-382 (2006).
Blaheta, Michaelis, Driever & Cinatl *Med. Res. Rev.* 25, 383-397 (2005). 3. Deubzer et al. *Leuk. Res.* 30, 1167-1175 (2006)
Balsinde J, Dennis E A, *Journal of Biological Chemistry* 271, 6758-6765 (1996).
Basselin M, Chang L, Bell J M, Rapoport S I, *Neuropsychopharmacology* 31, 1659-1674 (2005).
Basselin M, Chang L, Seemann R, Bell J M, Rapoport S I, *J. Neurochem.* 85, 1553-1562 (2003).
Bazan N G, Tu B, Rodriguez de Turco E B, Frog. *Brain. Res.* 135, 175-185 (2002).
Bazinet R P, Rao J S, Chang L, Rapoport S I, Lee H *J. Biol. Psychiatry* 59, 401-407 (2006a).
Bazinet R P, Weis M T, Rapoport S I, Rosenberger T A, Psychopharmacology (Berl) 184, 122-129 (2006b).
Berridge, M. J., Downes, C. P., & Hanley, M. R. *Cell* 59, 411-419 (1989).
Bialer, M. & White, H. S. *Nat Rev Drug Discov.* 9, 68-82 (2010).
Bialer, M. & Yagen, B. *Neurotherapeutics.* 4, 130-137 (2007).
Boeckeler K, Adley K, Xu X, Jenkins A, Jin T, Williams R S, *Eur. J. Cell Biol.* 85, 1047-1057 (2006).
Chang, P., Chandler, K. E., Williams, R. S & Walker, M. C. *Epilepsia* (2009). Chang M C, Contreras M A, Rosenberger T A, Rintala J J, Bell J M, Rapoport S I, *J. Neurochem.* 77, 796-803 (2001).
Chapman, A. G., Meldrum, B. S., & Mendes, E. *Life Sci.* 32, 2023-2031 (1983). Chen C T, Green J T, Orr S K, Bazinet R P Prostaglandins Leukot *Essent. Fatty Acids* 79, 85-91 (2008).
Chen L, Iijima M, Tang M, Landree M A, Huang Y E, Xiong Y, Iglesias P A, Devreotes P N, *Dev. Cell* 12, 603-614 (2007).
Chiu C C, Huang S Y, Su K P, Lu M L, Huang M C, Chen C C, Shen W W, *Eur. Neuropsychopharmacol* 13, 99-103 (2003).
Costa et al. *Stroke* 37, 1319-1326 (2006)
de Oliveira C A, Mantovani B, Life *Science* 43, 1825-1830 (1988).
Deutsch, J., Rapoport, S. I., & Rosenberger, T. A. *Neurochem. Res.* 28, 861-866 (2003).
Drancourt M, Bollet C, Carta A, Rousselier P, *Int. J Syst. Evol. Microbiol.* 51, 925-932 (2001).
Drayer, A. L., Van Der, K. J., Mayr, G. W., & Van Haastert, P. J. *EMBO J.* 13, 1601-1609 (1994).
DSMV IV American Psychiatric Association: *Diagnostic and statistical manual of mental* disorders (American Psychiatric Association, Washington D. C., 2000).
Eickholt B J, Towers G J, Ryves W J, Eikel D, Adley K, Ylinen L M, Chadborn N H, Harwood A J, Nau H, Williams R S, *Mol. Pharmacol.* 67, 1426-1433 (2005).
Eikel D, Lampen A, Nau H, *Chem. Res. Toxicol.* 19, 272-278 (2006).
Einat, H., Tian, F., Belmaker, R. H., & Frost, J. W. J. Neural Transco. 115, 55-58 (2008).
Eyal S, Yagen B, Shimshoni J, Bialer M, *Biochem. Pharmacol.* 69, 1501-1508 (2005).
Faix J, Kreppel L, Shaulsky G, Schleicher M, Kimmel A R, *Nucleic Acids Research* 32, e143 (2004).
Fey P, Gaudet P, Curk T, Zupan B, Just E M, Basu S, Merchant S N, Bushmanova Y A, Shaulsky G, Kibbe W A, Chisholm R L, *Nucleic Acids Research* 37, D515-519 (2009).
Fujimura H, Murakami N, Kurabe M, Toriumi W, *I Appl. Toxicol.* 29, 356-363 (2009).
Guo, Q. et al. *Nat. Med.* 5, 101-106 (1999).
Gurvich, N., Tsygankova, O. M., Meinkoth, J. L., & Klein, P. S. *Cancer Res.* 64, 1079-1086 (2004).
Hoeller, O. & Kay, R. R. *Curr. Biol.* 17, 813-817 (2007).
Honack, D. & Loscher, W. *Epilepsy Res.* 13, 215-221 (1992).
Holtkamp, M., Tong, X., & Walker, M. C. *Ann. Neurol.* 49, 260-263 (2001).
Isoherranen, N., Yagen, B., & Bialer, M. *Curr. Opin. Neurol.* 16, 203-211 (2003).
Johnson C. B., Wong E., & Birch E. J. *Lipids* 12: 340-347 (1977).
Kaufmann, D., Bialer, M., Shimshoni, J. A., Devor, M., & Yagen, B. *J. Med. Chem.* 52, 7236-7248 (2009).
Keane, P. E., Simiand, J., Mendes, E., Santucci, V., & Morre, M. Neuropharmacology 22, 875-879 (1983).
Kesterson J W, *Granneman G R, Machinist J M, Hepatology* 4, 1143-1152 (1984).
Kim H W, Rapoport S I, Rao J S, *Mot. Psychiatry* (2009).
King, J. S. et al. *Dis. Model. Mech.* 2, 306-312 (2009).
Kortholt A, van Haastert P *J, Cell Signal* 20, 1415-1422 (2008).
Kuspa A, Loomis W F, *Methods Mol. Biol.* 346, 15-30 (2006).
Lagace D C, Eisch A J, *Psychiatr. Clin. North Am.* 28, 399-414 (2005).

Lands W, Crawford C, New York: John Wiley & Sons (1976).
Lio Y C, Reynolds L J, Balsinde J, Dennis E A, *Biochim. Biophys. Acta.* 1302, 55-60 (1996).
Liu, M. J. & Pollack, G. M. P *Epilepsia* 35, 234-243 (1994).
Loscher, W., Fisher, J. E., Nau, H., & Honack, D. *J. Pharmacol. Exp. Ther.* 250, 1067-1078 (1989).
Loscher W, Nau H, *Neuropharmacology* 24, 427-435 (1985).
Maslanski, J. A. & Busa, W. B. Methods in Inositide Research (ed. Irvin, R. F.) 113-126 (Raven Press Ltd., New York, 1990).
Masuccio F, Verrotti A, Chiavaroli V, de Giorgis T, Giannini C, Chiarelli F, Mohn A, *J. Child Neurol.* (2010).
Meunier H, Carraz G, Neunier Y, Eymard P, Aimard M, Therapie 18, 435-438 (1963).
Mitchell S M, Poyser N L, Wilson N H, *Br. J. Pharmacol.* 58, 295P (1976).
Mora, A., Gonzalez-Polo, R. A., Fuentes, J. M., Soler, G., & Centeno, F. *Eur J. Biochem.* 266, 886-891 (1999).
Mora, A., Sabio, G., Alonso, J. C., Soler, G., & Centeno, F. *Bipolar Disord.* 4, 195-200 (2002).
Nalivaeva, N. N., Belyaev, N. D., & Turner, A. *J. Trends Pharmacol. Sci.* 30, 509-514 (2009).
Pawolleck, N. & Williams, R. S. *Methods Mol. Biol.* 571, 283-290 (2009).
Phiel, C. J. et al. 1 *Biol. Chem.* 276, 36734-36741 (2001).
Piredda, S., Yonekawa, W., Whittingham, T. S., & Kupferberg, H. J. *Epilepsia* 26, 167-174 (1985).
Qing et al. *J. Exp. Med.* 205, 2781-2789 (2008)
Radatz M, Ehlers K, Yagen B, Bialer M, Nau H, *Epilepsy Research* 30, 41-48 (1998).
Rao J S, Ertley R N, Rapoport S I, Bazinet R P, Lee H J, *J. Neurochem.* 102, 1918-1927 (2007).
Rao J S, Lee H J, Rapoport S I, Bazinet R P, *Mol. Psychiatry* 13, 585-596 (2008).
Rapoport S I, *J Nutr.* 138, 2515-2520 (2008a).
Rapoport S I, *Prostaglandins Leukot Essent. Fatty Acids* 79, 153-156 (2008b).
Rapoport S I, Bosetti F, *Arch. Gen. Psychiatry* 59, 592-596 (2002).
Rintala J, Seemann R, Chandrasekaran K, Rosenberger T A, Chang L, Contreras M A, Rapoport S I, Chang M C, *Neuroreport* 10, 3887-3890 (1999).
Ross B M, Hughes B, Kish S J, Warsh J J, *Bipolar Disord.* 8, 265-270 (2006).
Shaltiel, G., Mark, S Kofman, O., Belmaker, R. H., & Agam, G. *Pharmacol. Rep.* 59, 402-407 (2007a).
Shaltiel, G., Dalton, E. C., Belmaker, R. H., Harwood, A. J., & Agam, G. *Bipolar, Disord.* 9, 281-289 (2007b).
Shaltiel, G. et al. Valproate decreases inositol biosynthesis. *Biol. Psychiatry* 56, 868-874 (2004).
Shimshoni, J. A. et al. *Mol. Pharmacol.* 71, 884-892 (2007).
Siesjo B K, Ingvar M, Westerberg E, *J. Neurochem.* 39, 796-802 (1982).
Silva M F, Aires C C, Luis P B, Ruiter J P, Ijlst L, Duran M, Wanders R J, Tavares de Almeida I, *J. Inherit. Metab. Dis.* (2008).
Sobaniec-Lotowska M E, Int. *J. Exp. Pathol.* 86, 91-96 (2005).
Storey, N. M., O'Bryan, J. P., & Armstrong, D. L. *Curr. Biol.* 12, 27-33 (2002).
Sun Q, Bi L, Su X, Tsurugi K, Mitsui K, *FEBS Lett.* 581, 3991-3995 (2007).
Terbach N, Williams R S, *Biochem. Soc. Trans.* 37, 1126-1132 (2009).
Tokuoka, S. M., Saiardi, A., & Nurrish, S. J. *Mol. Biol. Cell* 19, 2241-2250 (2008).
Vaden, D. L., Ding, D., Peterson, B., & Greenberg, M. L. *J. Biol. Chem.* 276, 15466-15471 (2001).
van Haastert P J, Keizer-Gunnink I, Kortholt A, *J. Cell Biol.* 177, 809-816 (2007).
Van Rooijen, L. A., Vadnal, R., Dobard, P., & Bazan, N. G. *Biochem. Biophys. Res. Commun.* 136, 827-834 (1986).
Verrotti A, Manco R, Agostinelli S, Coppola G, Chiarelli F, *Epilepsia* 51, 268-273 (2010).
von Lohneysen K, Pawolleck N, Ruhling H, Maniak M, *Eur. J Cell Biol.* 82, 505-514 (2003).
Walker, M. C. et al. *Epilepsia* 40, 359-364 (1999).
Weeks G, Biochim. *Biophys. Acta.* 450, 21-32 (1976).
Williams, R. S. B. *Clinical Neuroscience Research* 4, 233-242 (2005).
Williams R S, Cheng L, Mudge A W, Harwood A J, *Nature* 417, 292-295 (2002).
Williams R S, Eames M, Ryves W J, Viggars J, Harwood A J, *EMBO J.* 18, 2734-2745 (1999).
Wilson D B, Prescott S M, Majerus P W (1982) Discovery of an arachidonoyl coenzyme A synthetase in human platelets. *J Boils Chem* 257: 3510-3515
Wirrell E C, *Pediatr, Neurol.* 28, 126-129 (2003).
Worsfold O, Toma C, Nishiya T, *Biosens. Bioelectron.* 19, 1505-1511 (2004).
Xu X, Muller-Taubenberger A, Adley K E, Pawolleck N, Lee V W, Wiedemann C, Sihra T S, Maniak M, Jin T, Williams R S, *Eukaryot. Cell* 6, 899-906 (2007).
Yedgar S, Cohen Y, Shoseyov D, *Biochim. Biophys. Acta.* 1761, 1373-1382 (2006).
Yegin A, Akbas S H, Ozben T, Korgun D K, *Acta. Neurol. Scand.* 106, 258-262 (2002).

The invention is claimed as follows:

1. A method for treating a seizure-related disorder in a subject in need thereof, the method comprising administering to the subject a therapeutically effective amount of 4-ethyloctanoic acid, wherein the therapeutically effective amount of the 4-ethyloctanoic acid is 1 to 20,000 µg/kg per dose.

2. The method according to claim 1, wherein the seizure-related disorder is epilepsy.

3. The method according to claim 1, wherein the therapeutically effective amount of the 4-ethyloctanoic acid is administered to the subject with one or more of a pharmaceutically acceptable carrier, a pharmaceutically acceptable adjuvant or a pharmaceutically acceptable vehicle.

4. The method according to claim 1, wherein the therapeutically effective amount of the 4-ethyloctanoic acid is administered to the subject orally.

5. The method according to claim 1, wherein the therapeutically effective amount of the 4-ethyloctanoic acid is administered in an orally acceptable dosage form selected from the group consisting of capsules, tablets, powders, granules, aqueous suspensions and solutions.

* * * * *

SEQUENCE LISTING

```
<160> NUMBER OF SEQ ID NOS: 19

<210> SEQ ID NO 1
<211> LENGTH: 4149
<212> TYPE: DNA
<213> ORGANISM: Dictyostelium discoideum

<400> SEQUENCE: 1
atgttattgg aagatgagga attaacatac caatcactat tggtttcaac tgaatcagat      60
gatgaaggtg atacaaacaa tcttttaagt attggtagtg ggggtgaaaa aacagctgtt     120
gaattggatt caatattttc attaagtcca caatcagcaa catcaccacc attatcacca     180
```

```
ccatcaccaa atccaacaag aactaaacca gctgtaccac cacgttcatt taattcacta    240
gatgagaatg aaaccttaac atttaaaaaa gaaccaattc taccaaaatc atcaaatgaa    300
tcattgttag gttcagtacc aaatgaacaa aaaaatgata aatcacccttt aaaatcaact    360 gaaccaacaa caatatcaac tgtacaacaa ccaattgttc aacaacaacc aattgttcaa    420
caacaaccaa ttgttcaaca acaattacaa caacaacaac aacaacaact gcaacagcaa    480
gaagttatgg aaccacaaca ttggtcaaat tatttatcaa tgaaaccatt aaaacaaacc    540
ttaaatgaaa taccaattca agttcaagtt aaagataatt attttataat gggatgtaat    600
aaaaatttta catcaagtga atttaaatca tatttagtat caaatttaga gagtatgatt    660
caagcgatta aagttggtac atttgcaacc aatgatatat catctgaaac cattgcattt    720
aaaaagaatg ctgtaatttg tgatttattc acagatagta ttcaacaaag accaacatca    780
ataccgagtt taattgtatt aaaacctggt atgcaagatt tattcaaagg taatagtcgt    840
gcatttattg gttcaccaat tgtaaatagt aataataatg ttaataataa tataaataat    900
agtaatagta atagtaataa taataatata aataatagtt tagatggttt taaattatca    960
acatcactac aaacaccatc agtaaattta agtttattac ataataatat tcaaaattta   1020
atatcaaata atggtaatag tggtcctagt agtattaata gtagttgtag tagtagtagt   1080
agtaacaatg gtaatacgac aaattatagt agtagtattg gtaatgaata taaacaacca   1140
atatcaggat cattgatatt taataataat aaaacattgg gtagaaatgc aaacttttca   1200
ttaggagaac aaagagataa taatgcaaaa ttaagacaac agaaaaagaa attaactgcc   1260
attcaaatta gttcattatt aggtgaacca ttgaattgga gtaatacaga gaatgaaatt   1320
aaatacttta gaaatttagc agaacaaatc tttgattttc aaacattgga tgaaagagat   1380
cgtgttaaaa ttacaattgc acctgtaacc aatgctcatc cagatccatt attaccaagt   1440
acttttagag ttaggtttta tttaccacca gataatcatt caactacaat caatgtaatg   1500
tcttctgata cagttacaaa tttaattgaa aaggttatag ccaaacataa taacagtaca   1560
aaattaattt catctgatca tacaccttct gattatgtaa ttcgtatcac tggtacatct   1620
gatcatgttt taaaaactga tgaattggtt acaaatttaa ttgtagttag aaatcgttta   1680
caacgtaaaa aagatattaa atttagcttg gtacataaaa cttcattacc aaaaatttat   1740
attgatggtc attcacctga aatttgtaca ttaaaaaaca ataataataa taataatata   1800
aataataata ataataataa taataataat aataataata taaataataa taatagtgaa   1860
aatggtaata ttcaacaacc atatggtagt ccaattaata ttttacaatt cccaatttca   1920
ccaagatcag aaaacaatgt aaatagtaat aataataata attataataa ttataataat   1980
aataataatt caaataaagg taataattca aatagatcaa ttttattata tgaaattaat   2040
agaccatttg aaattagaat aatttgttta gagaatttag ttttaccatt attccaaaaa   2100
tatttgggaa gcgaatgtaa taattttaat gatgtaaaat taacaattat ggtagaattg   2160
tgtcatggtg aagatgtttt aacagagcca atggagacag tgataaagtt aggatcaaat   2220
ccattatggt gtgaatggtt aagaagtgca ttattgatga gtaatatacc aagagcatca   2280
aagttatgtt ttcagcttta tgctcaacaa ggtgataaac aacaagccaa agtatccatt   2340
ggatgggcag atttacaatt gatcgattat catagtcaac ttttgagtgg agtgatctca   2400
ttaatcctat ggcctggagc acgtacagat ataccgatt taatgttcc ctcaccatca    2460 ttggtcattg aattctgtca attcccattc ccagtgtat tcccaaaacc agagatgatg    2520
gaacgtacag aaattagaga ttacgtagag tctcgtaaag aagatacaga aagattggaa    2580
```

-continued

```
gaattgattc gcaaagatag tttatacgtt ttgacagaga ctgataagaa attcatttgg      2640
ttatatagaa tgcatttaca aaagataccc tcttctttac caaaggtatt acaatcatta      2700
aattggaata atccacaaga agtaaaggaa gctcatcgtt tactttcaat tggtcaact       2760 ctatcaccat tggaagcatt ggaattattg gatagtaaat tcgcagatga attggttaga     2820
gagtatgctg taaattgttt acattcattg gccgatagtg aattggctct ttatctatta     2880
caattggttc aatcattaaa acatgaaccc tatcataata gtgcactatg tagattctta     2940
attcgtcgtg ctttaaataa tcgtgctgtc attggacatc cattcttttg gcatcttgaa     3000
gctgaaatgc ataatccaaa gatctctgaa cgttattcat tggttttgga aacttttta      3060 aaaggttgtg gtaatcaacg tcatgaattt gtaaaacaaa tggaagtggt cacaaaatta     3120
caaacaattg caaaactcgt caagaagca tcaccaaata aagaaagaa cctttacat        3180 gaagagttaa ataaaatgag ttggccaaat acttttcatt taccaatttc accatcaact     3240
gaaacctgtg gtgtcatagt tagtgaatgt cgttggttgg attctttcac tgtacctttg     3300
tatttggttt tccaaaatgt tgaccccgtt ggtgaaccaa tagcagtaat ctttaagaat     3360
ggtgatgatt tacgtcaaga tattcttaca cttcaaatga tctctgttat ggataatatt     3420
tggaaacaaa atggtctcga tcttcatctt tcaatctata acgttaccgc tatcaatgaa     3480
gatactggtt tcattgaagt tgttccagat tctgatacaa ctgcaaatat tcaaaaagct     3540
gctggtggtg tcactgctgc tttcactaaa actccacttt caaattggtt aagagaaaga     3600
aatcaatctg accccgacta tgaatatgca gttggtaatt tcactcactc tttagctggt     3660
tattgtgttg caacttttat tttaggtata tctgatagac ataatgataa tattatggtt     3720
tcaaaatctg gtcatttatt ccatattgat tttgcacatt tccttggaaa tattatgaaa     3780
ttccatggtt acaagagaga aaaagcacca tttgtattaa caccagaatt tgctcatgta     3840
atgggtggag aaaagagttt atcatttaaa ttcttctctg atttatgttg tttatcttat     3900 aaattttaa gaaatcatag aaatctattt attaatcttt ttagtttgat gatttcaaca     3960
ggtataccag agttatcaac aaaagcagat atttcatatt tgaaagaagc cttttatta     4020 gatgtgtcag atgaagaagc tggtgcatct tttgaaagat taattcaaaa gagttttaaaa   4080 acaaaaacta ctcaagttat gtttgcaatg catattttag ctcattcagg aacaagttct    4140
gatgattaa                                                             4149
```

<210> SEQ ID NO 2
<211> LENGTH: 5094
<212> TYPE: DNA
<213> ORGANISM: Dictyostelium discoideum

<400> SEQUENCE: 2

```
atgagacaaa ttgtcactgg tgtaattcac caaacaacac aatcacaaca ataccaaat       60 gtgataaact caaatcaaat tcaattttca aatgaaccaa tggttgttgg aagtattgag     120
gattttgata ttgactctga agttccacct cttgcaataa atttacaaag atcaataaat     180
aataataata ataataataa taataataat aataataata ataataataa taataataat     240
aataataata ataataataa tacccaacct tgcacaactg tattttaga tagagatagt      300 tgtgttaatg tcaaggcaac cattgattta ttaaaggaac aattagaatt tacgatcaag    360
gatttaatag atttcaaaga aaactatgat aaactagagt caacagaaca atttaagcaa    420
tggtctaatt taattaagaa tattaaagaa aactctttaa ataattcaaa tatttatttta   480 acaataccaa ctactcaaaa tttaattaat aataataata ataataataa taataataat    540
```

```
aataataata ataataataa taataataat aataataata ataacaatgt aataatacca    600
tcagcatcaa ctgaaaacaa agaagaaaat gataataata atagtaataa taataataat    660
attaatttat caccagatag ttcaatcacc aaagatataa atataactga aaataaaata    720
acggaaatta aaactacaga aactaaagaa acatctacag gaacttcacc attagaaaaa    780
tcaccatcaa aaggatttat aatttcacca aaaaaccag aagaagaaaa tgaaattgaa      840
ggtgaaacaa tcaataatat agcaataaca aactatacac agggtccatc aatgcttaca    900
ttaatgaaaa agaaacttga aaatattaaa aaaaataata acaataataa taataatggt    960
aatggtaata ataatagtaa taataataat agtaatagta ataataataa taatggtatt    1020
tcgccatcat cttcaccacc atcacacttg aatggtaata ataataataa taatagtaat    1080
aatacaaatt ctaataatac aacaaatgct acgaccaata gtgtaggatt ttcaataaca    1140
atgactaatt caaattcatt atcagtttca aagagaatga ataagtttaa atcatggaca    1200
tcatctaaac caacttcatc atctattgga tttgcttcat caccacaaaa taatggtaaa    1260
cctttaaata ttagtggttc aagtagattc tttacctcta gacaagattc aaaaattgat    1320
ttattaaaat caccatcaag ttcaccacca actcaatcag atatatttaa tgaaaataat    1380
aataataata ataataataa taataataat aataataata ataataataa taataataat    1440
aataataata ataataataa taataataat gaagaattaa taaataataa taataataat    1500
aataatgatg aaaattataa aattgaagaa acagaagaat cattaaaaga actattagag    1560
aaagagaaat tggagaatga agaaagagag aaaattttaa aagaaagaaa tgaaattgat    1620
aatttaaaaa agaaaaatca tttatcaaag ggatatttta tgagagcatg taatgcatcc    1680
aatgatgatg gattggagga agaggatata ccacttcaag atgaacattg ggaaaccaat    1740
gttatcgtgt tattaccatg tagacatcat gtaaaggtac caggttcatc gagtagttca    1800
attgattcaa ttagacaatt ggcatgggca agtggtaaaa tgcaaggtca tttaaattta    1860
gaaaaagatg agaaattctt tacactacgt tggtgtaata aagatgtggt attcgatcaa    1920
gatacgccat tgggtcattt aattcagtat aatttaaatt acaataatcc aacacagaaa    1980
ccaacaaata ttaaattgga attggtattg gaggatgaac tttgtaaaga gagattagtg    2040
gatttacaaa gtttagaaat taataatggt agaccaagca tttggaaatc tcatatcgat    2100
gatgtactaa gttcaatag aaaattacgc gagttggcaa tgttggcaaa accacaatca    2160
aatgtaccag ctgctcgttt aacaccttat ccaccaccaa aaacaattcc agaattcttt    2220
gtcattcgtg tacatctctt taaaaatcaa actaaatcac ttcgttgtgc taataatcat    2280
acagcattct ctttaatgac aattctatct gaaaaactta aaaatacaac acctttttgat    2340 ccaacacaat atcgtttctt aataactggt attaatcaat atgttgatcc taatgtacca    2400
ttattatcag ttgaatatat agttgaaaaa attaaaagaa aaggtgaaat tgatttaaca    2460
atggtagaat tattaagttt aggtttaatt atacaacaac agcaacaaca acaacaacaa    2520
caacaacaac aacaacaaca acaacaaata gaaaatattg atgatgaaaa tattttaaaa    2580
ttaaataatg gaatttttaaa tgttttatca aaaattgaaa aaccaattag agaaaaagat    2640
aattgtattt catcattaac agttacagag aatttacaag ttagattatt acatgctcat    2700 gaaattttg caagtaaagc atcagagata attggtacag attcaccaag tattcaatta    2760
tttattgagg cagcagttta ttttggtggt gaattattag caacacaaag tagtaaattg    2820 gttagttttcc aagatacagt ggtttggaat gaatgggtta atattccatt agcagtttca    2880
aatattccaa atggtgctag aatgtgttta ggtttaaatg ctagatatag aggtgacatt    2940
```

```
tttaatattg gttgggttgg tcatcgttta ttcgattcaa aaggtatact aaatactttt   3000
gcaccattct ctctattatt atggccaggt aaaattaatc caattggaac ttgtgtcgat   3060
aatttagaga gtaaagatca agcgattatc attgcattcg aatttaaaga ttatgttgta   3120
ccaaaaacaa ttcactatga agatgattta atagagttaa ttagtaaaga cgagaatggc   3180
aatgaattac cagtggttac aatggaggaa atggatagag tcgagcaaat tatattacaa   3240
gatccactct attcattgaa taagaagag agattgttaa tttggaaatc aagatacttt   3300
tgtcatacga aaccacaagc attatcaaaa ctttttacaat cagtagaatg gacaaattat   3360
aaacaagttg gtgaagcttt tcaattatta aaaatttggc caactttatc ggcagtcgat   3420
gctttagagt tattggatcc aaagtttgca gattgtgttg aaattagaga atacgccgtt   3480
aaatgtttag atcaaatgtc tgattatgaa ttggagattt atatgcttca attggtacaa   3540
gctattaaac atgatgtttt tcataactct gtattaagtt tattcttaat tggtagagtt   3600
tggcaaaata tgcaggtttt aggtcaccca ttcttttggc atttacgtgc tgatatcgat   3660
aatcaagagg tttgtgaaag atttagagtg ttatcatctg gttcttacg ttatgcacca   3720 actcaattaa tggaatcatt taaacgtgaa attacaaccc ttagaatttt agagaattta   3780
gctaaacgtg ttaaagaagt accttatgaa agagaaaaac aatatgttga aaataattta   3840
cgtgaagagc aatcatttcc aaccgaatta tttgtaccat ttgatccttc aattcggatt   3900
ttaaatatta ttccagagaa atgtaaatca atggattcag caaaggtacc actttgggta   3960
acatttaaaa atgctgatcc ttttgcacca ccattacaaa tgatagcaaa gactggtgat   4020
gatcttagac aagatattct aacattacaa ttgttgcgtc taatggatca tatgtggaaa   4080
tcacaagatt tagatttaca tatgaccatt tatcgttgta ttgcaactgg tatgggtact   4140
ggcttaattg aagtggttcc aaattcagaa actgccgcta gaatccaagc tggtgctggt   4200
ggtgtatctg gtgctttcaa acaaacaccc attgcaaatt ggttgaaaaa tcataatcaa   4260
actgaaaata gttatcaaaa agcagtttca aaattcacat tatcttgtgc tggttattgt   4320
gttgcaactt atgtttttggg tattggtgat agacataatg ataatattat ggtagatatt   4380
catgcacacc ttttccatat cgattttggt catttccttg gtaatttcaa acatttgca   4440 ggatttcaac gtgaaaaagc tccattcgtt ttaactcctg atttcgttta tgtaattggt   4500
ggtaaagatt ctccaaattt cgctttcttt gttgatattt gttgtaaagc tttcaatata   4560
attagaagta atgctcatgt ttttataaat atgtttgaat tgatgttatc cacaggtatt   4620
ccagaactta gaagtgaaaa tgatattgtt tatttacgtg ataaattag attagatctt   4680 acagatgcag aagcttcaga atactttaaa aaacttattc atgaatcaat aggtacatta   4740
acaactacaa ttaattttgc aattcatatt atggcacatc gtaaaaattt agtttctggt   4800
aattcagcac ctaaaattgg aagtgcaagt agtttaaatt taaataaaaa taaaccatca   4860 tcacaaaagta aattagattt aagtagatca gatttaagta gatcagattc aagtagatca   4920
gattcaagta gacttgactt aagtagatca gacaaaaaaa ataataagga taataaagaa   4980 aagaaaaag aaaagaaaaa agaaaaagaa aagaaaata atgataataa cgacaaggat   5040
aataataata atagtaataa tgcacacagag aaagaaaata gtatagataa atag         5094

<210> SEQ ID NO 3
<211> LENGTH: 4716
<212> TYPE: DNA
<213> ORGANISM: Dictyostelium discoideum
```

-continued

```
<400> SEQUENCE: 3
atgaatagta ttgaaagttc ttctaatgat agcaatgaga taaataaaaa ttcaaacaaa        60
aataatacac acttaaactc caactataat aatatttata aaaataatag cactagtagt       120
aataataata ataatcataa taatattgaa attattggga tagataataa taaaaataat       180
aataaaaata ataacgataa taataataat aataataata tagataaaaa agaaaggat        240 agtaaaaata aacaaaacca agaaataaat caagaaatgt cagaaaataa aaaaatttat       300
aatagtaatg atagtaattg tagtagtggt agtagtagtg gaggacatgt aaataatggt       360
catcatatat taattgaaga gaatgaaaga ttagaacatg aaaatcaaga gattcaagaa       420
atttataaac aaaagggtat ggaatttcaa aaaaagatt taagatttgg atatgatgtt       480
aatagtaata ataataataa taatggtggt ggtagtagca gtggtagtag cagtggtggt       540
agtgatgaat ctgcttcaaa tcaacctata attgaacta gaaatagaga aggttcaatt       600
ttaaatttaa agaacaagg tcttgtaaaa gaaattagtc aaagatttca aacaccagat       660
acagcatcat atacaagacc aaatgcaat aatatttcaa ttaaagataa aatttctata       720
ttaaaaaagg agcaagaaag aagaaaacaa gattcagaag tacaacaacg agaaaaggtt       780
atagtattat cagcagatag ttcaaatatt caaatttatc atccctctgt tttaatagaa       840
aaaatgaata gtaaattgga taccgaagaa aagccagcaa caacgacaac aactactact       900
acaacatcaa catcaatatc aacatcaaca ccaacaacta ctactactac tacaactaat       960
acttctacta ctaatgatat tacaattaaa ccaaaaacat caccaacaaa aaataatgaa      1020
gaaagatcac aatcaccaat tacaacacca aaacaaccag ttgaagaaat tgttaaaaaa      1080
gtatcaacac caaaatcaaa taatacttct aaaaagacat catccgatac aacaccaaca      1140
ggaaaaacaa ctaaaaaaga taaaaaagat aaaaaagata atcaagaga tagtggtaat       1200 ttagtaattg ttaataatac taataatact agtagtaata ataacaataa taataataat      1260
aataataata atgaaacaat tataaaaacgt agaggtagag ttttagttac accatcaagt      1320
gatttaaaaa agaatattca aatttatttt acaattccaa taaatccacc agtaaataaa      1380
accaataaac caaatcaatt attatcaaat acatcacaac aatttttaaa aacattaatt      1440
tcaaatgaaa ttccaatcga ttgtaaaatc aatgatatca acgatactga tgcatttttcc      1500 gatttatcag catcagcatc atcatcatca tttataacaa aatcatcaca atcattatta      1560
aatgtgcaat cattaagagt taaagcaatt aaaacatcat ttaatatttt attttttaatg      1620 ccaaatcaat ctaaaaagat tttacaagtt aaaggttcag atacaattga aaatttaaaa      1680
gaaagaataa tttcagatta tttatttaat aataatagta ataataataa taataattgt      1740
aaatatggag cagattctta tttaatatta gattttaatg ataatccaat ggaaagaagt      1800
ttagtattga ataaaagtga ttatatatta gataaaagag cacaaggttt aataccaaaa      1860
ttaaaagtta ttgaaaaatc aacaatttta gattcagatc catctgatga attatcacca      1920
agtgaatatg aaattattag aaaattaata ccaggtacag atacatggag aggtgaagaa      1980
gttgaatact ttagaagagt tacaagtaga ttaagatatg aagcattacc attgattaaa      2040
ggatcaattc agtctactct attggttaga ttatcaccat taccaatacc aatagttggt      2100
aataaaatat tgatttctat attttttacca attactcaag ttactaaaac attggatttg      2160
gaattgaatg aaactgccga tcaatttaca aatagattat ttacaaaaaa ttattcaaaa      2220
catttaccaa atgtaaattc aaatgatttc atattaaaag tagttggtag ttcagatttt      2280
attcatggtc cacatgatat tcgtactttt gaatcaatta gaaatcatat aattcaaggt      2340
```

-continued

```
acaaaaccac aattaacatt aattcaaaga ccaaaaccag aattagatcc acaaccattt    2400
aaaccacgtt ttgattatcc accagaatta ataattgatc atagttgtag taatgcaatt    2460
aattgtaata ataataatac aaatagtaca aataataata atataaattt tgataattgg    2520
gatcaaatta cacatatttc tattagagaa attaaaaaac catttagagt taaagttatg    2580
ggatcaacta gaataccatt atcatgtatt aaagatattg atagtagtag tgttattgtt    2640
tcaatttcat tatatcatgg tattgaatgt ttttcaaaag cattcactca accaattata    2700
ccaccaccat ttgcattttt agctgaaact ttatcagttg attggtgtga atggttagtt    2760
tttacaaata ttgattattc aaatttacca gtggatgcac gtttatcaat tagtgtctat    2820
agtgcaaatg aaacagttga tgatgttgaa gaaattaaaa atcttgatga agcaactaaa    2880
aagttaacac caattggttg gattaatgtt atgattactg atttttaaaata tcaacttaga    2940
caaggtatgg tagaattatc gttatggcca tctgattttt caaatccact tggtacttgc    3000
tcaaataatc catcaagtag tcaatcagtt ggtttaacat tagaatttga agaatttaat    3060
ttaccagttt tattcccaag aaaaactaaa ttctctacaa gtgtctcagt tattgaacaa    3120
ccaccaacca atataaattc aaatgaaatg agagaattct ttgagcaaat tacagcatta    3180
gacccattat cagatttaaa acaagagaaa tataatcaac tttggacttt aagacattat    3240
tcaatttat tcccacaagt tttaccaaga ttaatgttaa gtgtaccatg gactcaagca    3300
actgcagtag atgaagcaat ttcattactt gatagatggc caaaacttaa accttatgaa    3360
tcattggaat tattggatgc aaaacatgca aatagaaaag ttagagaatt tgcagttaca    3420
tgtttagagg atcttagtga agatgaacta ttagatattc tattacaatt agtacaggtt    3480
ttaaaatatg aaccattcca tgattcaaaa ttatcaagat tcttattaag aaaagcaatt    3540
ttaaatagaa atattggtca ttcattcttt tggtatttaa aatcagattt acatgatagt    3600
aatttatcag aaagatttgg tatactttg gaatcttatt tgtatgcatg tggtgcacat    3660
agaattgagt tattaaaaca aatggaagtt attaataatt taacagaggt tgcaaagaaa    3720
attaaaccat taaagatca agatagaaga gaatttatga ttaaagaatt tgaaagttta    3780
gaatggccaa aacgatttca tcttacttta aatccacgtt ttgaatcaaa tggttaata    3840
attaataaat caaaatatat ggatagtaaa aagttacctc taagattatc ttttacaaat    3900
accgatatga acgctgaccc tattgaagtg attttcaaag ctggtgatga tttaagacaa    3960
gatatgttaa ctttacaaat gattagatta atggataagt tatggcaaaa agaaggttta    4020
gatttaaaat tatctcccta tggctgtatt tcaactggtg atatgattgg tatgattgaa    4080
gtggtgttaa attctgaaac cactgctaaa attcaaaaaa gtgaaggtgg tggcgctgct    4140
tccgctttca agtggatcc tttggccaat tggatattgc aacataataa aagtgatatg    4200
gaatatcaaa aagctgtaga cacattcata ctctcttgtg ctggttattg tgttgcaact    4260
tatgtacttg gaattggtga tagacataat gataatttaa tggttacaaa aggtggtaga    4320
ttatttcata ttgatttcgg tcatttcctt ggtaattata aaaagaaatt tggtttcaaa    4380
agagaacgtg ctcctttttgt tttcactcct gattttttgtt atgtaatggg tggtaaagaa    4440
tcttttaaat ttagtcagtt tgtaaattat tgttgtaccg cttataatat cgttagaaag    4500
aatgctaaat tatttatgaa tttattcgct atgatggttt ctactggtat tccagaatta    4560
caatctatgg aagatttaaa ttatttaaaa gaatcttttt caatagaatt atctgatgaa    4620
aaagcaaggg agaaatttgt tgctttaatt catgaaagtt tagctacaaa aactactcaa    4680
cttaataatt tttttcatca tcttgcacat gcttag                             4716
```

<210> SEQ ID NO 4
<211> LENGTH: 5016
<212> TYPE: DNA
<213> ORGANISM: Dictyostelium discoideum

<400> SEQUENCE: 4

| | | | | | |
|---|---|---|---|---|---|
| atgaacgata | acaataataa | ttataccaat | aatgaagaaa | ttattaatca | acttaaatcc | 60 |
| aaaaaccaag | aaactgaaac | taaaatttta | aaactctata | atgccgtaaa | aattgacaaa | 120 |
| attaaaagaa | acaagaatt | tgaaatatt | gaagaacaaa | atagaaaatt | atcaattcaa | 180 |
| atcattgatt | taaataataa | aattgaagta | acaaataatt | caaatgaaaa | agagattgaa | 240 |
| ttattaagaa | atcaaattca | aaaagaaaaa | gataaatttg | aaaatgggtt | aataaaaagt | 300 |
| aaagaatttg | aaaagtctta | taattcaagt | tcaccattaa | acaattcaca | atcatttaga | 360 |
| caattaaaag | aatttgaaat | taattgtcac | catttagaaa | ctaaacttaa | tgattcatca | 420 |
| attattaatt | caagtaaaac | caatcattta | aatcaattaa | taacttcaac | tgaatcaaaa | 480 |
| attgaaaatc | ataataaaat | attacaagaa | aaagaaagaa | ttaaaaataa | taaaattgaa | 540 |
| tatgaattat | tattagaaga | gttagataaa | attaataaaa | gtgtaaattt | aacgaatagt | 600 |
| ggaccaaata | gtatgtacat | tacaatattg | gataatgaaa | ttatgaataa | tttagtaatc | 660 |
| tctttagaaa | ataatattaa | aactttaaaa | tcaccaaatt | catcaacaac | ttcattcatt | 720 |
| agtagtaatg | gtggtagtag | caatggtggt | agttcaatca | ttagtagtaa | tggttcatca | 780 |
| gatagtagtt | taagttttga | aaatttatca | aaattattaa | ttaaacaaag | ttcattcgat | 840 |
| agtaataatt | tacataaaaa | gaaagaaact | aatgaattac | aacaacaaca | acaacaacaa | 900 |
| caacaacaac | aacaacaaca | caacaacaa | caacaacaac | aacaacaaat | agaaacaaca | 960 |
| gcaacaacaa | caacagtatt | gttaacagca | gaagaagaat | ttaataaaaa | gattgaatca | 1020 |
| atacaaatta | acaaaaaga | gaggaaaatg | aaaattaaag | agagtttatc | aaattcgaat | 1080 |
| aataatttac | caattttgc | atttgaaaat | tcaattaggt | atccgataaa | tattattaca | 1140 |
| ccaacgataa | cgtaccagtt | aagttatagt | ttagaatttg | atactattca | aagtttatca | 1200 |
| aataaaattt | atcaacatat | tgattcaatt | gatgcagtga | tttaaaaag | gttaagaatc | 1260 |
| tactcaatgg | aacaattaat | tttaaaaact | tcatcaaatt | attattttca | agcggtatca | 1320 |
| caaaatcaac | aaccttaaa | atatataccc | tacttttcaa | atataaataa | aaatcagtca | 1380 |
| attgatttat | atatagttc | aaatttgtt | gaagatgaat | ttaatactca | aatgtcaacg | 1440 |
| attttaggaa | acgatttatt | attagagaat | aatagatcaa | ctgaagaatc | aattagtttt | 1500 |
| agaaataaaa | tgattaaatt | tttagatcaa | gttaaatctc | atcaaattca | attagataat | 1560 |
| gaaacaactt | tattacaatc | atcatcatca | acaacaacaa | caacaccaac | aataacaaca | 1620 |
| ccaccaaaca | tacttggtaa | taatatatca | ccttttttcat | caccaccaac | ttcaccaaat | 1680 |
| tcttcaatgt | catcattacc | ttcttttaaaa | tcatcaactt | ctcaacttc | tttaataatt | 1740 |
| ggtaattctc | gtccactatc | acaagttgt | aatagtttaa | ataatttaca | agataataac | 1800 |
| aataataata | ataataataa | taataatagt | ataacaaata | gtaaatcatc | atcatcaaat | 1860 |
| aatttattta | aatcatttt | aaaatcaaat | gcaattaata | ttgcaatgaa | taataataat | 1920 |
| agtagtaata | ataataatga | agaatttgaa | cagtttattg | gtaatagttg | gaaatcatgt | 1980 |
| tcaccatcat | catcatcatt | aaataaaaga | ttattaatgt | ttagtccatc | aacatcacca | 2040 |
| atgtcatcat | tgtcatcatc | accaatgtca | tcatcaccat | caacatcaat | gatatcatta | 2100 |
| ccaaattta | tgatattaaa | acaaaaatca | ataaataatt | taaatttaag | ttcaaattgg | 2160 |

```
tcattgacag aatcaaattg tacaattaga ttatatatta caaagaatat aattaaaaca   2220
tttgtttgta gtattcaaag tacaattggt gaattaaaag aattgatatt taaaaagttt   2280
caaaaaataa tcgaatctga gcatcacgaa attcaatcga ataaattttt aattaaaatt   2340
cgtggtcttg aaatttattt aacaaatcaa caatctcaat tatcttcaat tggttatata   2400
aattcaaaat ctagaagaca aagaaaaatt gatttattat tgatttttaat taatcaattt  2460 aatatgattg aaataaataa atttcaattg gattcatatg attttcaatt taatcaacaa   2520
cttgaaaaga atattttctt tgaccaacaa ttgaatgaga atatattccc atcgaatcta   2580
tcatatgggt gtggtaaaaa ttttaaaatt agaattggta gtttaaaaaa tttcgatatt   2640
tcaagaattg gtaaacttta tggtataaag aatacaagtt cttctaaaat ctatgtttta   2700
gcacaaattt atcaaggtga attttataaa attcaaatg aaatgcaaac tccgaaatta    2760
ccattatcaa gcaatccaag ttggttatgt accttggaag gtccatcatt caatcaaatt   2820
ccatcaaatg caatcatttc tttaaaagtt ttaattaatg atacaatcat tggttggata   2880
aattatcata tttggaatta taaaaataaa ttaaatactg gttttatgaa tttaaaatta   2940
tggtcaaatg ataaaatttt taatccaact tatttacata gaaattattt taataaaaat   3000
aaaaatcaaa atcaaaataa taataataat tttacaaatt ataatgaaag taatgaagat   3060
gattttgaaa cgttaatgct atcatttgaa attgatttat cattacaatc aatttacttc   3120
tcaccagaac cattagataa tcatcaatta caaatacttg aagaaaagta tttcatgtca   3180
acaatgtcaa caccagattc aaatcaaaat cagttaatta taaattcaat tttgaaaaag   3240
gatgtattaa cagatttaaa aaaagaagaa aaagaattaa tttggaagaa tagaaaattat  3300 tgtaaaaatc aaatgaataa ttcaattca aaattaattt tatctgtgcc ttggaatgat    3360
agtgaatcag ttcaagagtt ttattggtta ttaatgaatt gtccacaatt tgaaaatcca   3420
attgatagtt tagaattatt aagtcaatca ttcctagata gacaagttag aaattttgca   3480
attcaaaatc tttgtaaaat gaatgatgat gatatcacta tgtatcttcc acaattaatt   3540
caagcaatta acatgaacc acatcattat tcaatacttt caaaattcct aattcgtcgt   3600
gttttattaa ataaacaaaa tatggctcat attttctttt ggcaaattaa agctgaaatt   3660
ttaactttaa aaaatggtat taatccaaat gaaattaatg ataataataa taatattgat   3720
aataatggtg ataataataa taataataat aataataata ataataataa taataataat   3780
tataataatg ataatgataa tgataattat attacaaata attcagaatt taataataat   3840
aataataatt cagtaattca atatccacaa tggttagaaa ggtatcaatt aattttagaa   3900 attttttttaa gaggttgtag tgatgaaaaa ttattagaaa tttataaaca atatcaaatg   3960
tatagtaaaa ttaaacaagt tgcacttggt gtaaaaaatg taccaaataa taaaagaaaa   4020
gattatttaa ttcaagtttt aggtggtggt ggtagtaatg gtggtaatgg taataatgat   4080
ttattaaatt atcaagaaga ttttaaaaca ccaattaatc cagaatttag aggtaaaaga   4140
attgatgtta atggttgtaa agttaaagaa tcaaaaactt taccattatt tttatcaatt   4200
gaaaattatg atccgatggg tgataatagt tttgtgattt ttaaagctgg tgatgattta   4260
agacaagatc aattagttat tcaaatgatt aatattatgg ataagatgtg gttggatgat   4320
ggtatagatt tacaaactat tacttataga tgtattgcaa cgggtccaat ggagggtatg   4380
attgaggttg ttggtgactc aattacaatt gcagagattc aaaaacaaca aggtggtatc   4440
actgctgcat tctcagagac tgtgatctct caatggttaa aacaagagaa cccatcagaa   4500
ttggagtata gtaatgccgt tgaaaatttc attagatctt gtgctggttg ttgtgtttat   4560
```

```
tcttatatat tgggtattgg tgatagacat aatgacaata ttatgatcac aaaatctggc    4620
catctatttc atattgatca tggtagattc ttgggaaatg ttcaaacttg gaatggaata    4680
aaaagagaga gggctcccct tgtattcacc aatgcatttg caaatgtaat tggtggtgaa    4740
aacaatttca aaaatttcga agacctatgt tcaagagctt acaatacaat tagaaaacat    4800
gcaaatgtca tcctcaacct tttcctaatg atggttggtg gtggtttacc agaattaagt    4860
aaaaaatctg atatctatta tcttcgtgat gctttagctt tagatctaac aaatgaacaa    4920
gctgcaatta aattctcaaa tatgattcaa gaatctttag tttcaagatc aactgattta    4980
aattttgctg ttcatatttt agcaaatcca aattaa                              5016
```

```
<210> SEQ ID NO 5
<211> LENGTH: 5574
<212> TYPE: DNA
<213> ORGANISM: Dictyostelium discoideum

<400> SEQUENCE: 5
atgaaaatga gtgaaggaat tatatcacca ttatcacttt ctagtgaatc atcagagcaa      60
caacaggcag caattagaaa gtttagtaat ggtagtaatg gtagtggtgg tggtggtggt     120
agtaacctca gtgtaaatag tagtaatagt ggtagtaata atagtataag aaaaagttca     180
acattgatgt acaatggacc attaccatca ataaatgatg gtaaagaatt attattggaa     240
aactcgaaac caaagttgt agaattagta aatacattta tcataaaacc attatcaacc     300
attcattcag tacataatga ataccacca ccagcaattg aaaaagagaa aaagaaatc      360 ataaatacta tatcaaattc tggtgtcaca aaatatatga cggcccttga aattttagat     420
agtacaataa ataccattt aaatagaagt agaagtggta gtattggtag taaaccaatt     480
tgtaataatt taacatcatc atcatcatca tcatcaacaa cagcaactac accatcacca     540
acaactacaa gtaataataa taataataat aataataata ataataataa taataataat     600
aataataata ataataataa taataataat aataataata ataataataa taataataat     660
aataataata ataataatac tacctccacc acaaccacaa caacatcaat tttaatatca     720
tcttcaccac caccatcatc atcatcttct tcttcttcaa atgatgaaca atttaataat     780
aataataata ataataatag taatagtggt ggtagtagta gaatgataac atcaaaatca     840
caaattaaac cattaatagt aacatcaaat actgctgcaa caactacaac aactacaact     900
acaaatacat cagccccaac aacaccaaca aatagagttc aatcaagttt agatgattta     960
ttatttaatt tacctacaat accaagtaat gtgccaacag ttaatggtgg tccaaaaata    1020
tcggcagtac caaagaaagt atcttcatca aaattattaa taccaccctc ttcaaatgta    1080
tcatcatcat caaatattac tttatcatta tcatcatcat caccatcatc atcatcatca    1140
tcatcaacaa gtactgtagt accaattgta caattatcat cgtcaaattc aacaaactca    1200
ccatcaacat cattaccaac aacaccaaga ttatcacaac caactacatc ttatactcaa    1260
ttaataccat cacaacagca acagcaacca actgaaagta atagtagtag taatacaaat    1320
acaacaacaa catcatcatc atcatcatca tcatcatcat cattaacaat atcatcacca    1380
caaccatcaa ataattcaat aagaatatca gcatttggta gatcatcaac acaatttaca    1440
attagtagta atggtatacc aagtagtcca ggacaagttt caaataaaga ttataataat    1500
ataggtaatt taagtaatag ttcaggagaa cgtgtaaaga ataaacaata ttcaatgtta    1560
aatattagta agaaaaccat acttgatgaa tcagatattt catcatcacc aagatcaatt    1620
ggtagtccta atagtataag ggcatcgatt tcaagtcaat taccaccatc attatcatca    1680
```

-continued

```
attggaggtg ggggtggtgg tggtagtgga cctaatgtcg tatcgaataa accattagta      1740
gtaaagaaac catcaacaag tgaacatatt aaaaaagaga atatttggag acaaactatg      1800
ataccgttaa caaaagagga tcatattaaa gtagtattcg agggtatacc aggtaaaaga      1860
gtgattcaaa agttttaat tgataaaaca ccaattgaaa ttaaatcgaa attctttgaa      1920
gatcttaaag atggtgatct tttaaatggt ctcacccaat taccatccct aatacccgaa      1980
cattatgaac taaagtact ctctgtaaat agtacaattt caatgaaac tctaccatta      2040
agaagacaaa ctttaatgca agcatgtaat atttcaagat tatttccaaa attacattta      2100
atttaaaat cagaatcaac aacaatatta gatggtgcat caacaactac aactacaact      2160
acaacaacaa cgacaacaac agcaaatcaa tcatcaaata ttattacaaa atcaaattca      2220
tcattagatt taacaattaa taatagtaat gaaattattg atgttaaagg tcatattcag      2280
gcagagttgg aaattttcga attaattggt acttcattca ctagggttt ggatcagggt      2340
caagaggttg taagttttag aagagatttc gcacaattta gattatcgaa tttcacaagt      2400
actcgtaatg atttatctca aatgattat gtatcttcag agccattacc attgacaata      2460
ccaaataaga tcacgattat ggtgttgtta cctggtgatg gtaaaatcat aaaacgtgta      2520
gattgttgtc caaatagttc agttggtgat gtgaagaaag atctttaa aaagtttgca      2580
atgatcgatc gtgtacatac tcaaggtaaa actcaagatg atttcgtatt aaaggttaca      2640
ggattccggg aatatattct atgcattcat gaattgggta atctaacatc acgtcaacgt      2700
ttttatccaa ctggttcagg tggtgatttc tcattaatgg actatgacta tattcgtcaa      2760
tgtgttggta aaaatcaaac tgtagaatta tcattaacaa ataattcaat attatcatta      2820
aatcaagttt ctgaaaaagt ttcatttatt gataaaattt tagaaacttc tgattttgat      2880
gattatgatg aagatttaga tagtataaat agtaatagtt ttgatgattt aaaacaatca      2940
attcagcaac aacaacaaca acaaattcaa actgtaatta atataaaga aactaataaa      3000
gaaaataaag atagtaataa agaaaataaa gatagtagta gtaataataa taataataat      3060
aataataata ataataataa taataataat aataataata ataataataa taataataat      3120
aatggtaata ataatggtaa taatagtaat aataatagta atagtaatat tagtagagga      3180
tcaattgata gtgaaggtaa tggtagtggt agtggtaatg gtagtgaaca accaacatta      3240
attggtgttc aaaattttc attaccaaat aattcaaaat taccaattaa tattgtaaag      3300
agattgttta gagttaatat tgcaggttta agaaatttaa attttaataa taatgaagat      3360
gctagaaata aatttgcaga tggaaagaat aatcaaccaa atgtatttgt aatggcagag      3420
ttgtattatg gtggtgagtt attgacaaat ccagttttta caccgattgc acaacttgct      3480
tcatatggtg atggtagtgt tgaattccca aattgggaga aaggtattgc attcaccatt      3540
ccaatacgtt atttaccaag ggctgcaaga gcatcgttca cagtttatgt cactaccatc      3600
tcagaggcat tggaatcaca aatggatgaa gtcgttagta aatcaattcc aattggttgg      3660
agtaattgtt tgttaatgaa tcataaaggt atgttacgta tgggtccaac ggcatttaga      3720
ttgtgggacg atggtagaag ggccaatcca attggtactt gtgttgataa tcaagctgcg      3780
aaacaaccaa ttattctatt ggttgaattt gaaagtttca ttagacctat agtttatgtt      3840
gataccgcat tgcaaagtat gatggttaat gatagtagta gcattagtag taatggtgta      3900
gagtcaccat cgattgtatc attttcatcg tcagctgcat cttcatcacc cctaccatct      3960
tcaccattac catcgcctgt agggttaaag aaattggatt tggatgaagc tagaagattg      4020
aaagcattga tggattctga tccattggtt caattaagtg cagaggataa aaagttggtc      4080
```

```
tatggctata gacatatcta aagagtaaa ccaaaggcat tggctaaatt cttactctct      4140
gtaaattgga tagatcctga tcaagttacc gatgcctatc gtcaaatgaa tgattgggcc      4200
ctattgaaac ccgtacaagc attggagata ttggatgcaa agtttgccga tgaacatgtt      4260
agaaatttcg caatcaaaat tattaattca ttctcggatg ctgaattctc agatttcctc      4320
ttacaattga cccaagtgtt aaagtatgaa ccctatcata actctgacct aactcatatc      4380
ttaattcaac gtgcacttag caatcgatcg agaataggge atttcttttt ttggttttta      4440
aaatcagaga tgcatacacc agagattgag gaacgttatg gtttattatt ggagggttat      4500
ctaagaagtt gtggtactca tcgtcaagat ttaattaaac agaatcaagt cttaaaatca      4560
ttacacaccg tagctatggc agtcaaacaa accaatggtt catcagaacg taaaaaggta      4620
ttaatgaaag tcttcaaa gattaaaatc ccagatactt ttcaattgcc attggatcca      4680
cgttgggaag ccaagggttt gatcattgat aaatgtagat atatggattc aaagaagtta      4740
ccactttggt tggtctttga aaatgttgaa cctcatgcaa aacctctcac tgtgatcttt      4800
aaggttggtg atgatttacg tcaagatatt ctaacattac aagtgttgag aattatggat      4860
aagttttgga aaaactctgg tatggatctt aggctacaac cctataaatg tattgccact      4920
ggcgatggta tcggtatgtt ggaggtggtt ttgaatgcca ataccattgc aaatatcaac      4980
aaggatgctg gtggcactgg tgcattactc gaggagaaaa cccttgtcaa ttggttaaaa      5040
gagtgcaata aaaccgaagc tgaatacaat aaggccgtgg aaactttat actctcttgt      5100
gctggttatg ttgtggctac ctatgtcatg ggtattggtg atagacattc cgataatatt      5160
atgatcacaa aattgggtca tctatttcat attgatttcg gtcacttttt aggtaactac      5220
aaaaagaagt atggtttcaa gagagaaaga gctcctttca ttttcactcc acaatatatg      5280
gcaatcgttg gcggtaagga tagtgagaat tttaaacgct tgtcactac atgttgctcc      5340
gcttataata tcctcagaaa gaatacagat ttattcataa atttattcca actaatgtta      5400
agcacaggta taccagagtt acaagtggct gaggatatcg attacctcag aaaagctttg      5460
gctcctggtt tatcagatga agaggctgct gaagaattca ctaaaaatat tagtgtagct      5520
ttaaatacaa aaacagtttt attaaatgat attttccatg gttgggctca ttaa           5574

<210> SEQ ID NO 6
<211> LENGTH: 2487
<212> TYPE: DNA
<213> ORGANISM: Dictyostelium discoideum

<400> SEQUENCE: 6
atgtcttttg ctggaagaat ttcattagat gcatttgatt cttctcatgg tggatcaagt        60
gaaagtccag aaattcatac attatataga gtatcaggat ctttagcatt attatcatgt       120
attggagcat tatttgttat tattacattt attactatta aagatttaaa gaaacatcca       180
acacgtatga tctttttttt atcagtttgt gatgtgttgt ttagtttaaa gtatttggtg       240
acagcagtgt taccacatag tgacagtttt caaacgaaaa gggtggcatg ttatttacaa       300
gcaggtatac agcaattctt tggattggca tctattggat ggagtggtat gatatcgttg       360
aatttgatca ttagcacgag tagaccattc gagaatagtt caacctattc caagttttat       420
catggttgga tatggtcgta ctcgatagtg acaagtgcga tactgttcaa gaattacgat       480
gtcataggac caagtggcga tggcacatgt tggatcaagg cagaggacaa gccattgcta       540
ttgatgtttt tcataccact tttagcatac ttttcaatct cgatctcctc attgatcata       600
gcagcaatct ccactagaaa taaatcacta acatcatcaa ccaccaataa ctcatggtca       660
```

```
gatcgtaatc gtactggaat gttattgaga atgtcgacct acacattggt gtttatcctc      720
tgttgggcag gcccattggc acacagaatc tcgcagatcg caggccacca tgatgcaccc      780
aaccaagcga gtgtgttaat gttttcgat gcaattggtg tatcgattca aggttttatg      840
aatgcactca tttggattac aaatccttca attctcagag gtttccttgg taacattatg      900
aaatatttac cattctcaaa gaaattcatt aaagatggtg aaaacacacc actaattcgt      960
tcacttcaag atgaaaatca agatccaact caattggccg taatgttacg taataatatt     1020
ttaacatgtt cattacgtgg tattgcatta tctgtaaatg ataatttaaa tttatcaaat     1080
tcctcctcat taaataataa taataatcaa tctcatattg gtggtgatat tcatcaacat     1140
ttaccatttg actcattatc atcatcatca ccatcatctt catcaacacc aattaatcat     1200
aattataata gtaataataa tattaataat aataataata atagtaatga taattttgat     1260
aatataaatg aacaatttaa agtttataca gaaaaagaat tatttaaaga tattttgat     1320 atttcaccag atacaaatat gggtagtcat aaatttaaag attattgtcc aaatatattt     1380
gcaaagatta gagcattaaa taatataaca ccatcagatt atttgaaatc atttgattca     1440
tcgttgtttt ttgagaattt atcgaatcag aaattctcag agggtaaaag tggaagtttt     1500
atgtgtttct caccagataa taaattttta attaaaacta tcactcgtca agaatcggta     1560
ttattgaaaa agaaaatcaa caattttac aactatctcg taaagaacaa ccattcattc     1620
ctattgaggt tctatggttg tcataagatt tcaatgccaa atgatcatac tatctatttg     1680
gctatcatgt ccaatgtatt tggtacaatt ccacaaggta taaagattag agaaaggtat     1740
gatcttaaag gttcaaaagt taacagaggt ggcaatgatc ctttgttcaa aggtgatgga     1800
ttaggtttag atttagattt tgtaaacttt agaaaatttt taaatttacc agatggtttt     1860
agtcattcaa tcattcaaca attaaaaaat gattctgctt tcttaacctc tttaaatatt     1920
atggattatt ctttactaat tggtgtaatt ccaaataatg atgattttaa aaagaaatta     1980
attgaatctg gtggtaatat taataatatt ttaagtggtt caaatttaaa taataataat     2040
agtaatagta atagtaatgg tattggtagt ggtagtagtg gtagtaattt taataataat     2100
aataatggac atggtagtgg tggtttatta aaaggtagtt ttacaaattc atcattaatt     2160
tcaaattcat tcgattttc aaatggtatt atatcagcag atgaaaaaga aatctattat     2220
attggtgtta ttgatatact tcaactttat gattttagta gaaaattgga agatttta     2280 aaggtttatt tatttagaaa ggatggtgat ggtatctctg caactagacc tgaaccttat     2340
aaacaaagat tcttaaaaag aatgaatgaa atcattaaaa ataaaaacta taaacataaa     2400
tctgctactc aacaatataa taattcaatt ataaatagta ataataatta ttatcataat     2460
gaagaagaag tttatttga tacataa                                          2487
```

<210> SEQ ID NO 7
<211> LENGTH: 4770
<212> TYPE: DNA
<213> ORGANISM: Dictyostelium discoideum

<400> SEQUENCE: 7

```
atgacaatat gtcaaccaat tccatgtggt ggatcctatt tttggaatat agttgaacca       60
tataaaaatg atgaatatgt atttgtaatg caaagttata atggaccatt taggtggaaa      120
tcagaagaat atagaatcgt tttaatgtgt ggtccaaatt caaatggcta cattatagcc      180
acatcaactt tatttagtga aatcttttca aattgggaga ttatcacaac aatttataaa      240
gaaaagattg aaaaaacagg tcttagtcat ttctctgaca cttttttaat acaactatat      300
```

```
aagaaattag ctaaaaaatt atcacaagtt aattctccaa tctttacaga agaggaacaa    360
aatattcaac caccaccaca accacaacta ccacctcaac aaccaccacc accacctcaa    420
atacaagaat cacaaccaat ccaagaacaa attgaacaaa ttatattacc aacgacatta    480
gaatttccaa aaagtagaga taatgaagaa attaaaatta ttaaaaaaag aaaaatcgtg    540
gcattattta aaacattata tagagttgat gcaatgacaa ttattgaaag ggattatagt    600
tcatcaagtc aatggataga atgggttgat gagtctacag gaatgagacc aattcatgtc    660
gctgtcgaaa gaatgaatgt tcaattggtt aaatatttaa ttgaacgtaa agcagatgta    720
aatataaaag ataatcaagg ttggtcacca ttacatttct catcatttgc tggtagttta    780
gatatttgtc aaattctatt agatcaaggt aatgctgctg ttttaacaat ttcaaaagat    840
ggtacattac cattcatta tttaattaga cattgttatt caataaatgt accatcttca    900
tcatcaaata gtaataataa taaagataat aataataata attataaaga taataataag    960
tttaatagta atttatcaat taattataat aatggtggag attgtaataa tttaacatta   1020
aaacaaaaac aggaaagtaa taataaatta ttttcaattt tatcattatt acttagtaaa   1080
ggtacaccaa taaatgcaaa aactatacgt ggtgaaactg cattacatcg tgcatgttat   1140
tatggttcag cacagtctgt taaattttta catcaaaatg gtgcagatgt aaatgttcaa   1200
aattcacgtg gtgaaacacc actttatttc gcagttgtaa gtcgtcaacg tgagattgta   1260
aaacttttaa tcgaatatgg tagtgatgtt aatattggtg gtgaacgttc tgctttaaaa   1320
gctgctgata aaacaaacca aaatgaaatt tattattttt tagctggttt ttctgatgaa   1380
aaatctgtat ctgattcaaa aagagattat tataataata atgatgaaaa tgatagcaat   1440
aataataata ataattataa tgatgaaaat gataatattc atagacataa tcaaaataat   1500
caaggtaata atcaaaatca ttcaatggat tgttgttcaa agattgaaaa tggtcaagaa   1560
tgtagttgtg gtgatttaag taatacagca catccattct atccacatgt tttcgttttc   1620
attgattttc ctgctggtac aactcattgc tcctattgta aatacttatt atggggtatt   1680
agaaaacaag gtttccaatg tgaagtttgc tcatacattg ttcattcaag atgtaaaaga   1740
caagcaacat taacaaatac ttgtggtata cctgattcaa aagaaactat ttcttcttca   1800
gttgtaaatg atttcttaac aaaatcaaga gaccaaaata ttaataataa taatgaggaa   1860
gaaggtgtag aagtagtaga agaagatcat catcataata acatcaataa taacatcaat   1920
aataataata aaagatcacc acaaagaaaa caaacaataa gacaaccatt acataaacaa   1980
aatattaata gaaaaagatt agaaagttta tataatcatt tcataacatt ggataaagaa   2040
aagaaaggtt caatttttaaa aaaagatttt gaaaaatgtt taggtccaat cattaatagc   2100
tcagaatcat tatcaaatgc tttatttta ggttttaatc caaaaaaaca tgataaaatg   2160
agttatgttg aattttaac tggtgtttct gtattacaaa attcaacttt tgataaacaa   2220
attcaatttt catttaaaat gctagcaggt gaaaaaggtt atattacagt ggaagagttt   2280
ttatcaattt tagaatcaat ctattcttca ttaacaaatt taactattgt aacatgtaat   2340
ccacaagcat ttctaaaaag attattccct gaattttcat ttagttatca aagaaaacaa   2400
aaactattat tacaacaaca acaacaatta cagcagcaac aacaacaaca acaacaacag   2460
cagcaacaaa aatcatcatg gtcctcaact tcaccttcac cttcatcaac tactaattct   2520
cttagaaata gtttaagact atcaagagct atagataata ataataatca taataatcat   2580
aaccataatc ataataatag taatattaac aatgaagatg atttaaatct tgattcagat   2640
tcagactctg attcattccc aacaccatca acctctccac ttttatttaa aattggtata   2700
```

```
aaaaataaac aacaacaaca acaacaacaa caacaacaac aacagcaaca acaacagcaa    2760
caacaacaac aacaacaaca acaacaacaa caacaagaac aacagcaaca acaacaacaa    2820
gaaaaccaac aaataataaa agatgagaat gaaacagtag aaaatcaatc acaagagata    2880
aagcaaaaag aagatgaaaa tcaaaaagaa gttgaaaatc aaaaacaaga tttaaaaaat    2940 caaaagaag aaaaagaaga agaggaagaa ataaaggaac aaagaaaatt tgaaaccaaa     3000
aatgataatt ttgttcaagt taatacaaag aaatcagtta gaggtagtat attttttgca    3060
ccattagatt cacatgaaaa aattaataat atttcaagta ttggtaatca tagatcttta    3120
attagaaata gtagtagtag tgtattagat aataatagta ataatagtaa taataataat    3180
aataataaaa acaataatga atctacagca acaccaaata caactaattc aacaacacca    3240
attacatcag caacaacatc aacatcatca tctccatcat catcatataa aagtcaatca    3300
ttaccagatt taccatcaca tataccaaaa acaccaacaa aatcatcaat tataaataat    3360
aataataata catcaaaaac aataacaact aaatcatcat catcatttga aaatggttta    3420
aataatagtg gaattgataa taattatatt agtaaaaaag aaaaaattga aaatgataaa    3480 gttttttcaat taaatggtag aatttatttt aaagaattta aacaagcatt atcagataat    3540
ttatattttg taaagagttt aggtttagtt aatcattatg aaaatccatt gattagagaa    3600
actgagggta atgatggtct attggttaat cattcatcga attgggtaac atcacaaggt    3660
aaagatgtat caattggtca tataaattgg gagttaattc aatatattat gattggtatt    3720
agaaggtctg caggtgaagc catcgtacta accaatagag caacattgaa gcctaaagat    3780
tttgaaatgg ttgttgaatt caaatatgat ggttggacat tcaaagatca ttacccatta    3840
gcattcaaaa agattagaga aagattagaa attgatccaa agatgtttat gttttccttg    3900
ggtcctgaaa gagtgtttgg taatttacta ttaggcaatc tttcagtgtt gagtgaaatg    3960
aactctagtg gtaaaagtgg cagtgttttc tttagatcga cagagggtga ttatttaatt    4020
aaaaccattc caacacatga agaatcaata ttgaaagcgg ttttaccaac ttatgtacag    4080
catttacaaa aatatccaaa tagttttatta ataaagatat tgggttgtta tacacttcaa    4140
ataaagggta aagcagagat gaaattcttg gtcatgaata acctttttctt cactccatta    4200 ccattgtctg agaagtacga tttgaaaggc tctgtcatca atagaaaagt tgacaagaat    4260
gatttactct tacctgatat cgctttaaaa gatcaagaat ttcatagaat actcgatatt    4320
ggcccagagt ttaaagcacc attattgaaa caaatcgaac atgatacaat gtttttagaa    4380
tctcataata tctgtgatta tagtttattg gttggcattc atactataga tgaaaattca    4440
ccattggctc tttcggatga tgatgatcct gatctttcaa atgtgggtgg tgttaaaaga    4500
gacacttgga agtattgga agaagaattc tttaaaaaaa ctagtggtaa aatctctttta    4560 tttcaaaaga attttggtgg tatccttttca aaaaataaaa aagaagttta tttcatcgct    4620
atcatcgata cttttaccgc ttgggattgg tggaaaaagt ctgaacgtgc cttaaaattc    4680
ttgggtaatg atttagataa aatatctgct gttaatccaa ctgattatcg aaaaagattt    4740
caacattatg tttcaaaaat tgttcaataa                                    4770
```

<210> SEQ ID NO 8
<211> LENGTH: 2406
<212> TYPE: DNA
<213> ORGANISM: Dictyostelium discoideum

```
<400> SEQUENCE: 8
atggatactt taacaaattc ccaagattat tcaaatgtcg atttatcatt agaatcatta      60
gcagaagaat tatataatat tcaatcattt aataaagatg taattttaga tagttttgat     120
attgatgatt atgatcatac tcaattagat acaacaattg attttaataa atttaaaatt     180
ggattaacaa ttttaaagat ttcatcaaaa ggtaaaccac aaaaaaagaa attaatattt     240
gatttagcaa gaaatcaaat tgtatgtggt aaaagaaaaa aagtgaattt ctcagagatt     300
gatgagatta gggttggtca caagaccaac attttcaatc aatttaaatc atcaaagaat     360
ttaaaagagg atatcgaatc gattcaacaa tcattttcaa ttctattcag tggtaatctt     420
agaaagacaa tggatttcgt ttgtagtgat attccagaac gtagacaaat agtgtcggca     480
ttgtatcatg tggttcaaga atcaaagagt gtcaataacg aatacaattt cgttaagcgt     540
gaatgggata gagttggcaa agattccatc gatttctcga cattgaagaa gatattggcc     600
agactcaact tcaccacctc tgacgccgtt ctccacaatc ttatgaaatt cagcgattcc     660
aatagcgact accatttgga cttttctgaa ttttccaatc ttcttaaact actccgtagt     720
catccagaga tgaaacctgt attctataaa tataatggtg caatggtgaa tgggtgcca     780 attcaaggta tgattgattt cttttagaatt gagcaatctg aagtgtggac tgttgaacag     840
tgtagagatt taattaaaaa gtatcatcac gagagattgg attgtatttc atttgaaaat     900
ttcgaggagt ttatttgtgg tgaagcaaac ttggcacaat ccccacacac aagtactgtc     960
tatcaagata cttccaaacc gttgtcctac tatttcataa attcatccca taacacctac    1020
ctttcaggcc accaattgaa aggtctttcc accagtgaaa tgtatacaaa tacactcaga    1080
cagggttgca aatgcgttga attggacgtt tgggatggta atgatggtga tccaatcatt    1140
ttccatggta atacattaac aagtcaaatt aaattctctc atgtttgtga aaccattaaa    1200
gctagaggat ttgaaacttc accatatcct gtcatactca gtttagaagt tcattgttca    1260
gtacctcaac aaatcatgat ggcaaatcat atgaaagaaa ttttggtga atgttacca    1320 actccattac cagagggtac aaaagaatta ccaacattag actcattaaa atataaaatt    1380
ttattgaaag tcatacttc tcatactcat gtgagtgctc ttggtaattc atcagcatca    1440
tcatctcaat caaatattca aactgatgac aatgatgatg atggtgctgt tgatttaaca    1500
gaatatgatg aagttgatga tagaagtgca tcatcatcat cctcatcatt ctctttatca    1560
tttggtagta gtggtaaaaa gaagaaaatt acaaaaatta aaattgcacc agaatttgaa    1620
gaattaattt atttagtttc acatggattt aaatctggta atactacaaa agaaattcca    1680
tcatataaaa ttcattcatt ggttgaggag aaagttaaac aattggtaca atctgaacca    1740
agagaggtcg ttgaagcatc acaaaatcat ttacttagag tttatccaag aggtactcgt    1800
ttcgatagta gcaattttga tccaatgcca ggttggagta ttggttgtca attggcagct    1860
ttgaatcaac aaacttcatc ggaaccaatg tggatcaatg atggtatgtt ctcagataat    1920
ggtggttgtg gctacgtttt aaaaccaccct tgtcttttac caggtgaatg tgaaacttat    1980
gaccctacct caccagagag aatcaagtca agtaaatact caagactcat agtaaatgta    2040
attagtgcaa gacaattacc aaagtatact aaatcaacta aaggtgaagt cattgatcct    2100
tatgttaccc tatcaatcgt tggcactcat ttcgatcaaa aagttgaaaa actaaagtt    2160 atcgacaata atggtttcaa tccacattgg ggtgaagaat ttgaattccc actttacaat    2220
tctcaattat caatgttatt aattcgtgtt gatgataaag ataaagttgg tcacaataga    2280
attggtcatc attgtattag agttgaaaat attagaccag gttatagaat cttaaaatta    2340
```

```
aaaaataatt ttaatagaac aattccatta gctaatttat tatgtaaatt tacatttgtt    2400
gaataa                                                               2406

<210> SEQ ID NO 9
<211> LENGTH: 2283
<212> TYPE: DNA
<213> ORGANISM: Dictyostelium discoideum

<400> SEQUENCE: 9
atgaaattta attacccaga acaagaaga gatgattctg tttttgatat atttaaatca      60
acagaaaaag gaagtgttaa agtttatgat ccatatcgtc atttagaaga tcaacaatca    120
ccagaaacaa agaaatgggt tgatgaagaa aataaaatta caagatcatt tttagatcaa    180
gataatacaa gtgaaaagat ttcaaatgaa attatgaaaa tgttaaattt tgaaagattt    240
gattggttta aagaagagg ttcaaaatta ttcttttcaa gaaatccaaa tacattaaat     300
caaaatataa tttatttgat tgatattgat caaatttcaa ttagtaaaga tggtaaatca    360
agtgcaaaag gatttgaaaa tgcaattgaa ttcttaaatc aaacactta ttcaaaagat     420 ggtacatgga gtttaaaatc atttgtaatc tcaagagtg gtgatcatgt ttgttttagt    480
tattcaaagg caggttctga ttgggaagag attgcagtaa agaaaattat aacaactaat    540
gagttaaaga caaataagga tgatgaagag gagaaagaag atttaaaaaa gaagaattgt    600
ttacattatg cagttgtgga tctaccagat tcaataaatt ggtgtaaatt tacttcgatt    660
aaatgggatg agaatgagac tggtttcatc tataatcgat atccaaaacc ggaaaaagta    720
tccgatgatg ataaaggcac tgaaaccgac accaacttga ataataaagt ttattatcat    780
aaattaggtg atgccaatga gtcgtttgat agagtggttt tcgaatgtcc agagaaccca    840
caatggatat ttggtactga gttctctcat gaccatagcc ctttgtttat cagcgctttc    900
agggactgca atgttgagca taatctatat gtaattagaa atttccaaga ggcaattgca    960
aataaatcag cctttaaagt cgaggccctc atagataatt tcgatgcttg ttattattat   1020
attacaaata ctaaacaagg tgaatatttc tttttaacca atttatctgc accattcaat   1080
agattaatct caattcaatt gaatgatgat caaccaatcg taccaaaattc aaagagtaaa  1140 ttagagttta aagagatcat tccagagaaa gactatgtat tggaatcggt tagtcgttcc   1200
tctcaagaga aattctacgt ttcctatcaa aaacatgttc aagatatcat tgaagtatat   1260
gatttcaatg gtaaatattt aaaggatatt aaattaccag gccctggaag tgcttcatta    1320
tcagccactg agtatcatga tcatatcttt ataaacttt caaatttagt ttcaccatcg    1380
gtaacttatt atatggattc aaagaatgat gaattgttac tctttaaaga accacacatt   1440
gaaggcttca atcatcaga ttatgaatgt aaacaagtct tttatgaatc tccaaaggat    1500
aaaacaaaga ttccaatgtt tatagcctat aagaagacca cagatatcac cagtggtaat   1560
gctccaacct atatgactgg ttatggtggt tcaatatctc ttacactca atcattctca    1620 attagaaata tttacttttt aaataaaattc aatggtatct ttgtaattgc aaacattaga   1680
ggtggtggtg agtatggtaa agcttggcat gaggctggtt caaaaaagaa taagcaaaat   1740
tgctttgatg attttattgg tgccgctgaa tatttgataa aggaaaacta tacaaaccaa   1800
aacaaattgg ccgtaagagg tggtagtaat ggtggtttgt taatgggtgc aatttcaaat   1860
caacgtcctg atctatttaa atgtgttgta gcagacgttg gtgttatgga tatgctaaga   1920
ttccatcttc atactatcgg tagtaattgg gtctctgatt atggtagaag tgataatcct   1980
gatgattttg atgtactcat taaatattct cctctaaata atgtcccaaa ggattcaaat   2040
```

-continued

```
caatatccat caattatgct ttgtactggt gaccatgatg atcgtgtcat tcctgctcac      2100
tcttataaat tcatctctga attacaatat caacttggta aaaaagttga tactccactt      2160
ttaattagag ttgataaaga ttctggtcat ggtgctggta aaggtttatc aaaacaaaat      2220
aatgaaatag ctgatatctt taatttcttt tcaaaagttt taaatgttaa attaaatttt      2280
taa                                                                    2283
```

<210> SEQ ID NO 10
<211> LENGTH: 386
<212> TYPE: PRT
<213> ORGANISM: Dictyostelium discoideum

<400> SEQUENCE: 10

```
Met Gly Asp Asn Lys Lys Glu Asn Ile Arg Ile Ile Leu Ser Leu Asp
1               5                   10                  15

Gly Gly Gly Thr Lys Gly Leu Tyr Thr Ile Glu Val Ile Glu His Phe
            20                  25                  30

Val Lys Leu Ser Ser Asp Phe Thr Lys His Val Asp Leu Phe Gly
        35                  40                  45

Gly Thr Ser Thr Gly Gly Ile Leu Ser Ile Ala Lys Ser Lys Glu Ile
    50                  55                  60

Ser Asn Ser Glu Leu Leu Asn Met Tyr Glu Gly Lys Glu Ser Lys Lys
65                  70                  75                  80

Ile Phe Gly Ser Leu Trp Asp Glu Val Lys Gly Val Phe Thr Arg Gly
                85                  90                  95

Glu Met Phe Asn Ser Asp Glu Leu Ile Asn Ile Ala Asn Ser Trp Phe
            100                 105                 110

Pro Ser Ser Pro Asp Gly Ala Asp Thr Gln Ile Thr Glu Leu Asn Glu
        115                 120                 125

Lys Lys Phe Phe Val Val Ser Leu Lys Lys Thr Gly Glu Lys Asn Asp
    130                 135                 140

Ile Leu Thr Pro Val Ile Ile Ser Asn Tyr Lys Phe Asp Glu Thr Thr
145                 150                 155                 160

Thr Ile Ala Gly Asn Asn Asn Asn Asn Asn His Phe Ile Lys Gly
                165                 170                 175

Glu Glu Ile Glu Arg Leu Tyr Thr Ile Gly Glu Glu Ala Leu Ser Leu
            180                 185                 190

Ala Asp Ala Ile Arg Ala Thr Ser Ser Ile Pro Ala Ala Phe Gln Lys
        195                 200                 205

His Lys Gln Gly Asp Glu Glu Tyr Leu Asp Gly Gly Phe Lys Tyr Asn
    210                 215                 220

Asn Pro Met Glu Ile Ala Tyr His Glu Ala Arg Ile Ile Tyr Pro Asn
225                 230                 235                 240

Asp Tyr Leu Val Ile Ile Ser Ile Gly Cys Thr Asp Lys Asp Val Gln
                245                 250                 255

Gly Leu Thr Glu Asn Asn Lys Glu Ile Asn Asp Arg Leu Glu Lys Leu
            260                 265                 270

Leu Asp Asn Met Glu Asp Gly Val Glu Thr Lys Gly Ile Phe Ser Val
        275                 280                 285

Pro His Tyr Leu Lys Ser Asn Trp Ile Thr Asp Phe Leu Asp Thr Ile
    290                 295                 300

Lys Leu Asn Lys Asn Ser Lys Ser Gln Gln Leu Tyr Ile Glu Ala
305                 310                 315                 320
```

Met Gln Asn Ile Lys Asp Ser Asn Ala Phe Leu Arg Phe Asp Ser
                    325                 330                 335

Val Glu Thr His Ser Leu Leu Ser Phe Ser Asp Thr Ser Lys Glu Phe
            340                 345                 350

Phe Glu Lys Leu Arg Lys Cys Ser Ser Ala Leu Ser Lys Asp Ser Glu
        355                 360                 365

Phe Ile Arg Thr Ala Asp Leu Leu Lys Arg Ile Ile Asp Leu Lys Lys
    370                 375                 380

Asp Glu
385

<210> SEQ ID NO 11
<211> LENGTH: 380
<212> TYPE: PRT
<213> ORGANISM: Homo sapiens

<400> SEQUENCE: 11

Glu Arg Ile Ile Pro Tyr Leu Leu Arg Leu Arg Gln Ile Lys Asp Glu
1               5                   10                  15

Thr Leu Gln Ala Ala Val Arg Glu Ile Leu Ala Leu Ile Gly Tyr Val
            20                  25                  30

Asp Pro Val Lys Gly Arg Gly Ile Arg Ile Leu Ser Ile Asp Gly Gly
        35                  40                  45

Gly Thr Arg Gly Val Val Ala Leu Gln Thr Leu Arg Lys Leu Val Glu
    50                  55                  60

Leu Thr Gln Lys Pro Val His Gln Leu Phe Asp Tyr Ile Cys Gly Val
65                  70                  75                  80

Ser Thr Gly Ala Ile Leu Ala Phe Met Leu Gly Leu Phe His Met Pro
                85                  90                  95

Leu Asp Glu Cys Glu Glu Leu Tyr Arg Lys Leu Gly Ser Asp Val Phe
            100                 105                 110

Ser Gln Asn Val Ile Val Gly Thr Val Lys Met Ser Trp Ser His Ala
        115                 120                 125

Phe Tyr Asp Ser Gln Thr Trp Glu Asn Ile Leu Lys Asp Arg Met Gly
    130                 135                 140

Ser Ala Leu Met Ile Glu Thr Ala Arg Asn Pro Thr Cys Pro Lys Val
145                 150                 155                 160

Ala Ala Val Ser Thr Ile Val Asn Arg Gly Ile Thr Pro Lys Ala Phe
                165                 170                 175

Val Phe Arg Asn Tyr Gly His Phe Pro Gly Ile Asn Ser His Tyr Leu
            180                 185                 190

Gly Gly Cys Gln Tyr Lys Met Trp Gln Ala Ile Arg Ala Ser Ser Ala
        195                 200                 205

Ala Pro Gly Tyr Phe Ala Glu Tyr Ala Leu Gly Asn Asp Leu His Gln
    210                 215                 220

Asp Gly Gly Leu Leu Leu Asn Asn Pro Ser Ala Leu Ala Met His Glu
225                 230                 235                 240

Cys Lys Cys Leu Trp Pro Asp Val Pro Leu Glu Cys Ile Val Ser Leu
                245                 250                 255

Gly Thr Gly Arg Tyr Glu Ser Asp Val Arg Asn Thr Val Thr Tyr Thr
            260                 265                 270

Ser Leu Lys Thr Lys Leu Ser Asn Val Ile Asn Ser Ala Thr Asp Thr
        275                 280                 285

Glu Glu Val His Ile Met Leu Asp Gly Leu Leu Pro Pro Asp Thr Tyr
    290                 295                 300

```
Phe Arg Phe Asn Pro Val Met Cys Glu Asn Ile Pro Leu Asp Glu Ser
305                 310                 315                 320

Arg Asn Glu Lys Leu Asp Gln Leu Gln Leu Glu Gly Leu Lys Tyr Ile
            325                 330                 335

Glu Arg Asn Glu Gln Lys Met Lys Lys Val Ala Lys Ile Leu Ser Gln
        340                 345                 350

Glu Lys Thr Thr Leu Gln Lys Ile Asn Asp Trp Ile Lys Leu Lys Thr
    355                 360                 365

Asp Met Tyr Glu Gly Leu Pro Phe Phe Ser Lys Leu
370                 375                 380

<210> SEQ ID NO 12
<211> LENGTH: 6
<212> TYPE: PRT
<213> ORGANISM: Dictyostelium discoideum

<400> SEQUENCE: 12

Gly Gly Gly Thr Lys Gly
1               5

<210> SEQ ID NO 13
<211> LENGTH: 6
<212> TYPE: PRT
<213> ORGANISM: Homo sapiens

<400> SEQUENCE: 13

Gly Gly Gly Thr Arg Gly
1               5

<210> SEQ ID NO 14
<211> LENGTH: 5
<212> TYPE: PRT
<213> ORGANISM: Dictyostelium discoideum

<400> SEQUENCE: 14

Gly Thr Ser Thr Gly
1               5

<210> SEQ ID NO 15
<211> LENGTH: 5
<212> TYPE: PRT
<213> ORGANISM: Homo sapiens

<400> SEQUENCE: 15

Gly Val Ser Thr Gly
1               5

<210> SEQ ID NO 16
<211> LENGTH: 1161
<212> TYPE: DNA
<213> ORGANISM: Dictyostelium discoideum

<400> SEQUENCE: 16
atgggagata taaaaaaga aaatatcaga atcatcctta gtttagacgg tggtggcaca      60
aaaggattat atacaatcga ggtaatagaa cattttgtta aattatcagg aagtgatttt    120
acaaaacatg tagatttatt tggtggtaca agtactggag gtattttatc aattgcaaag    180
agtaaagaga tttcaaattc agaattattg aacatgtatg aaggaaaaga atcaaagaaa    240
attttcggtt ccctttggga cgaagttaaa ggtgttttta caagaggaga aatgttcaat    300
tcagatgaac tcataaatat tgcaaatagt tggtttccat catcaccaga tggagctgat    360
```

```
acccaaatta cagagttaaa tgaaaagaaa ttctttgttg tatcattaaa aaagactggt    420
gaaaaaaatg atatcttaac accagtaatc atttcaaatt ataaatttga tgaaacaaca    480
acaattgctg gtaataataa taataataat aatcatttta ttaaaggtga agaaatagag    540
agactttata caattggtga agaagcactt tcattagctg atgcaattag agctacgtca    600
agtattccag cagcttttca aaaacataag caaggtgatg aggaatattt agatggtggt    660
tttaaatata ataatccaat ggagattgct tatcatgagg caagaatcat ttatccaaat    720
gattatcttg ttatcatttc aattggttgt actgataagg atgtgcaagg attaacagag    780
aataataaag agattaacga tcgtttggaa aaactacttg acaatatgga agatggagtt    840
gaaactaaag gaattttctc agtaccacat tatttaaaga gtaattggat aactgatttt    900
ttggatacta tcaaattaaa caaaaattca aaatcttctc aacaactcta cattgaagca    960
atgcaaaata ttaaagatag caatgctttc cttttaagat ttgattctgt cgaaactcat   1020
tcattactta gctttagtga tacttcaaaa gaatttttg aaaagttaag aaaatgttca    1080
tcagcattat caaaagattc agagtttata agaactgctg atctacttaa aagaattatc   1140
gatttaaaaa aagatgaata a                                            1161

<210> SEQ ID NO 17
<211> LENGTH: 29
<212> TYPE: DNA
<213> ORGANISM: Dictyostelium discoideum

<400> SEQUENCE: 17
atgggagata ataaaaaaga aaatatcag                                      29

<210> SEQ ID NO 18
<211> LENGTH: 38
<212> TYPE: DNA
<213> ORGANISM: Dictyostelium discoideum

<400> SEQUENCE: 18
taagaattca tgggagataa taaaaagaa aatatcag                             38

<210> SEQ ID NO 19
<211> LENGTH: 2004
<212> TYPE: DNA
<213> ORGANISM: Dictyostelium discoideum

<400> SEQUENCE: 19
atgtcaagcc tttcaacaaa aacagattta cttggtgacc cagatttat ccgtcttcaa     60 agtgttgaag tagacggtag tgaagttata ccaggcgaaa ctagaccaag aagaaacact   120
aaattcccaa aattaacaaa ttcaccagac ggtaaaacct ttaccttgta tgatgtttat   180
agaataaata aagattcaga ttcaaacttt ttaggtattc gtgaattatt agcagatggc   240
aaaagaggtg attacaaatg gatttcttat aaacaagcat gcattagagc aaataacatt   300
ggttcagctt tagttcaatt aggtttaaat aagggtgata gaattggtat ttttttcaatt   360 aatagaccag aatgggtttt atcagatatg gcagcaatga atcattcact tgtaccagtt   420
gcattatatg caacattagg tgccaatgca attgaatatg ttgttaatca ttcagagatt   480
tcagtacttt tatgtgaagg taaaaatgtt gaaaagattc tttcaatgcc aggtacaacc   540
attaaaacaa ttgtcagtta tgatccatta ccacaagcaa cattagataa attcaaggat   600
aatgaaaacg ttaaacttta cctcttatca gattttgaaa aattgggtga acaaaatcca   660
gcccaacatg aagtcccatc accagaagat ttatgtacat tactttacac ctctggttca   720
```

```
actggtaatc caaagggtgt aatgttaact catacaaata tggtcagtga agttgcaggt    780
gccaactttt caccagcagg tgtaattcca gaggatgttc atatgtcata cctcccattg    840
gctcactcat ttgaacgtgc cgtcgtttca ttgatgtgtt atgttggtgg tcaaattggt    900
ttcttctctg gtttaattcc agagttattc aacgatatcc aagttttacg tccaaccttt    960
ttatgtggtg ccccaagagt atggcaacgt cttcacgaca aactttggtt cactgtcaac   1020
aatgatagtt ggttaaagaa attcctcttc aattggggtc tcaactctaa acaatctgca   1080
ttaagacttg gttcaaccac tccaatttgg gataaattgg ttttctcaaa aacaaaggat   1140
agacttggtg gtcgtgttaa attcatcctt tccggttccg ctccattgga tccaaaatta   1200
gccgaattct tacgtgcttg tttctgttgt ccagtcgtct ctggttatgg tctctctgaa   1260
aatgtaggtg gtgcctctgt tgcctatcca gaagataaca atgtaggtca tgttggtcca   1320
ccactcagtg cctgtgaaat gaaattaatc gacgttccag agatgaacta tttctctact   1380
gataaaccat gtccaagagg tgaggtttgt attcgtggtt tcaacgtttt caaaggttac   1440
tttaaggatc cagaaaagac caagaagat ctcaaagaag atggttggtt ccatactggt   1500
gatattggtc gttggaatga aaatggtacc ctctcaatca ttgatcgtaa gaaaaatatc   1560
ttcaaattat ctcaaggtga atacgttgcc gccgaatatt tggaatctgt tttcgttcgt   1620
tcaccatttg cctctcaagt atttgtctat ggtgattcat taaatagttt cttggttggt   1680
gttgtcgtac cagattttga agttgtccaa aaattattcg cttccaaata tccagaactt   1740
gatgtttcaa accatgcaac cctcgcaaaa tcaaagaac tctacaaaga aattttatca   1800
agtttcgatg cttgcgctgc cgaagccaaa ttacatggtt ttgaaaaatt aaaacatatc   1860
tacgtagaac atgaaccatt cactgaggaa aacaatttat taactccatc attcaaacca   1920
aagagaccac aactcaaaga aagatatcaa accattattg atacccttta tgctgaatac   1980
aaacgtgatc atccagacgt ataa                                          2004
```